US006218141B1

(12) United States Patent
Barenkamp

(10) Patent No.: US 6,218,141 B1
(45) **Date of Patent: *Apr. 17, 2001**

(54) HIGH MOLECULAR WEIGHT SURFACE PROTEINS OF NON-TYPEABLE HAEMOPHILUS

(75) Inventor: Stephen J. Barenkamp, Webster Grove, MO (US)

(73) Assignees: St. Louis University; Washington University, both of St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/719,641

(22) Filed: Sep. 25, 1996

Related U.S. Application Data

(62) Division of application No. 08/302,832, filed as application No. PCT/US93/02166 on Mar. 16, 1993, now Pat. No. 5,603,938.

(30) Foreign Application Priority Data

Mar. 16, 1992 (GB) .................................................. 9205704

(51) Int. Cl.[7] ..................................................... C12P 21/06

(52) U.S. Cl. ....................... 435/69.1; 435/69.3; 435/71.1; 435/71.2; 530/350; 424/185.1; 424/256.1

(58) Field of Search ............................ 424/256.1, 197.11, 424/185.1; 530/350; 435/69.3, 69.1, 69.7, 71.1, 71.2

(56) References Cited

U.S. PATENT DOCUMENTS 6,013,514 1/2000 Chong et al. .

OTHER PUBLICATIONS

Pediatric Infectious Disease Journal, vol. 9, No. 5, issued May 1990, S.J. Barenkamp et al., "Development of Serum Bactericidal Activity Following Nontypable *Haemophilus influenzae* Acute Otitis Media", pp. 333–339, see entire document.

Journal of Clinical Microbiology, vol. 29, No. 11, issued Nov. 1991, A.C. Caputa et al., "110 Kilodalton Recombinant Protein which is Immunoreactive with Sera from Humans, Dogs, and Horses with Lyme Borreliosis", pp. 2418–2423, see entire document.

Joint Meeting of the American Pediatric Society and the Society for Pediatric Research, 07–10 May 1990, S.J. Barenkamp, "Cloning and Expression of Genes for Nontyable *Haemophilus influenzae* (NTHI) High Molecular Weight (HMW) Outer Membrane Proteins which are Targets of Bactericidal Antibody", Abstract 983, Pediatric Research, vol. 27, (4 part 2).

The Journal of Infectious Diseases, vol. 165 (Suppl.), issued Aug. 1992, S.J. Barenkamp, "Outer Membrane Protein and Lipopolysaccharides of Nontypeable *Haemophilus influenzae*", S181–S184, see entire document.

Infection and Immunity, vol. 60(4), issued Apr. 1992, S.J. Barenkamp et al, Cloning, Expression and DNA Sequence Analysis of Genes Encoding Nontypable *Haemophilus influenzae* High–Molecular–Weight Surface–Exposed Proteins Related to Filamentous Hemagglutinin of *Bordetella pertussis* pp. 1302–1313, see entire document.

Infection and Immunity, vol. 56(1), issued Jan. 1988, E.J. Hansen, Immune Enhancement of Pulmonary Clearance on Nontypable *Haemophilus influenzae*, pp. 182–190, see entire document, especially Figures 3 and 4.

Infection and Immunity, vol. 52(2), issued May 1986, S.J. Barenkamp, "Protection by Serum Antibodies in Experimental Nontypable *Haemophilus influenzae* Otiti Media", pp. 572–578, see Figures 1 and 2.

Proceedings of the National Academy of Sciences USA, vol. 80, issued Mar. 1983, R.A. Young et al, "Efficient Isolation of Genes by Using Antibody Probes", pp. 1194–1198, see entire document.

Infection and Immunity, vol. 45(3), issued Sep. 1984, R. Schneerson et al, "Serum Antibody Responses of Juvenile and Infant Rhesus Monkeys Injected with *Haemophilus influenzae* Type b and Pneumococcus Type 6A Capsular Polysaccharide–Protein Conjugates", pp. 582–591, see entire document.

Journal of Molecular Biology, vol. 157, issued 1982, J. Kyte et al, "A Simple Method for Displaying the Hydropathic Character of a Protein", pp. 105–132, see entire document.

Proceeding of the National Academy of Sciences, vol. 78(6), issued Jun. 1981, T.P.Hopp et al, "Prediction of Protein Antigenic Determinants from Amino Acid Sequences", pp. 3824–3828, see entire document.

Pediatr. Infect. Dis. J., 9: 333–339, 1990, Stephen J. Barenkamp and Frank F. Bodor, "Development of Serum Bacterial Activity Following Nontypable *Haemophilus influenzae* Acute Otitis Media".

Green et al, Infection and Immunity 61:1950–1957, 1993.

Erwin et al, Can. Journ.of Microbioligy 34:, 723–729, 1988.

Thomas et al, Infection and Immunity, 58: 1909–1913, 1990.

Barenkamp, Pediatric Research vol. 29, 167A, Abstract 985, 1991.

Barenkamp, Abstract 983, Pediatric Research vol. 27.

Houghten et al, Vaccine 86, pp. 21 to 25.

(List continued on next page.)

*Primary Examiner*—Jennifer Graser
(74) *Attorney, Agent, or Firm*—Shoemaker and Mattare, Ltd.

(57) ABSTRACT

High molecular weight surface proteins of non-typeable *Haemophilus influenzae* which exhibit immunogenic properties and genes encoding the same are described. Specifically, genes coding for two immudominant high molecular weight proteins, HMW1 and HMW2, have been cloned, expressed and sequenced, while genes coding for high molecular proteins HMW3 and HMW4 have been cloned, expressed and partially sequenced.

2 Claims, 68 Drawing Sheets

OTHER PUBLICATIONS

Green et al Infection and Immunity 61:1950–1957 1993.*

Gulig, Paul Antony Dissertation Abstracts Internat. vol. 46/08–B p. 2613, 1985.*

Houghten et al Vaccines 86, pp. 21–25, 1986.*

Barenkamp Pediatr. Res 29 167A 1991(6).*

Barenkamp et al Infection and Immunity 60: 1302–1313, 1992 (1).*

Barenkamp et al. The Journal of Infectious Disease 165(Suppl) S181–S184 (2), 1992.*

Barenkamp et al (3) Pediatr Res 31: 179A, 1992.*

Thomas et al Infection & Immunity 58:1909–13, 1990.*

Kimura et al Infection and Immunity 47: 253–9, 1985.*

Barenkamp et al (4) Pediatr. Infect Dis J. 9:333–339, 1990.*

Barenkamp et al, (5) Abstracts of the fifth Internation Symp. Recent Adv. in Otitis Media p. 119 A6–133, 1991.*

* cited by examiner

FIG. 1A. DNA SEQUENCE OF HIGH MOLECULAR WEIGHT PROTEIN I (HMW1)

```
  1 ACAGCGTTCT CTTAATACTA GTACAAACCC ACAATAAAAT ATGACAAACA
 51 ACAATTACAA CACCTTTTTT GCAGTCTATA TGCAAATATT TTAAAAAATA
101 GTATAAATCC GCCATATAAA ATGGTATAAT CTTTCATCTT TCATCTTTCA
151 TCTTTCATCT TTCATCTTTC ATCTTTCATC TTTCATCTTT CATCTTTCAT
201 CTTTCATCTT TCATCTTTCA TCTTTCATCT TTCATCTTTC ACATGCCCTG
251 ATGAACCGAG GGAAGGGAGG GAGGGGCAAG AATGAAGAGG GAGCTGAACG
301 AACGCAAATG ATAAAGTAAT TTAATTGTTC AACTAACCTT AGGAGAAAAT
351 ATGAACAAGC TATATCGTCT CAAATTCAGC AAACGCCTGA ATGCTTTGGT
401 TGCTGTGTCT GAATTGGCAC GGGGTTGTGA CCATTCCACA GAAAAAGGCA
451 GCGAAAAACC TGCTCGCATG AAAGTGCGTC ACTTAGCGTT AAAGCCACTT
501 TCCGCTATGT TACTATCTTT AGGTGTAACA TCTATTCCAC AATCTGTTTT
551 AGCAAGCGGC TTACAAGGAA TGGATGTAGT ACACGGCACA GCCACTATGC
601 AAGTAGATGG TAATAAAACC ATTATCCGCA ACAGTGTTGA CGATATCATT
651 AATTGGAAAC AATTTAACAT CGACCAAAAT GAAATGGTGC AGTTTTTACA
701 AGAAAACAAC AACTCCGCCG TATTCAACCG TGTTACATCT AACCAAATCT
```

FIG. 1B.

```
 751 CCCAATTAAA AGGGATTTTA GATTCTAACG GACAAGTCTT TTTAATCAAC
 801 CCAAATGGTA TCACAATAGG TAAAGACGCA ATTATTAACA CTAATGGCTT
 851 TACGGCTTCT ACGCTAGACA TTTCTAACGA AAACATCAAG GCGCGTAATT
 901 TCACCTTCGA GCAAACCAAA GATAAAGCGC TCGCTGAAAT TGTGAATCAC
 951 GGTTTAATTA CTGTCGGTAA AGACGGCAGT GTAAATCTTA TTGGTGGCAA
1001 AGTGAAAAAC GAGGGTGTGA TTAGCGTAAA TGGTGGCAGC ATTTCTTTAC
1051 TCGCAGGGCA AAAAATCACC ATCAGCGATA TAATAAACCC AACCATTACT
1101 TACAGCATTG CCGCGCCTGA AAATGAAGCG GTCAATCTGG GCGATATTTT
1151 TGCCAAAGGC GGTAACATTA ATGTCCGTGC TGCCACTATT CGAAACCAAG
1201 GTAAACTTTC TGCTGATTCT GTAAGCAAAG ATAAAAGCGG CAATATTGTT
1251 CTTTCCGCCA AAGAGGGTGA AGCGGAAATT GGCGGTGTAA TTTCCGCTCA
1301 AAATCAGCAA GCTAAAGGCG GCAAGCTGAT GATTACAGGC GATAAAGTCA
1351 CATTAAAAAC AGGTGCAGTT ATCGACCTTT CAGGTAAAGA AGGGGGAGAA
1401 ACTTACCTTG GCGGTGACGA GCGCGGCGAA GGTAAAAAGG GCATTCAATT
1451 AGCAAAGAAA ACCTCTTTAG AAAAAGGCTC AACCATCAAT GTATCAGGCA
1501 AAGAAAAAGG CGGACGCGCT ATTGTGTGGG GCGATATTGC GTTAATTGAC
```

FIG. 1C.

```
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCTTTGAG AAAGGAAGCA
2101  ACCAAGTCAT TACAGGTCAA GGGACTATTA CCTCAGGCAA TCAAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTTAACCTC
```

FIG.1D.

```
2351  CTTAAATGTT TCCGAGAGTG GCGAGTTTAA CCTCACTATT GACTCCAGAG
2401  GAAGCGATAG TGCAGGCACA CTTACCCAGC CTTATAATTT AAACGGTATA
2451  TCATTCAACA AAGACACTAC CTTTAATGTT GAACGAAATG CAAGAGTCAA
2501  CTTTGACATC AAGGCACCAA TAGGGATAAA TAAGTATTCT AGTTTGAATT
2551  ACGCATCATT TAATGGAAAC ATTTCAGTTT CGGGAGGGGG GAGTGTTGAT
2601  TTCACACTTC TCGCCTCATC CTCTAACGTC CAAACCCCCG GTGTAGTTAT
2651  AAATTCTAAA TACTTTAATG TTTCAACAGG GTCAAGTTTA AGATTTAAAA
2701  CTTCAGGCTC AACAAAAACT GGCTTCTCAA TAGAGAAAGA TTTAACTTTA
2751  AATGCCACCG GAGGCAACAT AACACTTTTG CAAGTTGAAG GCACCGATGG
2801  AATGATTGGT AAAGGCATTG TAGCCAAAAA AAACATAACC TTTGAAGGAG
2851  GTAACATCAC CTTTGGCTCC AGGAAAGCCG TAACAGAAAT CGAAGGCAAT
2901  GTTACTATCA ATAACAACGC TAACGTCACT CTTATCGGTT CGGATTTTGA
2951  CAACCATCAA AAACCTTTAA CTATTAAAAA AGATGTCATC ATTAATAGCG
3001  GCAACCTTAC CGCTGGAGGC AATATTGTCA ATATAGCCGG AAATCTTACC
3051  GTTGAAAGTA ACGCTAATTT CAAAGCTATC ACAAATTTCA CTTTTAATGT
3101  AGGCGGCTTG TTTGACAACA AAGGCAATTC AAATATTTCC ATTGCCAAAG
3151  GAGGGGCTCG CTTTAAAGAC ATTGATAATT CCAAGAATTT AAGCATCACC
```

FIG. 1E.

```
3201  ACCAACTCCA GCTCCACTTA CCGCACTATT ATAAGCGGCA ATATAACCAA
3251  TAAAAACGGT GATTTAAATA TTACGAACGA AGGTAGTGAT ACTGAAATGC
3301  AAATTGGCGG CGATGTCTCG CAAAAAGAAG GTAATCTCAC GATTTCTTCT
3351  GACAAAATCA ATATTACCAA ACAGATAACA ATCAAGGCAG GTGTTGATGG
3401  GGAGAATTCC GATTCAGACG CGACAAACAA TGCCAATCTA ACCATTAAAA
3451  CCAAAGAATT GAAATTAACG CAAGACCTAA ATATTTCAGG TTTCAATAAA
3501  GCAGAGATTA CAGCTAAAGA TGGTAGTGAT TTAACTATTG GTAACACCAA
3551  TAGTGCTGAT GGTACTAATG CCAAAAAAGT AACCTTTAAC CAGGTTAAAG
3601  ATTCAAAAAT CTCTGCTGAC GGTCACAAGG TGACACTACA CAGCAAAGTG
3651  GAAACATCCG GTAGTAATAA CAACACTGAA GATAGCAGTG ACAATAATGC
3701  CGGCTTAACT ATCGATGCAA AAAATGTAAC AGTAAACAAC AATATTACTT
3751  CTCACAAAGC AGTGAGCATC TCTGCGACAA GTGGAGAAAT TACCACTAAA
3801  ACAGGTACAA CCATTAACGC AACCACTGGT AACGTGGAGA TAACCGCTCA
3851  AACAGGTAGT ATCCTAGGTG GAATTGAGTC CAGCTCTGGC TCTGTAACAC
3901  TTACTGCAAC CGAGGGCGCT CTTGCTGTAA GCAATATTTC GGGCAACACC
3951  GTTACTGTTA CTGCAAATAG CGGTGCATTA ACCACTTTGG CAGGCTCTAC
```

FIG.1F.

```
4001  AATTAAAGGA ACCGAGAGTG TAACCACTTC AAGTCAATCA GGCGATATCG
4051  GCGGTACGAT TTCTGGTGGC ACAGTAGAGG TTAAAGCAAC CGAAAGTTTA
4101  ACCACTCAAT CCAATTCAAA AATTAAAGCA ACAACAGGCG AGGCTAACGT
4151  AACAAGTGCA ACAGGTACAA TTGGTGGTAC GATTTCCGGT AATACGGTAA
4201  ATGTTACGGC AAACGCTGGC GATTTAACAG TTGGGAATGG CGCAGAAATT
4251  AATGCGACAG AAGGAGCTGC AACCTTAACT ACATCATCGG GCAAATTAAC
4301  TACCGAAGCT AGTTCACACA TTACTTCAGC CAAGGGTCAG GTAAATCTTT
4351  CAGCTCAGGA TGGTAGCGTT GCAGGAAGTA TTAATGCCGC CAATGTGACA
4401  CTAAATACTA CAGGCACTTT AACTACCGTG AAGGGTTCAA ACATTAATGC
4451  AACCAGCGGT ACCTTGGTTA TTAACGCAAA AGACGCTGAG CTAAATGGCG
4501  CAGCATTGGG TAACCACACA GTGGTAAATG CAACCAACGC AAATGGCTCC
4551  GGCAGCGTAA TCGCGACAAC CTCAAGCAGA GTGAACATCA CTGGGGATTT
4601  AATCACAATA AATGGATTAA ATATCATTTC AAAAAACGGT ATAAACACCG
4651  TACTGTTAAA AGGCGTTAAA ATTGATGTGA AATACATTCA ACCGGGTATA
4701  GCAAGCGTAG ATGAAGTAAT TGAAGCGAAA CGCATCCTTG AGAAGGTAAA
4751  AGATTTATCT GATGAAGAAA GAGAAGCGTT AGCTAAACTT GGAGTAAGTG
4801  CTGTACGTTT TATTGAGCCA AATAATACAA TTACAGTCGA TACACAAAAT
```

FIG.1G.

```
4851  GAATTTGCAA CCAGACCATT AAGTCGAATA GTGATTTCTG AAGGCAGGGC
4901  GTGTTTCTCA AACAGTGATG GCGCGACGGT GTGCGTTAAT ATCGCTGATA
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATG
```

FIG. 2A. AMINO ACID SEQUENCE OF HIGH MOLECULAR WEIGHT PROTEIN I

```
  1 MNKIYRLKFS KRLNALVAVS ELARGCDHST EKGSEKPARM KVRHLALKPL
 51 SAMLLSLGVT SIPQSVLASG LQGMDVVHGT ATMQVDGNKT IIRNSVDAII
101 NWKQFNIDQN EMVQFLQENN NSAVFNRVTS NQISQLKGIL DSNGQVFLIN
151 PNGITIGKDA IINTNGFTAS TLDISNENIK ARNFTFEQTK DKALAEIVNH
201 GLITVGKDGS VNLIGGKVKN EGVISVNGGS ISLLAGQKIT ISDIINPTIT
251 YSIAAPENEA VNLGDIFAKG GNINVRAATI RNQGKLSADS VSKDKSGNIV
301 LSAKEGEAEI GGVISAQNQQ AKGGKLMITG DKVTLKTGAV IDLSGKEGGE
351 TYLGGDERGE GKNGIQLAKK TSLEKGSTIN VSGKEKGGRA IVWGDIALID
401 GNINAQGSGD IAKTGGFVET SGHDLFIKDN AIVDAKEWLL DFDNVSINAE
451 TAGRSNTSED DEYTGSGNSA STPKRNKEKT TLTNTTLESI LKKGTFVNIT
501 ANQRIYVNSS INLSNGSLTL WSEGRSGGGV EINNDITTGD DTRGANLTIY
551 SGGWVDVHKN ISLGAQGNIN ITAKQDIAFE KGSNQVITGQ GTITSGNQKG
601 FRFNNVSLNG TGSGLQFTTK RTNKYAITNK FEGTLNISGK VNISMVLPKN
651 ESGYDKFKGR TYWNLTSLNV SESGEFNLTI DSRGSDSAGT LTQPYNLNGI
701 SFNKDTTFNV ERNARVNFDI KAPIGINKYS SLNYASFNGN ISVSGGGSVD
```

FIG.2B.

```
751   FTLLASSSNV QTPGVVINSK YFNVSTGSSL RFKTSGSTKT GFSIEKDLTL
801   NATGGNITLL QVEGTDGMIG KGIVAKKNIT FEGGNITFGS RKAVTEIEGN
851   VTINNNANVT LIGSDFDNHQ KPLTIKKDVI INSGNLTAGG NIVNIAGNLT
901   VESNANFKAI TNFTFNVGGL FDNKGNSNIS IAKGGARFKD IDNSKNLSIT
951   TNSSSTYRTI ISGNITNKNG DLNITNEGSD TEMQIGGDVS QKEGNLTISS
1001  DKINITKQIT IKAGVDGENS DSDATNNANL TIKTKELKLT QDLNISGFNK
1051  AEITAKDGSD LTIGNTNSAD GTNAKKVTFN QVKDSKISAD GHKVTLHSKV
1101  ETSGSNNNTE DSSDNNAGLT IDAKNVTVNN NITSHKAVSI SATSGEITTK
1151  TGTTINATTG NVEITAQTGS ILGGIESSSG SVTLTATEGA LAVSNISGNT
1201  VTVTANSGAL TTLAGSTIKG TESVTTSSQS GDIGGTISGG TVEVKATESL
1251  TTQSNSKIKA TTGEANVTSA TGTIGGTISG NTVNVTANAG DLTVGNGAEI
1301  NATEGAATLT TSSGKLTTEA SSHITSAKGQ VNLSAQDGSV AGSINAANVT
1351  LNTTGTLTTV KGSNINATSG TLVINAKDAE LNGAALGNHT VVNATNANGS
1401  GSVIATTSSR VNITGDLITI NGLNIISKNG INTVLLKGVK IDVKYIQPGI
1451  ASVDEVIEAK RILEKVKDLS DEEREALAKL GVSAVRFIEP NNTITVDTQN
1501  EFATRPLSRI VISEGRACFS NSDGATVCVN IADNGR
```

FIG. 3A. AMINO ACID SEQUENCE OF HIGH MOLECULAR WEIGHT PROTEIN II (HMW2)

```
  1 TAAATATACA AGATAATAAA AATAAATCAA GATTTTTGTG ATGACAAACA
 51 ACAATTACAA CACCTTTTTT GCAGTCTATA TGCAAATATT TTAAAAAAAT
101 AGTATAAATC CGCCATATAA AATGGTATAA TCTTTCATCT TTCATCTTTA
151 ATCTTTCATC TTTCATCTTT CATCTTTCAT CTTTCATCTT TCATCTTTCA
201 TCTTTCATCT TTCATCTTTC ATCTTTCATC TTTCATCTTT CACATGAAAT
251 GATGAACCGA GGGAAGGGAG GGAGGGGCAA GAATGAAGAG GGAGCTGAAC
301 GAACGCAAAT GATAAAGTAA TTTAATTGTT CAACTAACCT TAGGAGAAAA
351 TATGAACAAG ATATATCGTC TCAAATTCAG CAAACGCCTG AATGCTTTGG
401 TTGCTGTGTC TGAATTGGCA CGGGGTTGTG ACCATTCCAC AGAAAAAGGC
451 TTCCGCTATG TTACTATCTT TAGGTGTAAC CACTTAGCGT TAAAGCCACT
501 TTCCGCTATG TTACTATCTT TAGGTGTAAC ATCTATTCCA CAATCTGTTT
551 TAGCAAGCGG CTTACAAGGA ATGGATGTAG TACACGGCAC AGCCACTATG
601 CAAGTAGATG GTAATAAAAC CATTATCCGC AACAGTGTTG ACGCTATCAT
651 TAATTGGAAA CAATTTAACA TCGACCAAAA TGAAATGGTG CAGTTTTTAC
701 AAGAAAACAA CAACTCCGCC GTATTCAACC GTGTTACATC TAACCAAATC
```

FIG.3B.

```
751   TCCCAATTAA AAGGGATTTT AGATTCTAAC GGACAAGTCT TTTTAATCAA
801   CCCAAATGGT ATCACAATAG GTAAAGACGC AATTATTAAC ACTAATGGCT
851   TTACGGCTTC TACGCTAGAC ATTTCTAACG AAAACATCAA GGCGCGTAAT
901   TTCACCTTCG AGCAAACCAA AGATAAAGCG CTCGCTGAAA TTGTGAATCA
951   CGGTTTAATT ACTGTCGGTA AAGACGGCAG TGTAAATCTT ATTGGTGGCA
1001  AAGTGAAAAA CGAGGGTGTG ATTAGCGTAA ATGGTGGCAG CATTTCTTTA
1051  CTCGCAGGGC AAAAAATCAC CATCAGCGAT ATAATAAACC CAACCATTAC
1101  TTACAGCATT GCCGCGCCTG AAAATGAAGC GGTCAATCTG GGCGATATTT
1151  TTGCCAAAGG CGGTAACATT AATGTCCGTG CTGCCACTAT TCGAAACCAA
1201  GGTAAACTTT CTGCTGATTC TGTAAGCAAA GATAAAAGCG GCAATATTGT
1251  TCTTTCCGCC AAAGAGGGTG AAGCGGAAAT TGGCGGTGTA ATTTCCGCTC
1301  AAAATCAGCA AGCTAAAGGC GGCAAGCTGA TGATTACAGG CGATAAAGTC
1351  ACATTAAAAA CAGGTGCAGT TATCGACCTT TCAGGTAAAG AAGGGGGAGA
1401  AACTTACCTT GGCGGTGACG AGCGCGGCGA AGGTAAAAAC GGCATTCAAT
1451  TAGCAAAGAA AACCTCTTTA GAAAAAGGCT CAACCATCAA TGTATCAGGC
1501  AAAGAAAAAG GCGGACGCGC TATTGTGTGG GGCGATATTG CGTTAATTGA
```

FIG. 3C.

```
1551  CGGCAATATT AACGCTCAAG GTAGTGGTGA TATCGCTAAA ACCGGTGGTT
1601  TTGTGGAGAC ATCGGGGCAT TATTTATCCA TTGACAGCAA TGCAATTGTT
1651  AAAACAAAAG AGTGGTTGCT AGACCCTGAT GATGTAACAA TTGAAGCCGA
1701  AGACCCCCTT CGCAATAATA CCGGTATAAA TGATGAATTC CCAACAGGCA
1751  CCGGTGAAGC AAGCGACCCT AAAAAAAATA GCGAACTCAA AACAACGCTA
1801  ACCAATACAA CTATTTCAAATTATCTGAAA AACGCCTGGA CAATGAATAT
1851  AACGGCATCA AGAAAACTTA CCGTTAATAG CTCAATCAAC ATCGGAAGCA
1901  ACTCCCACTT AATTCTCCAT AGTAAAGGTC AGCGTGGCGG AGGCGTTCAG
1951  ATTGATGGAG ATATTACTTC TAAAGGCGGA AATTTAACCA TTTATTCTGG
2001  CGGATGGGTT GATGTTCATA AAAATATTAC GCTTGATCAG GGTTTTTTAA
2051  ATATTACCGC CGCTTCCGTA GCTTTTGAAG GTGGAAATAA CAAAGCACGC
2101  GACGCGGCAA ATGCTAAAAT TGTCGCCCAG GGCACTGTAA CCATTACAGG
2151  AGAGGGAAAA GATTTCAGGG CTAACAACGT ATCTTTAAAC GGAACGGGTA
2201  AAGGTCTGAA TATCATTTCA TCAGTGAATA ATTTAACCCA CAATCTTAGT
2251  GGCACAATTA ACATATCTGG GAATATAACA ATTAACCAAA CTACGAGAAA
2301  GAACACCTCG TATTGGCAAA CCAGCCATGA TTCGCACTGG AACGTCAGTG
2351  CTCTTAATCT AGAGACAGGC GCAAATTTTA CCTTTATTAA ATACATTTCA
```

FIG. 3D.

```
2401  AGCAATAGCA AAGGCTTAAC AACACAGTAT AGAAGCTCTG CAGGGGTGAA
2451  TTTTAACGGC GTAAATGGCA ACATGTCATT CAATCTCAAA GAAGGAGCGA
2501  AAGTTAATTT CAAATTAAAA CCAAACGAGA ACATGAACAC AAGCAAACCT
2551  TTACCAATTC GGTTTTTAGC CAATATCACA GCCACTGGTG GGGGCTCTGT
2601  TTTTTTTGAT ATATATGCCA ACCATTCTGG CAGAGGGGCT GAGTTAAAAA
2651  TGAGTGAAAT TAATATCTCT AACGGCGCTA ATTTTACCTT AAATTCCCAT
2701  GTTCGCGGCG ATGACGCTTT TAAAATCAAC AAAGACTTAA CCATAAATGC
2751  AACCAATTCA AATTTCAGCC TCAGACAGAC GAAAGATGAT TTTTATGACG
2801  GGTACGCACG CAATGCCATC AATTCAACCT ACAACATATC CATTCTGGGC
2851  GGTAATGTCA CCCTTGGTGG ACAAAACTCA AGCAGCAGCA TTACGGGGAA
2901  TATTACTATC GAGAAAGCAG CAAATGTTAC GCTAGAAGCC AATAACGCCC
2951  CTAATCAGCA AAACATAAGG GATAGAGTTA TAAAACTTGG CAGCTTGCTC
3001  GTTAATGGGA GTTTAAGTTT AACTGGCGAA AATGCAGATA TTAAAGGCAA
3051  TCTCACTATT TCAGAAAGCG CCACTTTTAA AGGAAAGACT AGAGATACCC
3101  TAAATATCAC CGGCAATTTT ACCAATAATG GCACTGCCGA AATTAATATA
3151  ACACAAGGAG TGGTAAAACT TGGCAATGTT ACCAATGATG GTGATTTAAA
```

FIG.3E.

```
3201  CATTACCACT CACGCTAAAC GCAACCAAAG AAGCATCATC GGCGGAGATA
3251  TAATCAACAA AAAAGGAAGC TTAAATATTA CAGACAGTAA TAATGATGCT
3301  GAAATCCAAA TTGGCGGCAA TATCTCGCAA AAAGAAGGCA ACCTCACGAT
3351  TTCTTCCGAT AAAATTAATA TCACCAAACA GATAACAATC AAAAAGGGTA
3401  TTGATGGAGA GGACTCTAGT TCAGATGCGA CAAGTAATGC CAACCTAACT
3451  ATTAAAACCA AAGAATTGAA ATTGACAGAA GACCTAAGTA TTTCAGGTTT
3501  CAATAAAGCA GAGATTACAG CCAAAGATGG TAGAGATTTA ACTATTGGCA
3551  ACAGTAATGA CGGTAACAGC GGTGCCGAAG CCAAAACAGT AACTTTTAAC
3601  AATGTTAAAG ATTCAAAAAT CTCTGCTGAC GGTCACAATG TGACACTAAA
3651  TAGCAAAGTG AAAACATCTA GCAGCAATGG CGGACGTGAA AGCAATAGCG
3701  ACAACGATAC CGGCTTAACT ATTACTGCAA AAAATGTAGA AGTAAACAAA
3751  GATATTACTT CTCTCAAAAC AGTAAATATC ACCGCGTCGG AAAAGGTTAC
3801  CACCACAGCA GGCTCGACCA TTAACGCAAC AAATGGCAAA GCAAGTATTA
3851  CAACCAAAAC AGGTGATATC AGCGGTACGA TTTCCGGTAA CACGGTAAGT
3901  GTTAGCGCGA CTGGTGATTT AACCACTAAA TCCGGCTCAA AAATTGAAGC
3951  GAAATCGGGT GAGGCTAATG TAACAAGTGC AACAGGTACA ATTGGCGGTA
```

FIG.3F.

```
4001  CAATTTCCGG TAATACGGTA AATGTTACGG CAAACGCTGG CGATTTAACA
4051  GTTGGGAATG GCGCAGAAAT TAATGCGACA GAAGGAGCTG CAACCTTAAC
4101  CGCAACAGGG AATACCTTGA CTACTGAAGC CGGTTCTAGC ATCACTTCAA
4151  CTAAGGGTCA GGTAGACCTC TTGGCTCAGA ATGGTAGCAT CGCAGGAAGC
4201  ATTAATGCTG CTAATGTGAC ATTAAATACT ACAGGCACCT TAACCACCGT
4251  GGCAGGCTCG GATATTAAAG CAACCAGCGG CACCTTGGTT ATTAACGCAA
4301  AAGATGCTAA GCTAAATGGT GATGCATCAG GTGATAGTAC AGAAGTGAAT
4351  GCAGTCAACG CAAGCGGCTC TGGTAGTGTG ACTGCGGCAA CCTCAAGCAG
4401  TGTGAATATC ACTGGGGATT TAAACACAGT AAATGGGTTA AATATCATTT
4451  CGAAAGATGG TAGAAACACT GTGCGCTTAA GAGGCAAGGA AATTGAGGTG
4501  AAATATATCC AGCCAGGTGT AGCAAGTGTA GAAGAAGTAA TTGAAGCGAA
4551  ACGCGTCCTT GAAAAAGTAA AAGATTTATC TGATGAAGAA AGAGAAACAT
4601  TAGCTAAACT TGGTGTAAGT GCTGTACGTT TTGTTGAGCC AAATAATACA
4651  ATTACAGTCA ATACACAAAA TGAATTTACA ACCAGACCGT CAAGTCAAGT
4701  GATAATTTCT GAAGGTAAGG CGTGTTTCTC AAGTGGTAAT GGCGCACGAG
4751  TATGTACCAA TGTTGCTGAC GATGGACAGC CGTAGTCAGT AATTGACAAG
4801  GTAGATTTCA TCCTGCAATG AAGTCATTTT ATTTTCGTAT TATTTACTGT
```

FIG.3G.

```
4851  GTGGGTTAAA GTTCAGTACG GGCTTTACCC ATCTTGTAAA AAATTACGGA
4901  GAATACAATA AAGTATTTTT AACAGGTTAT TATTATG
```

FIG. 4A. AMINO ACID SEQUENCE OF HIGH MOLECULAR WEIGHT PROTEIN 2

```
  1  MNKIYRLKFS KRLNALVAVS ELARGCDHST EKGSEKPARM KVRHLALKPL
 51  SAMLLSLGVT SIPQSVLASG LQGMDVVHGT ATMQVDGNKT IIRNSVDAII
101  NWKQFNIDQN EMVQFLQENN NSAVFNRVTS NQISQLKGIL DSNGQVFLIN
151  PNGITIGKDA IINTNGFTAS TLDISNENIK ARNFTFEQTK DKALAEIVNH
201  GLITVGKDGS VNLIGGKVKN EGVISVNGGS ISLLAGQKIT ISDIINPTIT
251  YSIAAPENEA VNLGDIFAKG GNINVRAATI RNQGKLSADS VSKDKSGNIV
301  LSAKEGEAEI GGVISAQNQQ AKGGKLMITG DKVTLKTGAV IDLSGKEGGE
351  TYLGGDERGE GKNGIQLAKK TSLEKGSTIN VSGKEKGGRA IVWGDIALID
401  GNINAQGSGD IAKTGGFVET SGHDLFIKDN AIVDAKEWLL DFDNVSINAE
451  DPLRNNTGIN DEFPTGTGEA SDPKKNSELK TTLTNTTISN YLKNAWTMNI
501  TASRKLTVNS SINIGSNSHL ILHSKGQRGG GVQIDGDITS KGGNLTIYSG
551  GWVDVHKNIT LDQGFLNITA ASVAFEGGNN KARDAANAKI VAQGTVTITG
601  EGKDFRANNV SLNGTGKGLN IISSVNNLTH NLSGTINISG NITINQTTRK
651  NTSYWQTSHD SHWNVSALNL ETGANFTFIK YISSNSKGLT TQYRSSAGVN
701  FNGVNGNMSF NLKEGAKVNF KLKPNENMNT SKPLPIRFLA NITATGGGSV
```

FIG.4B.

```
 751 FFDIYANHSG RGAELKMSEI NISNGANFTL NSHVRGDDAF KINKDLTINA
 801 TNSNFSLRQT KDDFYDGYAR NAINSTYNIS ILGGNVTLGG QNSSSSITGN
 851 ITIEKAANVT LEANNAPNQQ NIRDRVIKLG SLLVNGSLSL TGENADIKGN
 901 LTISESATFK GKTRDTLNIT GNFTNNGTAE INITQGVVKL GNVTNDGDLN
 951 ITTHAKRNQR SIIGGDIINK KGSLNITDSN NDAEIQIGGN ISQKEGNLTI
1001 SSDKINITKQ ITIKKGIDGE DSSSDATSNA NLTIKTKELK LTEDLSISGF
1051 NKAEITAKDG RDLTIGNSND GNSGAEAKTV TFNNVKDSKI SADGHNVTLN
1101 SKVKTSSSNG GRESNSDNDT GLTITAKNVE VNKDITSLKT VNITASEKVT
1151 TTAGSTINAT NGKASITTKT GDISGTISGN TVSVSATVDL TTKSGSKIEA
1201 KSGEANVTSA TGTIGGTISG NTVNVTANAG DLTVGNGAEI NATEGAATLT
1251 ATGNTLTTEA GSSITSTKGQ VDLLAQNGSI AGSINAANVT LNTTGTLTTV
1301 AGSDIKATSG TLVINAKDAK LNGDASGDST EVNAVNASGS GSVTAATSSS
1351 VNITGDLNTV NGLNIISKDG RNTVRLRGKE IEVKYIQPGV ASVEEVIEAK
1401 RVLEKVKDLS DEERETLAKL GVSAVRFVEP NNTITVNTQN EFTTRPSSQV
1451 IISEGKACFS SGNGARVCTN VADDGQP
```

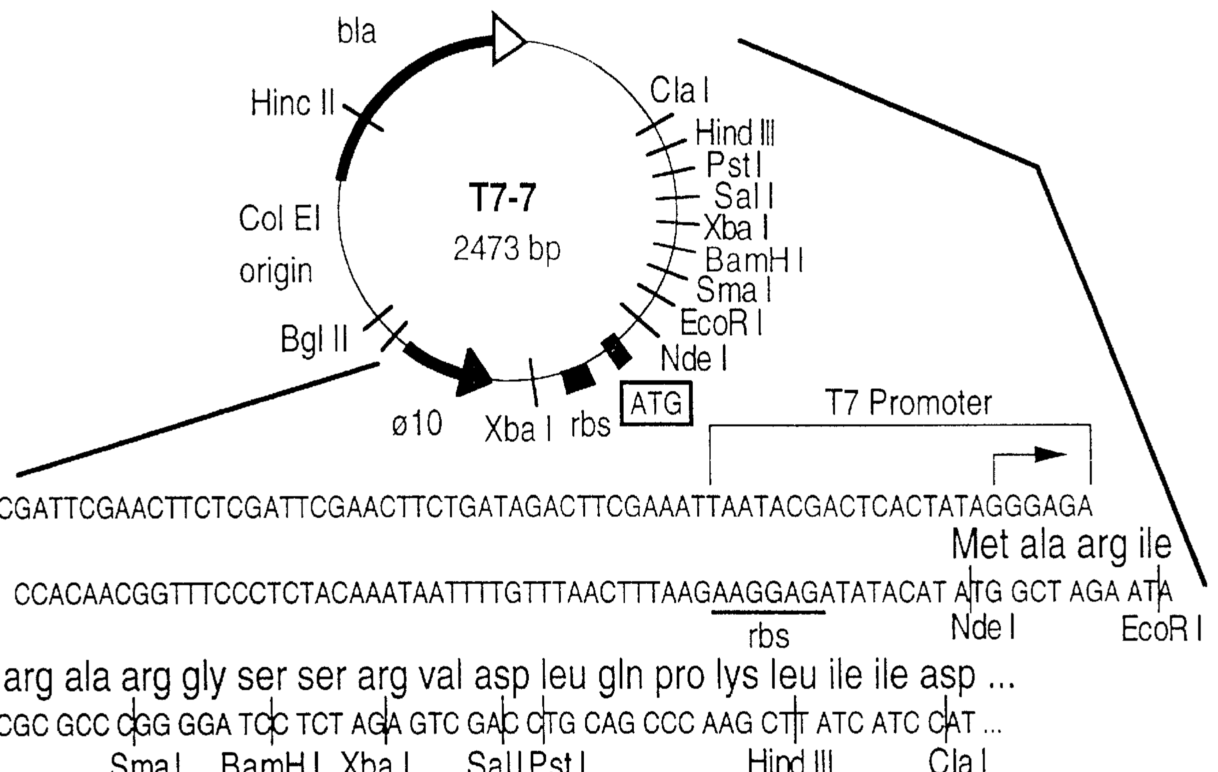

FIG. 5B.

(A) Partial restriction maps of representative HMW1 and HMW2 recombinant phage and of HMW1 plasmid subclones. The shaded boxes indicate the locations of the structural genes. In the recombinant phage, transcription proceeds from left to right for the HMW1 gene and from right to left for the HMW2 gene. The methods used for construction of the plasmids shown are described in the text. (B) Restriction map of the T7 expression vector pT7-7. This vector contains the T7 RNA polymerase promoter $\phi$10, a ribosome - binding site (rbs), and the translational start site for the T7 gene 10 protein upstream from a multiple cloning site (37).

FIG. 6A.

```
  1 ACAGCGTTCT CTTAATACTA GTACAAACCC ACAATAAAAT ATGACAAACA
 51 ACAATTACAA CACCTTTTTT GCAGTCTATA TGCAAATATT TTAAAAAATA
101 GTATAAATCC GCCATATAAA ATGGTATAAT CTTTCATCTT TCATCTTTCA
151 TCTTTCATCT TTCATCTTTC ATCTTTCATC TTTCATCTTT CATCTTTCAT
201 CTTTCATCTT TCATCTTTCA TCTTTCATCT TTCATCTTTC ACATGAAATG
251 ATGAACCGAG GGAAGGGAGG GAGGGGCAAG AATGAAGAGG GAGCTGAACG
301 AACGCAAATG ATAAAGTAAT TTAATTGTTC AACTAACCTT AGGAGAAAAT
351 ATGAACAAGA TATATCGTCT CAAATTCAGC AAACGCCTGA ATGCTTTGGT
401 TGCTGTGTCT GAATTGGCAC GGGGTTGTGA CCATTCCACA GAAAAAGGCA
451 GCGAAAAACC TGCTCGCATG AAAGTGCGTC ACTTAGCGTT AAAGCCACTT
501 TCCGCTATGT TACTATCTTT AGGTGTAACA TCTATTCCAC AATCTGTTTT
551 AGCAAGCGGC TTACAAGGAA TGGATGTAGT ACACGGCACA GCCACTATGC
601 AAGTAGATGG TAATAAAACC ATTATCCGCA ACAGTGTTGA CGCTATCATT
651 AATTGGAAAC AATTTAACAT CGACCAAAAT GAAATGGTGC AGTTTTTACA
701 AGAAAACAAC AACTCCGCCG TATTCAACCG TGTTACATCT AACCAAATCT
751 CCCAATTAAA AGGGATTTTA GATTCTAACG GACAAGTCTT TTTAATCAAC
```

FIG.6B.

```
 801  CCAAATGGTA TCACAATAGG TAAAGACGCA ATTATTAACA CTAATGGCTT
 851  TACGGCTTCT ACGCTAGACA TTTCTAACGA AAACATCAAG GCGCGTAATT
 901  TCACCTTCGA GCAAACCAAA GATAAAGCGC TCGCTGAAAT TGTGAATCAC
 951  GGTTTAATTA CTGTCGGTAA AGACGGCAGT GTAAATCTTA TTGGTGGCAA
1001  AGTGAAAAAC GAGGGTGTGA TTAGCGTAAA TGGTGGCAGC ATTTCTTTAC
1051  TCGCAGGGCA AAAAATCACC ATCAGCGATA TAATAAACCC AACCATTACT
1101  TACAGCATTG CCGCGCCTGA AAATGAAGCG GTCAATCTGG GCGATATTTT
1151  TGCCAAAGGC GGTAACATTA ATGTCCGTGC TGCCACTATT CGAAACCAAG
1251  CTTTCCGCCA AAGAGGGTGA AGCGGAAATT GGCGGTGTAA TTTCCGCTCA
1301  AAATCAGCAA GCTAAAGGCG GCAAGCTGAT GATTACAGGC GATAAAGTCA
1351  CATTAAAAAC AGGTGCAGTT ATCGACCTTT CAGGTAAAGA AGGGGGAGAA
1401  ACTTACCTTG GCGGTGACGA GCGCGGCGAA GGTAAAAACG GCATTCAATT
1451  AGCAAAGAAA ACCTCTTTAG AAAAAGGCTC AACCATCAAT GTATCAGGCA
1501  AAGAAAAAGG CGGACGCGCT ATTGTGTGGG GCGATATTGC GTTAATTGAC
1551  GGCAATATTA ACGCTCAAGG TAGTGGTGAT ATCGCTAAAA CCGGTGGTTT
1601  TGTGGAGACG TCGGGGCATG ATTTATTCAT CAAAGACAAT GCAATTGTTG
```

FIG. 6C.

```
1651  ACGCCAAAGA GTGGTTGTTA GACCCGGATA ATGTATCTAT TAATGCAGAA
1701  ACAGCAGGAC GCAGCAATAC TTCAGAAGAC GATGAATACA CGGGATCCGG
1751  GAATAGTGCC AGCACCCCAA AACGAAACAA AGAAAAGACA ACATTAACAA
1801  ACACAACTCT TGAGAGTATA CTAAAAAAAG GTACCTTTGT TAACATCACT
1851  GCTAATCAAC GCATCTATGT CAATAGCTCC ATTAATTTAT CCAATGGCAG
1901  CTTAACTCTT TGGAGTGAGG GTCGGAGCGG TGGCGGCGTT GAGATTAACA
1951  ACGATATTAC CACCGGTGAT GATACCAGAG GTGCAAACTT AACAATTTAC
2001  TCAGGCGGCT GGGTTGATGT TCATAAAAAT ATCTCACTCG GGGCGCAAGG
2051  TAACATAAAC ATTACAGCTA AACAAGATAT CGCCTTTGAG AAAGGAAGCA
2101  ACCAAGTCAT TACAGGTCAA GGGACTATTA CCTCAGGCAA TCAAAAAGGT
2151  TTTAGATTTA ATAATGTCTC TCTAAACGGC ACTGGCAGCG GACTGCAATT
2201  CACCACTAAA AGAACCAATA AATACGCTAT CACAAATAAA TTTGAAGGGA
2251  CTTTAAATAT TTCAGGGAAA GTGAACATCT CAATGGTTTT ACCTAAAAAT
2301  GAAAGTGGAT ATGATAAATT CAAAGGACGC ACTTACTGGA ATTTAACCTC
2351  GAAAGTGGAT ATGATAAATT CAAAGGACGC CCTCACTATT GACTCCAGAG
2401  GAAGCGATAG TGCAGGCACA CTTACCCAGC CTTATAATTT AAACGGTATA
2451  TCATTCAACA AAGACACTAC CTTTAATGTT GAACGAAATG CAAGAGTCAA
```

FIG.6D.

| | | | | | |
|---|---|---|---|---|---|
| 2501 | CTTTGACATC | AAGGCACCAA | TAGGGATAAA | TAAGTATTCT | AGTTTGAATT |
| 2551 | ACGCATCATT | TAATGGAAAC | ATTTCAGTTT | CGGGAGGGGG | GAGTGTTGAT |
| 2601 | TTCACACTTC | TCGCCTCATC | CTCTAACGTC | CAAACCCCCG | GTGTAGTTAT |
| 2651 | AAATTCTAAA | TACTTTAATG | TTTCAACAGG | GTCAAGTTTA | AGATTTAAAA |
| 2701 | CTTCAGGCTC | AACAAAAACT | GGCTTCTCAA | TAGAGAAAGA | TTTAACTTTA |
| 2751 | AATGCCACCG | GAGGCAACAT | AACACTTTTG | CAAGTTGAAG | GCACCGATGG |
| 2801 | AATGATTGGT | AAAGGCATTG | TAGCCAAAAA | AAACATAACC | TTTGAAGGAG |
| 2851 | GTAAGATGAG | GTTTGGCTCC | AGGAAAGCCG | TAACAGAAAT | CGAAGGCAAT |
| 2901 | GTTACTATCA | ATAACAACGC | TAACGTCACT | CTTATCGGTT | CGGATTTTGA |
| 2951 | CAACCATCAA | AAACCTTTAA | CTATTAAAAA | AGATGTCATC | ATTAATAGCG |
| 3001 | GCAACCTTAC | CGCTGGAGGC | AATATTGTCA | ATATAGCCGG | AAATCTTACC |
| 3051 | GTTGAAAGTA | ACGCTAATTT | CAAAGCTATC | ACAAATTTCA | CTTTTAATGT |
| 3101 | AGGCGGCTTG | TTTGACAACA | AAGGCAATTC | AAATATTTCC | ATTGCCAAAG |
| 3151 | GAGGGGCTCG | CTTTAAAGAC | ATTGATAATT | CCAAGAATTT | AAGCATCACC |
| 3201 | ACCAACTCCA | GCTCCACTTA | CCGCACTATT | ATAAGCGGCA | ATATAACCAA |
| 3251 | TAAAAACGGT | GATTTAAATA | TTACGAACGA | AGGTAGTGAT | ACTGAAATGC |

FIG.6E.

```
3301  AAATTGGCGG CGATGTCTCG CAAAAAGAAG GTAATCTCAC GATTTCTTCT
3351  GACAAAATCA ATATTACCAA ACAGATAACA ATCAAGGCAG GTGTTGATGG
3401  GGAGAATTCC GATTCAGACG CGACAAACAA TGCCAATCTA ACCATTAAAA
3451  CCAAAGAATT GAAATTAACG CAAGACCTAA ATATTTCAGG TTTCAATAAA
3501  GCAGAGATTA CAGCTAAAGA TGGTAGTGAT TTAACTATTG GTAACACCAA
3551  TAGTGCTGAT GGTACTAATG CCAAAAAAGT AACCTTTAAC CAGGTTAAAG
3601  ATTCAAAAAT CTCTGCTGAC GGTCACAAGG TGACACTACA CAGCAAAGTG
3651  GAAACATCCG GTAGTAATAA CAACACTGAA GATAGCAGTG ACAATAATGC
3701  CGGCTTAACT ATCGATGCAA AAAATGTAAC AGTAAACAAC AATATTACTT
3751  CTCACAAAGC AGTGAGCATC TCTGCGACAA GTGGAGAAAT TACCACTAAA
3801  ACAGGTACAA CCATTAACGC AACCACTGGT AACGTGGAGA TAACCGCTCA
3851  AACAGGTAGT ATCCTAGGTG GAATTGAGTC CAGCTCTGGC TCTGTAACAC
3901  TTACTGCAAC CGAGGGCGCT CTTGCTGTAA GCAATATTTC GGGCAACACC
3951  GTTACTGTTA CTGCAAATAG CGGTGCATTA ACCACTTTGG CAGGCTCTAC
4001  AATTAAAGGA ACCGAGAGTG TAACCACTTC AAGTCAATCA GGCGATATCG
4051  GCGGTACGAT TTCTGGTGGC ACAGTAGAGG TTAAAGCAAC CGAAAGTTTA
```

FIG. 6F.

```
4101  ACCACTCAAT CCAATTCAAA AATTAAAGCA ACAACAGGCG AGGCTAACGT
4151  AACAAGTGCA ACAGGTACAA TTGGTGGTAC GATTTCCGGT AATACGGTAA
4201  ATGTTACGGC AAACGCTGGC GATTTAACAG TTGGGAATGG CGCAGAAATT
4251  AATGCGACAG AAGGAGCTGC AACCTTAACT ACATCATCGG GCAAATTAAC
4301  TACCGAAGCT AGTTCACACA TTACTTCAGC CAAGGGTCAG GTAAATCTTT
4351  CAGCTCAGGA TGGTAGCGTT GCAGGAAGTA TTAATGCCGC CAATGTGACA
4401  CTAAATACTA CAGGCACTTT AACTACCGTG AAGGGTTCAA ACATTAATGC
4451  AACCAGCGGT ACCTTGGTTA TTAACGCAAA AGACGCTGAG CTAAATGGCG
4501  CAGCATTGGG TAACCACACA GTGGTAAATG CAACCAACGC AAATGGCTCC
4551  GGCAGCGTAA TCGCGACAAC CTCAAGCAGA GTGAACATCA CTGGGGATTT
4601  AATCACAATA AATGGATTAA ATATCATTTC AAAAAACGGT ATAAACACCG
4651  TACTGTTAAA AGGCGTTAAA ATTGATGTGA AATACATTCA ACCGGGTATA
4701  GCAAGCGTAG ATGAAGTAAT TGAAGCGAAA CGCATCCTTG AGAAGGTAAA
4751  AGATTTATCT GATGAAGAAA GAGAAGCGTT AGCTAAACTT GGCGTAAGTG
4801  CTGTACGTTT TATTGAGCCA AATAATACAA TTACAGTCGA TACACAAAAT
4851  GAATTTGCAA CCAGACCATT AAGTCGAATA GTGATTTCTG AAGGCAGGGC
4901  GTGTTTCTCA AACAGTGATG GCGCGACGGT GTGCGTTAAT ATCGCTGATA
```

FIG.6G.

```
4951  ACGGGCGGTA GCGGTCAGTA ATTGACAAGG TAGATTTCAT CCTGCAATGA
5001  AGTCATTTTA TTTTCGTATT ATTTACTGTG TGGGTTAAAG TTCAGTACGG
5051  GCTTTACCCA TCTTGTAAAA AATTACGGAG AATACAATAA AGTATTTTTA
5101  ACAGGTTATT ATTATGAAAA ATATAAAAAG CAGATTAAAA CTCAGTGCAA
5151  TATCAGTATT GCTTGGCCTG GCTTCTTCAT CATTGTATGC AGAAGAAGCG
5201  TTTTTAGTAA AAGGCTTTCA GTTATCTGGT GCACTTGAAA CTTTAAGTGA
5251  AGACGCCCAA CTGTCTGTAG CAAAATCTTT ATCTAAATAC CAAGGCTCGC
5301  AAACTTTAAC AAACCTAAAA ACAGCACAGC TTGAATTACA GGCTGTGCTA
5351  GATAAGATTG AGCCAAATAA GTTTGATGTG ATATTGCCAC AACAAACCAT
5401  TACGGATGGC AATATTATGT TTGAGCTAGT CTCGAAATCA GCCGCAGAAA
5451  GCCAAGTTTT TTATAAGGCG AGCCAGGGTT ATAGTGAAGA AAATATCGCT
5501  CGTAGCCTGC CATCTTTGAA ACAAGGAAAA GTGTATGAAG ATGGTCGTCA
5551  GTGGTTCGAT TTGCGTGAAT TCAATATGGC AAAAGAAAAT CCACTTAAAG
5601  TCACTCGCGT GCATTACGAG TTAAACCCTA AAAACAAAAC CTCTGATTTG
5651  GTAGTTGCAG GTTTTTCGCC TTTTGGCAAA ACGCGTAGCT TTGTTTCCTA
5701  TGATAATTTC GGCGCAAGGG AGTTTAACTA TCAACGTGTA AGTCTAGGTT
```

FIG.6H.

```
5751  TTGTAAATGC CAATTTGACC GGACATGATG ATGTATTAAA TCTAAACGCA
5801  TTGACCAATG TAAAAGCACC ATCAAAATCT TATGCGGTAG GCATAGGATA
5851  TACTTATCCG TTTTATGATA AACACCAATC CTTAAGTCTT TATACCAGCA
5901  TGAGTTATGC TGATTCTAAT GATATCGACG GCTTACCAAG TGCGATTAAT
5951  CGTAAATTAT CAAAAGGTCA ATCTATCTCT GCGAATCTGA AATGGAGTTA
6001  TTATCTCCCG ACATTTAACC TTGGAATGGA AGACCAGTTT AAAATTAATT
6051  TAGGCTACAA CTACCGCCAT ATTAATCAAA CATCCGAGTT AAACACCCTG
6101  GGTGCAACGA AGAAAAAATT TGCAGTATCA GGCGTAAGTG CAGGCATTGA
6151  TGGACATATC CAATTTACCC CTAAAACAAT CTTTAATATT GATTTAACTC
6201  ATCATTATTA CGCGAGTAAA TTACCAGGCT CTTTTGGAAT GGAGCGCATT
6251  GGCGAAACAT TTAATCGCAG CTATCACATT AGCACAGCCA GTTTAGGGTT
6301  GAGTCAAGAG TTTGCTCAAG GTTGGCATTT TAGCAGTCAA TTATCGGGTC
6351  AGTTTACTCT ACAAGATATA AGTAGCATAG ATTTATTCTC TGTAACAGGT
6401  ACTTATGGCG TCAGAGGCTT TAAATACGGC GGTGCAAGTG GTGAGCGCGG
6451  TCTTGTATGG CGTAATGAAT TAAGTATGCC AAAATACACC CGCTTTCAAA
6501  TCAGCCCTTA TGCGTTTTAT GATGCAGGTC AGTTCCGTTA TAATAGCGAA
6551  AATGCTAAAA CTTACGGCGA AGATATGCAC ACGGTATCCT CTGCGGGTTT
```

FIG. 6I.

```
6601   AGGCATTAAA  ACCTCTCCTA  CACAAAACTT  AAGCTTAGAT  GCTTTTGTTG
6651   CTCGTCGCTT  TGCAAATGCC  AATAGTGACA  ATTTGAATGG  CAACAAAAAA
6701   CGCACAAGCT  CACCTACAAC  CTTCTGGGGT  AGATTAACAT  TCAGTTTCTA
6751   ACCCTGAAAT  TTAATCAACT  GGTAAGCGTT  CCGCCTACCA  GTTTATAACT
6801   ATATGCTTTA  CCCGCCAATT  TACAGTCTAT  ACGCAACCCT  GTTTTCATCC
6851   TTATATATCA  AACAAACTAA  GCAAACCAAG  CAAACCAAGC  AAACCAAGCA
6901   AACCAAGCAA  ACCAAGCAAA  CCAAGCAAAC  CAAGCAAACC  AAGCAAACCA
6951   AGCAAACCAA  GCAAACCAAG  CAAACCAAGC  AAACCAAGCA  ATGCTAAAAA
7001   ACAATTTATA  TGATAAACTA  AAACATACTC  CATACCATGG  CAATACAAGG
7051   GATTTAATAA  TATGACAAAA  GAAAATTTAC  AAAGTGTTCC  ACAAAATACG
7101   ACCGCTTCAC  TTGTAGAATC  AAACAACGAC  CAAACTTCCC  TGCAAATACT
7151   TAAACAACCA  CCCAAACCCA  ACCTATTACG  CCTGGAACAA  CATGTCGCCA
7201   AAAAAGATTA  TGAGCTTGCT  TGCCGCGAAT  TAATGGCGAT  TTTGGAAAAA
7251   ATGGACGCTA  ATTTTGGAGG  CGTTCACGAT  ATTGAATTTG  ACGCACCTGC
7301   TCAGCTGGCA  TATCTACCCG  AAAAACTACT  AATTCATTTT  GCCACTCGTC
7351   TCGCTAATGC  AATTACAACA  CTCTTTTCCG  ACCCCGAATT  GGCAATTTCC
```

FIG. 6J.

```
7401  GAAGAAGGGG CATTAAAGAT GATTAGCCTG CAACGCTGGT TGACGCTGAT
7451  TTTTGCCTCT TCCCCCTACG TTAACGCAGA CCATATTCTC AATAAATATA
7501  ATATCAACCC AGATTCCGAA GGTGGCTTTC ATTTAGCAAC AGACAACTCT
7551  TCTATTGCTA AATTCTGTAT TTTTTACTTA CCCGAATCCA ATGTCAATAT
7601  GAGTTTAGAT GCGTTATGGG CAGGGAATCA ACAACTTTGT GCTTCATTGT
7651  GTTTTGCGTT GCAGTCTTCA CGTTTTATTG GTACTGCATC TGCGTTTCAT
7701  AAAAGAGCGG TGGTTTTACA GTGGTTTCCT AAAAAACTCG CCGAAATTGC
7751  TAATTTAGAT GAATTGCCTG CAAATATCCT TCATGATGTA TATATGCACT
7801  GCAGTTATGA TTTAGCAAAA AACAAGCACG ATGTTAAGCG TCCATTAAAC
7851  GAACTTGTCC GCAAGCATAT CCTCACGCAA GGATGGCAAG ACCGCTACCT
7901  TTACACCTTA GGTAAAAAGG ACGGCAAACC TGTGATGATG GTACTGCTTG
7951  AACATTTTAA TTCGGGACAT TCGATTTATC GCACGCATTC AACTTCAATG
8001  ATTGCTGCTC GAGAAAAATT CTATTTAGTC GGCTTAGGCC ATGAGGGCGT
8051  TGATAACATA GGTCGAGAAG TGTTTGACGA GTTCTTTGAA ATCAGTAGCA
8101  ATAATATAAT GGAGAGACTG TTTTTTATCC GTAAACAGTG CGAAACTTTC
8151  CAACCCGCAG TGTTCTATAT GCCAAGCATT GGCATGGATA TTACCACGAT
```

FIG.6K.

```
8201   TTTTGTGAGC AACACTCGGC TTGCCCCTAT TCAAGCTGTA GCCTTGGGTC
8251   ATCCTGCCAC TACGCATTCT GAATTTATTG ATTATGTCAT CGTAGAAGAT
8301   GATTATGTGG GCAGTGAAGA TTGTTTAGC  GAAACCCTTT TACGCTTACC
8351   CAAAGATGCC CTACCTTATG TACCATCTGC ACTCGCCCCA CAAAAAGTGG
8401   ATTATGTACT CAGGGAAAAC CCTGAAGTAG TCAATATCGG TATTGCCGCT
8451   ACCACAATGA AATTAAACCC TGAATTTTTG CTAACATTGC AAGAAATCAG
8501   AGATAAAGCT AAAGTCAAAA TACATTTTCA TTTCGCACTT GGACAATCAA
8551   CAGGCTTGAC ACACCCTTAT GTCAAATGGT TTATCGAAAG CTATTTAGGT
8601   GACGATGCCA CTGCACATCC CCACGCACCT TATCACGATT ATCTGGCAAT
8651   ATTGCGTGAT TGCGATATGC TACTAAATCC GTTTCCTTTC GGTAATACTA
8701   ACGGCATAAT TGATATGGTT ACATTAGGTT TAGTTGGTGT ATGCAAAACG
8751   GGGGATGAAG TACATGAACA TATTGATGAA GGTCTGTTTA AACGCTTAGG
8801   ACTACCAGAA TGGCTGATAG CCGACACACG AGAAACATAT ATTGAATGTG
8851   CTTTGCGTCT AGCAGAAAAC CATCAAGAAC GCCTTGAACT CCGTCGTTAC
8901   ATCATAGAAA ACAACGGCTT ACAAAAGCTT TTTACAGGCG ACCCTCGTCC
8951   ATTGGGCAAA ATACTGCTTA AGAAAACAAA TGAATGGAAG CGGAAGCACT
9001   TGAGTAAAAA ATAACGGTTT TTTAAAGTAA AAGTGCGGTT AATTTTCAAA
```

FIG.6L.

```
9051  GCGTTTTAAA AACCTCTCAA AAATCAACCG CACTTTTATC TTTATAACGC
9101  TCCCGCGCGC TGACAGTTTA TCTCTTTCTT AAAATACCCA TAAAATTGTG
9151  GCAATAGTTG GGTAATCAAA TTCAATTGTT GATACGGCAA ACTAAAGACG
9201  GCGCGTTCTT CGGCAGTCAT C
```

FIG. 7A.

```
  1 CGCCACTTCA ATTTTGGATT GTTGAAATTC AACTAACCAA AAAGTGCGGT
 51 TAAAATCTGT GGAGAAAATA GGTTGTAGTG AAGAACGAGG TAATTGTTCA
101 AAAGGATAAA GCTCTCTTAA TTGGGCATTG GTTGGCGTTT CTTTTTCGGT
151 TAATAGTAAA TTATATTCTG GACGACTATG CAATCCACCA ACAACTTTAC
201 CGTTGGTTTT AAGCGTTAAT GTAAGTTCTT GCTCTTCTTG GCGAATACGT
251 AATCCCATTT TTTGTTTAGC AAGAAAATGA TCGGGATAAT CATAATAGGT
301 GTTGCCCAAA AATAAATTTT GATGTTCTAA AATCATAAAT TTTGCAAGAT
351 ATTGTGGCAA TTCAATACCT ATTTGTGGCG AAATCGCCAA TTTTAATTCA
401 ATTTCTTGTA GCATAATATT TCCCACTCAA ATCAACTGGT TAAATATACA
451 AGATAATAAA AATAAATCAA GATTTTTGTG ATGACAAACA ACAATTACAA
501 CACCTTTTTT GCAGTCTATA TGCAAATATT TTAAAAAAAT AGTATAAATC
551 CGCCATATAA AATGGTATAA TCTTTCATCT TTCATCTTTC ATCTTTCATC
601 TTTCATCTTT CATCTTTCAT CTTTCATCTT TCATCTTTCA TCTTTCATCT
651 TTCATCTTTC ATCTTTCATC TTTCATCTTT CACATGAAAT GATGAACCGA
701 GGGAAGGGAG GGAGGGGCAA GAATGAAGAG GGAGCTGAAC GAACGCAAAT
751 GATAAAGTAA TTTAATTGTT CAACTAACCT TAGGAGAAAA TATGAACAAG
```

FIG.7B.

```
 801  ATATATCGTC TCAAATTCAG CAAACGCCTG AATGCTTTGG TTGCTGTGTC
 851  TGAATTGGCA CGGGGTTGTG ACCATTCCAC AGAAAAAGGC AGCGAAAAAC
 901  CTGCTCGCAT GAAAGTGCGT CACTTAGCGT TAAAGCCACT TTCCGCTATG
 951  TTACTATCTT TAGGTGTAAC ATCTATTCCA CAATCTGTTT TAGCAAGCGG
1001  CAATTTAACA TCGACCAAAA TGAAATGGTG CAGTTTTTAC AAGAAAACAA
1051  GTAATAAAAC CATTATCCGC AACAGTGTTG ACGCTATCAT TAATTGGAAA
1101  CAATTTAACA TCGACCAAAA TGAAATGGTG CAGTTTTTAC AAGAAAACAA
1151  CAACTCCGCC GTATTCAACC GTGTTACATC TAACCAAATC TCCCAATTAA
1201  AAGGGATTTT AGATTCTAAC GGACAAGTCT TTTTAATCAA CCCAAATGGT
1251  ATCACAATAG GTAAAGACGC AATTATTAAC ACTAATGGCT TTACGGCTTC
1301  TACGCTAGAC ATTTCTAACG AAAACATCAA GGCGCGTAAT TTCACCTTCG
1351  AGCAAACCAA AGATAAAGCG CTCGCTGAAA TTGTGAATCA CGGTTTAATT
1401  ACTGTCGGTA AAGACGGCAG TGTAAATCTT ATTGGTGGCA AAGTGAAAAA
1451  CGAGGGTGTG ATTAGCGTAA ATGGTGGCAG CATTTCTTTA CTCGCAGGGC
1501  AAAAAATCAC CATCAGCGAT ATAATAAACC CAACCATTAC TTACAGCATT
1551  GCCGCGCCTG AAAATGAAGC GGTCAATCTG GGCGATATTT TTGCCAAAGG
```

FIG.7C.

```
1601  CGGTAACATT AATGTCCGTG CTGCCACTAT TCGAAACCAA GGTAAACTTT
1651  CTGCTGATTC TGTAAGCAAA GATAAAAGCG GCAATATTGT TCTTTCCGCC
1701  AAAGAGGGTG AAGCGGAAAT TGGCGGTGTA ATTTCCGCTC AAAATCAGCA
1751  AGCTAAAGGC GGCAAGCTGA TGATTACAGG CGATAAAGTC ACATTAAAAA
1801  CAGGTGCAGT TATCGACCTT TCAGGTAAAG AAGGGGGAGA AACTTACCTT
1851  GGCGGTGACG AGCGCGGCGA AGGTAAAAAC GGCATTCAAT TAGCAAAGAA
1901  AACCTCTTTA GAAAAAGGCT CAACCATCAA TGTATCAGGC AAAGAAAAAG
1951  GCGGACGCGC TATTGTGTGG GGCGATATTG CGTTAATTGA CGGCAATATT
2001  AACGCTCAAG GTAGTGGTGA TATCGCTAAA ACCGGTGGTT TTGTGGAGAC
2051  ATCGGGGCAT TATTTATCCA TTGACAGCAA TGCAATTGTT AAAACAAAAG
2101  AGTGGTTGCT AGACCCTGAT GATGTAACAA TTGAAGCCGA AGACCCCCTT
2151  CGCAATAATA CCGGTATAAA TGATGAATTC CCAACAGGCA CCGGTGAAGC
2201  AAGCGACCCT AAAAAAAATA GCGAACTCAA AACAACGCTA ACCAATACAA
2251  CTATTTCAAA TTATCTGAAA AACGCCTGGA CAATGAATAT AACGGCATCA
2301  AGAAAACTTA CCGTTAATAG CTCAATCAAC ATCGGAAGCA ACTCCCACTT
2351  AATTCTCCAT AGTAAAGGTC AGCGTGGCGG AGGCGTTCAG ATTGATGGAG
2401  ATATTACTTC TAAAGGCGGA AATTTAACCA TTTATTCTGG CGGATGGGTT
```

FIG. 7D.

```
2451  GATGTTCATA AAAATATTAC GCTTGATCAG GGTTTTTTAA ATATTACCGC
2501  CGCTTCCGTA GCTTTTGAAG GTGGAAATAA CAAAGCACGC GACGCGGCAA
2551  ATGCTAAAAT TGTCGCCCAG GGCACTGTAA CCATTACAGG AGAGGGAAAA
2601  GATTTCAGGG CTAACAACGT ATCTTTAAAC GGAACGGGTA AAGGTCTGAA
2651  TATCATTTCA TCAGTGAATA ATTTAACCCA CAATCTTAGT GGCACAATTA
2701  ACATATCTGG GAATATAACA ATTAACCAAA CTACGAGAAA GAACACCTCG
2751  TATTGGCAAA CCAGCCATGA TTCGCACTGG AACGTCAGTG CTCTTAATCT
2801  AGAGACAGGC GCAAATTTTA CCTTTATTAA ATACATTTCA AGCAATAGCA
2851  AAGGCTTAAC AACACAGTAT AGAAGCTCTG CAGGGGTGAA TTTTAACGGC
2901  GTAAATGGCA ACATGTCATT CAATCTCAAA GAAGGAGCGA AAGTTAATTT
2951  CAAATTAAAA CCAAACGAGA ACATGAACAC AAGCAAACCT TTACCAATTC
3001  GGTTTTTAGC CAATATCACA GCCACTGGTG GGGGCTCTGT TTTTTTTGAT
3051  ATATATGCCA ACCATTCTGG CAGAGGGGCT GAGTTAAAAA TGAGTGAAAT
3101  TAATATCTCT AACGGCGCTA ATTTTACCTT AAATTCCCAT GTTCGCGGCG
3151  ATGACGCTTT TAAAATCAAC AAAGACTTAA CCATAAATGC AACCAATTCA
3201  AATTTCAGCC TCAGACAGAC GAAAGATGAT TTTTATGACG GGTACGCACG
```

FIG.7E.

```
3251  CAATGCCATC AATTCAACCT ACAACATATC CATTCTGGGC GGTAATGTCA
3301  CCCTTGGTGG ACAAAACTCA AGCAGCAGCA TTACGGGGAA TATTACTATC
3351  GAGAAAGCAG CAAATGTTAC GCTAGAAGCC AATAACGCCC CTAATCAGCA
3401  AAACATAAGG GATAGAGTTA TAAAACTTGG CAGCTTGCTC GTTAATGGGA
3451  GTTTAAGTTT AACTGGCGAA AATGCAGATA TTAAAGGCAA TCTCACTATT
3501  TCAGAAAGCG CCACTTTTAA AGGAAAGACT AGAGATACCC TAAATATCAC
3551  CGGCAATTTT ACCAATAATG GCACTGCCGA AATTAATATA ACACAAGGAG
3601  TGGTAAAACT TGGCAATGTT ACCAATGATG GTGATTTAAA CATTACCACT
3651  CACGCTAAAC GCAACCAAAG AAGCATCATC GGCGGAGATA TAATCAACAA
3701  AAAAGGAAGC TTAAATATTA CAGACAGTAA TAATGATGCT GAAATCCAAA
3751  TTGGCGGCAA TATCTCGCAA AAAGAAGGCA ACCTCACGAT TTCTTCCGAT
3801  AAAATTAATA TCACCAAACA GATAACAATC AAAAAGGGTA TTGATGGAGA
3851  GGACTCTAGT TCAGATGCGA CAAGTAATGC CAACCTAACT ATTAAAACCA
3901  AAGAATTGAA ATTGACAGAA GACCTAAGTA TTTCAGGTTT CAATAAAGCA
3951  GAGATTACAG CCAAAGATGG TAGAGATTTA ACTATTGGCA ACAGTAATGA
4001  CGGTAACAGC GGTGCCGAAG CCAAAACAGT AACTTTTAAC AATGTTAAAG
```

FIG. 7F.

```
4051  ATTCAAAAAT CTCTGCTGAC GGTCACAATG TGACACTAAA TAGCAAAGTG
4101  AAAACATCTA GCAGCAATGG CGGACGTGAA AGCAATAGCG ACAACGATAC
4151  CGGCTTAACT ATTACTGCAA AAAATGTAGA AGTAAACAAA GATATTACTT
4201  CTCTCAAAAC AGTAAATATC ACCGCGTCGG AAAAGGTTAC CACCACAGCA
4251  GGCTCGACCA TTAACGCAAC AAATGGCAAA GCAAGTATTA CAACCAAAAC
4301  AGGTGATATC AGCGGTACGA TTTCCGGTAA CACGGTAAGT GTTAGCGCGA
4351  CTGGTGATTT AACCACTAAA TCCGGCTCAA AAATTGAAGC GAAATCGGGT
4401  GAGGCTAATG TAACAAGTGC AACAGGTACA ATTGGCGGTA CAATTTCCGG
4451  TAATACGGTA AATGTTACGG CAAACGCTGG CGATTTAACA GTTGGGAATG
4501  GCGCAGAAAT TAATGCGACA GAAGGAGCTG CAACCTTAAC CGCAACAGGG
4551  AATACCTTGA CTACTGAAGC CGGTTCTAGC ATCACTTCAA CTAAGGGTCA
4601  GGTAGACCTC TTGGCTCAGA ATGGTAGCAT CGCAGGAAGC ATTAATGCTG
4651  CTAATGTGAC ATTAAATACT ACAGGCACCT TAACCACCGT GGCAGGCTCG
4701  GATATTAAAG CAACCAGCGG CACCTTGGTT ATTAACGCAA AAGATGCTAA
4751  GCTAAATGGT GATGCATCAG GTGATAGTAC AGAAGTGAAT GCAGTCAACG
4801  ACTGGGGATT TGGTAGTGTG ACTGCGGCAA CCTCAAGCAG TGTGAATATC
4851  ACTGGGGATT TAAACACAGT AAATGGGTTA AATATCATTT CGAAAGATGG
```

FIG. 7G.

```
4901  TAGAAACACT GTGCGCTTAA GAGGCAAGGA AATTGAGGTG AAATATATCC
4951  AGCCAGGTGT AGCAAGTGTA GAAGAAGTAA TTGAAGCGAA ACGCGTCCTT
5001  GAAAAAGTAA AAGATTTATC TGATGAAGAA AGAGAAACAT TAGCTAAACT
5051  TGGTGTAAGT GCTGTACGTT TTGTTGAGCC AAATAATACA ATTACAGTCA
5101  ATACACAAAA TGAATTTACA ACCAGACCGT CAAGTCAAGT GATAATTTCT
5151  GAAGGTAAGG CGTGTTTCTC AAGTGGTAAT GGCGCACGAG TATGTACCAA
5201  TGTTGCTGAC GATGGACAGC CGTAGTCAGT AATTGACAAG GTAGATTTCA
5251  TCCTGCAATG AAGTCATTTT ATTTTCGTAT TATTTACTGT GTGGGTTAAA
5301  GTTCAGTACG GGCTTTACCC ATCTTGTAAA AAATTACGGA GAATACAATA
5351  AAGTATTTTT AACAGGTTAT TATTATGAAA AATATAAAAA GCAGATTAAA
5401  ACTCAGTGCA ATATCAGTAT TGCTTGGCCT GGCTTCTTCA TCATTGTATG
5451  CAGAAGAAGC GTTTTTAGTA AAAGGCTTTC AGTTATCTGG TGCACTTGAA
5501  ACTTTAAGTG AAGACGCCCA ACTGTCTGTA GCAAAATCTT TATCTAAATA
5551  CCAAGGCTCG CAAACTTTAA CAAACCTAAA AACAGCACAG CTTGAATTAC
5601  AGGCTGTGCT AGATAAGATT GAGCCAAATA AATTTGATGT GATATTGCCG
5651  CAACAAACCA TTACGGATGG CAATATCATG TTTGAGCTAG TCTCGAAATC
```

FIG.7H.

```
5701  AGCCGCAGAA AGCCAAGTTT TTTATAAGGC GAGCCAGGGT TATAGTGAAG
5751  AAAATATCGC TCGTAGCCTG CCATCTTTGA AACAAGGAAA AGTGTATGAA
5801  GATGGTCGTC AGTGGTTCGA TTTGCGTGAA TTTAATATGG CAAAAGAAAA
5851  CCCGCTTAAG GTTACCCGTG TACATTACGA ACTAAACCCT AAAAACAAAA
5901  CCTCTAATTT GATAATTGCG GGCTTCTCGC CTTTTGGTAA AACGCGTAGC
5951  TTTATTTCTT ATGATAATTT CGGCGCGAGA GAGTTTAACT ACCAACGTGT
6001  AAGCTTGGGT TTTGTTAATG CCAATTTAAC TGGTCATGAT GATGTGTTAA
6151  TTATACCAGT ATGAGTTATG CTGATTCTAA TGATATCGAC GGCTTACCAA
6201  GTGCGATTAA TCGTAAATTA TCAAAAGGTC AATCTATCTC TGCGAATCTG
6251  AAATGGAGTT ATTATCTCCC AACATTTAAC CTTGGCATGG AAGACCAATT
6301  TAAAATTAAT TTAGGCTACA ACTACCGCCA TATTAATCAA ACCTCCGCGT
6351  TAAATCGCTT GGGTGAAACG AAGAAAAAAT TTGCAGTATC AGGCGTAAGT
6401  GCAGGCATTG ATGGACATAT CCAATTTACC CCTAAAACAA TCTTTAATAT
6451  TGATTTAACT CATCATTATT ACGCGAGTAA ATTACCAGGC TCTTTTGGAA
6501  TGGAGCGCAT TGGCGAAACA TTTAATCGCA GCTATCACAT TAGCACAGCC
6551  AGTTTAGGGT TGAGTCAAGA GTTTGCTCAA GGTTGGCATT TTAGCAGTCA
6601  ATTATCAGGT CAATTTACTC TACAAGATAT TAGCAGTATA GATTTATTCT
```

FIG.7I.

```
6651  CTGTAACAGG TACTTATGGC GTCAGAGGCT TTAAATACGG CGGTGCAAGT
6701  GGTGAGCGCG GTCTTGTATG GCGTAATGAA TTAAGTATGC CAAAATACAC
6751  CCGCTTCCAA ATCAGCCCTT ATGCGTTTTA TGATGCAGGT CAGTTCCGTT
6801  ATAATAGCGA AAATGCTAAA ACTTACGGCG AAGATATGCA CACGGTATCC
6851  TCTGCGGGTT TAGGCATTAA AACCTCTCCT ACACAAAACT TAAGCCTAGA
6901  TGCTTTTGTT GCTCGTCGCT TTGCAAATGC CAATAGTGAC AATTTGAATG
6951  GCAACAAAAA ACGCACAAGC TCACCTACAA CCTTCTGGGG GAGATTAACA
7001  TTCAGTTTCT AACCCTGAAA TTTAATCAAC TGGTAAGCGT TCCGCCTACC
7051  AGTTTATAAC TATATGCTTT ACCCGCCAAT TTACAGTCTA TAGGCAACCC
7101  TGTTTTTACC CTTATATATC AAATAAACAA GCTAAGCTGA GCTAAGCAAA
7151  CCAAGCAAAC TCAAGCAAGC CAAGTAATAC TAAAAAAACA ATTTATATGA
7201  TAAACTAAAG TATACTCCAT GCCATGGCGA TACAAGGGAT TTAATAATAT
7251  GACAAAAGAA AATTTGCAAA ACGCTCCTCA AGATGCGACC GCTTTACTTG
7301  CGGAATTAAG CAACAATCAA ACTCCCCTGC GAATATTTAA ACAACCACGC
7351  AAGCCCAGCC TATTACGCTT GGAACAACAT ATCGCAAAAA AAGATTATGA
7401  GTTTGCTTGT CGTGAATTAA TGGTGATTCT GGAAAAAATG GACGCTAATT
```

FIG.7J.

```
7451  TTGGAGGCGT TCACGATATT GAATTTGACG CACCCGCTCA GCTGGCATAT
7501  CTACCCGAAA AATTACTAAT TTATTTTGCC ACTCGTCTCG CTAATGCAAT
7551  TACAACACTC TTTTCCGACC CCGAATTGGC AATTTCTGAA GAAGGGGCGT
7601  TAAAGATGAT TAGCCTGCAA CGCTGGTTGA CGCTGATTTT TGCCTCTTCC
7651  CCCTACGTTA ACGCAGACCA TATTCTCAAT AAATATAATA TCAACCCAGA
7701  TTCCGAAGGT GGCTTTCATT TAGCAACAGA CAACTCTTCT ATTGCTAAAT
7751  TCTGTATTTT TTACTTACCC GAATCCAATG TCAATATGAG TTTAGATGCG
7801  TTATGGGCAG GGAATCAACA ACTTTGTGCT TCATTGTGTT TTGCGTTGCA
7851  GTCTTCACGT TTTATTGGTA CCGCATCTGC GTTTCATAAA AGAGCGGTGG
7901  TTTTACAGTG GTTTCCTAAA AAACTCGCCG AAATTGCTAA TTTAGATGAA
7951  TTGCCTGCAA ATATCCTTCA TGATGTATAT ATGCACTGCA GTTATGATTT
8001  AGCAAAAAAC AAGCACGATG TTAAGCGTCC ATTAAACGAA CTTGTCCGCA
8051  AGCATATCCT CACGCAAGGA TGGCAAGACC GCTACCTTTA CACCTTAGGT
8101  AAAAAGGACG GCAAACCTGT GATGATGGTA CTGCTTGAAC ATTTTAATTC
8151  GGGACATTCG ATTTATCGTA CACATTCAAC TTCAATGATT GCTGCTCGAG
8201  AAAAATTCTA TTTAGTCGGC TTAGGCCATG AGGGCGTTGA TAAAATAGGT
```

FIG.7K.

```
8251  CGAGAAGTGT TTGACGAGTT CTTTGAAATC AGTAGCAATA ATATAATGGA
8301  GAGACTGTTT TTTATCCGTA AACAGTGCGA AACTTTCCAA CCCGCAGTGT
8351  TCTATATGCC AAGCATTGGC ATGGATATTA CCACGATTTT TGTGAGCAAC
8401  ACTCGGCTTG CCCCTATTCA AGCTGTAGCC CTGGGTCATC CTGCCACTAC
8451  GCATTCTGAA TTTATTGATT ATGTCATCGT AGAAGATGAT TATGTGGGCA
8501  GTGAAGATTG TTTCAGCGAA ACCCTTTTAC GCTTACCCAA AGATGCCCTA
8551  CCTTATGTAC CTTCTGCACT CGCCCCACAA AAAGTGGATT ATGTACTCAG
8601  GGAAAACCCT GAAGTAGTCA ATATCGGTAT TGCCGCTACC ACAATGAAAT
8651  TAAACCCTGA ATTTTTGCTA ACATTGCAAG AAATCAGAGA TAAAGCTAAA
8701  GTCAAAATAC ATTTTCATTT CGCACTTGGA CAATCAACAG GCTTGACACA
8751  CCCTTATGTC AAATGGTTTA TCGAAAGCTA TTTAGGTGAC GATGCCACTG
8801  CACATCCCCA CGCACCTTAT CACGATTATC TGGCAATATT GCGTGATTGC
8851  GATATGCTAC TAAATCCGTT TCCTTTCGGT AATACTAACG GCATAATTGA
8901  TATGGTTACA TTAGGTTTAG TTGGTGTATG CAAAACGGGG GATGAAGTAC
8951  ATGAACATAT TGATGAAGGT CTGTTTAAAC GCTTAGGACT ACCAGAATGG
9001  CTGATAGCCG ACACACGAGA AACATATATT GAATGTGCTT TGCGTCTAGC
9051  AGAAAACCAT CAAGAACGCC TTGAACTCCG TCGTTACATC ATAGAAAACA
```

FIG. 7L.

```
9101  ACGGCTTACA AAAGCTTTTT ACAGGCGACC CTCGTCCATT GGGCAAAATA
9151  CTGCTTAAGA AAACAAATGA ATGGAAGCGG AAGCACTTGA GTAAAAAATA
9201  ACGGTTTTTT AAAGTAAAAG TGCGGTTAAT TTTCAAAGCG TTTTAAAAAC
9251  CTCTCAAAAA TCAACCGCAC TTTTATCTTT ATAACGATCC CGCACGCTGA
9301  CAGTTTATCA GCCTCCCGCC ATAAAACTCC GCCTTTCATG GCGGAGATTT
9351  TAGCCAAAAC TGGCAGAAAT TAAAGGCTAA AATCACCAAA TTGCACCACA
9401  AAATCACCAA TACCCACAAA AAA
```

FIG. 8A.

```
  1 GATCAATCTG GGCGATATTT TTGCCAAAGG TGGTAACATT AATGTCCGCG
 51 CTGCCACTAT TCGCAATAAA GGTAAACTTT CTGCCGACTC TGTAAGCAAA
101 GATAAAAGTG GTAACATTGT TCTCTCTGCC AAAGAAGGTG AAGCGGAAAT
151 TGGCGGTGTA ATTTCCGCTC AAAATCAGCA AGCCAAAGGT GGTAAGTTGA
201 TGATTACAGG CGATAAAGTT ACATTGAAAA CGGGTGCAGT TATCGACCTT
251 TCGGGTAAAG AAGGGGGAGA AACTTATCTT GGCGGTGACG AGCGTGGCGA
301 AGGTAAAAAC GGCATTCAAT TAGCAAAGAA AACCACTTTA GAAAAAGGCT
351 CAACAATTAA TGTGTCAGGT AAAGAAAAAG GTGGGCGCGC TATTGTATGG
401 GGCGATATTG CGTTAATTGA CGGCAATATT AATGCCCAAG GTAAAGATAT
451 CGCTAAAACT GGTGGTTTTG TGGAGACGTC GGGGCATTAC TTATCCATTG
501 ATGATAACGC AATTGTTAAA ACAAAAGAAT GGCTACTAGA CCCAGAGAAT
551 GTGACTATTG AAGCTCCTTC CGCTTCTCGC GTCGAGCTGG GTGCCGATAG
601 GAATTCCCAC TCGGCAGAGG TGATAAAAGT GACCCTAAAA AAAAATAACA
651 CCTCCTTGAC AACACTAACC AATACAACCA TTTCAAATCT TCTGAAAAGT
701 GCCCACGTGG TGAACATAAC GGCAAGGAGA AAACTTACCG TTAATAGCTC
751 TATCAGTATA GAAAGAGGCT CCCACTTAAT TCTCCACAGT GAAGGTCAGG
```

FIG.8B.

```
801   GCGGTCAAGG TGTTCAGATT GATAAAGATA TTACTTCTGA AGGCGGAAAT
851   TTAACCATTT ATTCTGGCGG ATGGGTTGAT GTTCATAAAA ATATTACGCT
901   TGGTAGCGGC TTTTTAAACA TCACAACTAA AGAAGGAGAT ATCGCCTTCG
951   AAGACAAGTC TGGACGGAAC AACCTAACCA TTACAGCCCA AGGGACCATC
1001  ACCTCAGGTA ATAGTAACGG CTTTAGATTT AACAACGTCT CTCTAAACAG
1051  CCTTGGCGGA AAGCTGAGCT TTACTGACAG CAGAGAGGAC AGAGGTAGAA
1101  GAACTAAGGG TAATATCTCA AACAAATTTG ACGGAACGTT AAACATTTCC
1151  GGAACTGTAG ATATCTCAAT GAAAGCACCC AAAGTCAGCT GGTTTTACAG
1201  AGACAAAGGA CGCACCTACT GGAACGTAAC CACTTTAAAT GTTACCTCGG
1251  GTAGTAAATT TAACCTCTCC ATTGACAGCA CAGGAAGTGG CTCAACAGGT
1301  CCAAGCATAC GCAATGCAGA ATTAAATGGC ATAACATTTA ATAAAGCCAC
1351  TTTTAATATC GCACAAGGCT CAACAGCTAA CTTTAGCATC AAGGCATCAA
1401  TAATGCCCTT TAAGAGTAAC GCTAACTACG CATTATTTAA TGAAGATATT
1451  TCAGTCTCAG GGGGGGGTAG CGTTAATTTC AAACTTAACG CCTCATCTAG
1501  CAACATACAA ACCCCTGGCG TAATTATAAA ATCTCAAAAC TTTAATGTCT
1551  CAGGAGGGTC AACTTTAAAT CTCAAGGCTG AAGGTTCAAC AGAAACCGCT
1601  TTTTCAATAG AAAATGATTT AAACTTAAAC GCCACCGGTG GCAATATAAC
```

FIG.8C.

```
1651  AATCAGACAA GTCGAGGGTA CCGATTCACG CGTCAACAAA GGTGTCGCAG
1701  CCAAAAAAAA CATAACTTTT AAAGGGGGTA ATATCACCTT CGGCTCTCAA
1751  AAAGCCACAA CAGAAATCAA AGGCAATGTT ACCATCAATA AAAACACTAA
1801  CGCTACTCTT CGTGGTGCGA ATTTTGCCGA AAACAAATCG CCTTTAAATA
1851  TAGCAGGAAA TGTTATTAAT AATGGCAACC TTACCACTGC CGGCTCCATT
1901  ATCAATATAG CCGGAAATCT TACTGTTTCA AAAGGCGCTA ACCTTCAAGC
1951  TATAACAAAT TACACTTTTA ATGTAGCCGG CTCATTTGAC AACAATGGCG
2001  CTTCAAACAT TTCCATTGCC AGAGGAGGGG CTAAATTTAA AGATATCAAT
2051  AACACCAGTA GCTTAAATAT TACCACCAAC TCTGATACCA CTTACCGCAC
2101  CATTATAAAA GGCAATATAT CCAACAAATC AGGTGATTTG AATATTATTG
2151  ATAAAAAAAG CGACGCTGAA ATCCAAATTG GCGGCAATAT CTCACAAAAA
2201  GAAGGCAATC TCACAATTTC TTCTGATAAA GTAAATATTA CCAATCAGAT
2251  AACAATCAAA GCAGGCGTTG AAGGGGGGCG TTCTGATTCA AGTGAGGCAG
2301  AAAATGCTAA CCTAACTATT CAAACCAAAG AGTTAAAATT GGCAGGAGAC
2351  CTAAATATTT CAGGCTTTAA TAAAGCAGAA ATTACAGCTA AAATGGCAG
2401  TGATTTAACT ATTGGCAATG CTAGCGGTGG TAATGCTGAT GCTAAAAAAG
```

FIG.8D.

```
2451  TGACTTTTGA CAAGGTTAAA GATTCAAAAA TCTCGACTGA CGGTCACAAT
2501  GTAACACTAA ATAGCGAAGT GAAAACGTCT AATGGTAGTA GCAATGCTGG
2551  TAATGATAAC AGCACCGGTT TAACCATTTC CGCAAAAGAT GTAACGGTAA
2601  ACAATAACGT TACCTCCCAC AAGACAATAA ATATCTCTGC CGCAGCAGGA
2651  AATGTAACAA CCAAAGAAGG CACAACTATC AATGCAACCA CAGGCAGCGT
2701  GGAAGTAACT GCTCAAAATG GTACAATTAA AGGCAACATT ACCTCGCAAA
2751  ATGTAACAGT GACAGCAACA GAAAATCTTG TTACCACAGA GAATGCTGTC
2801  ATTAATGCAA CCAGCGGCAC AGTAAACATT AGTACAAAAA CAGGGGATAT
2851  TAAAGGTGGA ATTGAATCAA CTTCCGGTAA TGTAAATATT ACAGCGAGCG
2901  GCAATACACT TAAGGTAAGT AATATCACTG GTCAAGATGT AACAGTAACA
2951  GCGGATGCAG GAGCCTTGAC AACTACAGCA GGCTCAACCA TTAGTGCGAC
3001  AACAGGCAAT GCAAATATTA CAACCAAAAC AGGTGATATC AACGGTAAAG
3051  TTGAATCCAG CTCCGGCTCT GTAACACTTG TTGCAACTGG AGCAACTCTT
3101  GCTGTAGGTA ATATTTCAGG TAACACTGTT ACTATTACTG CGGATAGCGG
3151  TAAATTAACC TCCACAGTAG GTTCTACAAT TAATGGGACT AATAGTGTAA
3201  CCACCTCAAG CCAATCAGGC GATATTGAAG GTACAATTTC TGGTAATACA
3251  GTAAATGTTA CAGCAAGCAC TGGTGATTTA ACTATTGGAA ATAGTGCAAA
```

FIG.8E.

```
3301  AGTTGAAGCG AAAAATGGAG CTGCAACCTT AACTGCTGAA TCAGGCAAAT
3351  TAACCACCCA AACAGGCTCT AGCATTACCT CAAGCAATGG TCAGACAACT
3401  CTTACAGCCA AGGATAGCAG TATCGCAGGA AACATTAATG CTGCTAATGT
3451  GACGTTAAAT ACCACAGGCA CTTTAACTAC TACAGGGGAT TCAAAGATTA
3501  ACGCAACCAG TGGTACCTTA ACAATCAATG CAAAAGATGC CAAATTAGAT
3551  GGTGCTGCAT CAGGTGACCG CACAGTAGTA AATGCAACTA ACGCAAGTGG
3601  CTCTGGTAAC GTGACTGCGA AAACCTCAAG CAGCGTGAAT ATCACCGGGG
3651  ATTTAAACAC AATAAATGGG TTAAATATCA TTTCGGAAAA TGGTAGAAAC
3701  ACTGTGCGCT TAAGAGGCAA GGAAATTGAT GTGAAATATA TCCAACCAGG
3751  TGTAGCAAGC GTAGAAGAGG TAATTGAAGC GAAACGCGTC CTTGAGAAGG
3801  TAAAAGATTT ATCTGATGAA GAAAGAGAAA CACTAGCCAA ACTTGGTGTA
3851  AGTGCTGTAC GTTTCGTTGA GCCAAATAAT GCCATTACGG TTAATACACA
3901  AAACGAGTTT ACAACCAAAC CATCAAGTCA AGTGACAATT TCTGAAGGTA
3951  AGGCGTGTTT CTCAAGTGGT AATGGCGCAC GAGTATGTAC CAATGTTGCT
4001  GACGATGGAC AGCAGTAGTC AGTAATTGAC AAGGTAGATT TCATCCTGCA
4051  ATGAAGTCAT TTTATTTTCG TATTATTTAC TGTGTGGGTT AAAGTTCAGT
```

FIG.8F.

```
4101  ACGGGCTTTA CCCACCTTGT AAAAAATTAC GAAAAATACA ATAAAGTATT
4151  TTTAACAGGT TATTATTATG AAAAACATAA AAAGCAGATT AAAACTCAGT
4201  GCAATATCAA TATTGCTTGG CTTGGCTTCT TCATCGACGT ATGCAGAAGA
4251  AGCGTTTTTA GTAAAAGGCT TTCAGTTATC TGGCGCG
```

FIG. 9A.

```
  1 GGGAATGAGC GTCGTACACG GTACAGCAAC CATGCAAGTA GACGGCAATA
 51 AAACCACTAT CCGTAATAGC GTCAATGCTA TCATCAATTG GAAACAATTT
101 AACATTGACC AAAATGAAAT GGAGCAGTTT TTACAAGAAA GCAGCAACTC
151 TGCCGTTTTC AACCGTGTTA CATCTGACCA AATCTCCCAA TTAAAAGGGA
201 TTTTAGATTC TAACGGACAA GTCTTTTTAA TCAACCCAAA TGGTATCACA
251 ATAGGTAAAG ACGCAATTAT TAACACTAAT GGCTTTACTG CTTCTACGCT
301 AGACATTTCT AACGAAAACA TCAAGGCGCG TAATTTCACC CTTGAGCAAA
351 CCAAGGATAA AGCACTCGCT GAAATCGTGA ATCACGGTTT AATTACCGTT
401 GGTAAAGACG GTAGCGTAAA CCTTATTGGT GGCAAAGTGA AAAACGAGGG
451 CGTGATTAGC GTAAATGGCG GTAGTATTTC TTTACTTGCA GGGCAAAAAA
501 TCACCATCAG CGATATAATA AATCCAACCA TCACTTACAG CATTGCTGCA
551 CCTGAAAACG AAGCGATCAA TCTGGGCGAT ATTTTTGCCA AAGGTGGTAA
601 CATTAATGTC CGCGCTGCCA CTATTCGCAA TAAAGGTAAA CTTTCTGCCG
651 ACTCTGTAAG CAAAGATAAA AGTGGTAACA TTGTTCTCTC TGCCAAAGAA
701 GGTGAAGCGG AAATTGGCGG TGTAATTTCC GCTCAAAATC AGCAAGCCAA
751 AGGTGGTAAG TTGATGATTA CAGGTGATAA AGTCACATTA AAAACAGGTG
```

FIG.9B.

```
 801  CAGTTATCGA CCTTTCAGGT AAAGAAGGGG GAGAGACTTA TCTTGGCGGT
 851  GATGAGCGTG GCGAAGGTAA AAATGGTATT CAATTAGCGA AGAAAACCTC
 901  TTTAGAAAAA GGCTCGACAA TTAATGTATC AGGCAAAGAA AAAGGCGGGC
 951  GCGCTATTGT ATGGGGCGAT ATTGCATTAA TTAATGGTAA CATTAATGCT
1001  CAAGGTAGCG ATATTGCTAA AACTGGCGGC TTTGTGGAAA CATCAGGACA
1051  TGACTTATCC ATTGGTGATG ATGTGATTGT TGACGCTAAA GAGTGGTTAT
1101  TAGACCCAGA TGATGTGTCC ATTGAAACTC TTACATCTGG ACGCAATAAT
1151  ACCGGCGAAA ACCAAGGATA TACAACAGGA GATGGGACTA AAGAGTCACC
1201  TAAAGGTAAT AGTATTTCTA AACCTACATT AACAAACTCA ACTCTTGAGC
1251  AAATCCTAAG AAGAGGTTCT TATGTTAATA TCACTGCTAA TAATAGAATT
1301  TATGTTAATA GCTCCATCAA CTTATCTAAT GGCAGTTTAA CACTTCACAC
1351  TAAACGAGAT GGAGTTAAAA TTAACGGTGA TATTACCTCA AACGAAAATG
1401  GTAATTTAAC CATTAAAGCA GGCTCTTGGG TTGATGTTCA TAAAAACATC
1451  ACGCTTGGTA CGGGTTTTTT GAATATTGTC GCTGGGGATT CTGTAGCTTT
1501  TGAGAGAGAG GGCGATAAAG CACGTAACGC AACAGATGCT CAAATTACCG
1551  CACAAGGGAC GATAACCGTC AATAAAGATG ATAAACAATT TAGATTCAAT
1601  AATGTATCTA TTAACGGGAC GGGCAAGGGT TTAAAGTTTA TTGCAAATCA
```

FIG. 9C.

```
1651  AAATAATTTC ACTCATAAAT TTGATGGCGA AATTAACATA TCTGGAATAG
1701  TAACAATTAA CCAAACCACG AAAAAAGATG TTAAATACTG GAATGCATCA
1751  AAAGACTCTT ACTGGAATGT TTCTTCTCTT ACTTTGAATA CGGTGCAAAA
1801  ATTTACCTTT ATAAAATTCG TTGATAGCGG CTCAAATTCC CAAGATTTGA
1851  GGTCATCACG TAGAAGTTTT GCAGGCGTAC ATTTTAACGG CATCGGAGGC
1901  AAAACAAACT TCAACATCGG AGCTAACGCA AAAGCCTTAT TTAAATTAAA
1951  ACCAAACGCC GCTACAGACC CAAAAAAAGA ATTACCTATT ACTTTTAACG
2001  CCAACATTAC AGCTACCGGT AACAGTGATA GCTCTGTGAT GTTTGACATA
2051  CACGCCAATC TTACCTCTAG AGCTGCCGGC ATAAACATGG ATTCAATTAA
2101  CATTACCGGC GGGCTTGACT TTTCCATAAC ATCCCATAAT CGCAATAGTA
2151  ATGCTTTTGA AATCAAAAAA GACTTAACTA TAAATGCAAC TGGCTCGAAT
2201  TTTAGTCTTA AGCAAACGAA AGATTCTTTT TATAATGAAT ACAGCAAACA
2251  CGCCATTAAC TCAAGTCATA ATCTAACCAT TCTTGGCGGC AATGTCACTC
2301  TAGGTGGGGA AAATTCAAGC AGTAGCATTA CGGGCAATAT CAATATCACC
2351  AATAAAGCAA ATGTTACATT ACAAGCTGAC ACCAGCAACA GCAACACAGG
2401  CTTGAAGAAA AGAACTCTAA CTCTTGGCAA TATATCTGTT GAGGGGAATT
```

FIG.9D.

```
2451  TAAGCCTAAC TGGTGCAAAT GCAAACATTG TCGGCAATCT TTCTATTGCA
2501  GAAGATTCCA CATTTAAAGG AGAAGCCAGT GACAACCTAA ACATCACCGG
2551  CACCTTTACC AACAACGGTA CCGCCAACAT TAATATAAAA CAAGGAGTGG
2601  TAAAACTCCA AGGCGATATT ATCAATAAAG GTGGTTTAAA TATCACTACT
2651  AACGCCTCAG GCACTCAAAA AACCATTATT AACGGAAATA TAACTAACGA
2701  AAAAGGCGAC TTAAACATCA AGAATATTAA AGCCGACGCC GAAATCCAAA
2751  TTGGCGGCAA TATCTCACAA AAAGAAGGCA ATCTCACAAT TTCTTCTGAT
2801  AAAGTAAATA TTACCAATCA GATAACAATC AAAGCAGGCG TTGAAGGGGG
2851  GCGTTCTGAT TCAAGTGAGG CAGAAAATGC TAACCTAACT ATTCAAACCA
2901  AAGAGTTAAA ATTGGCAGGA GACCTAAATA TTTCAGGCTT TAATAAAGCA
2951  GAAATTACAG CTAAAAATGG CAGTGATTTA ACTATTGGCA ATGCTAGCGG
3001  TGGTAATGCT GATGCTAAAA AAGTGACTTT TGACAAGGTT AAAGATTCAA
3051  AAATCTCGAC TGACGGTCAC AATGTAACAC TAAATAGCGA AGTGAAAACG
3101  TCTAATGGTA GTAGCAATGC TGGTAATGAT AACAGCACCG GTTTAACCAT
3151  TTCCGCAAAA GATGTAACGG TAAACAATAA CGTTACCTCC CACAAGACAA
3201  TAAATATCTC TGCCGCAGCA GGAAATGTAA CAACCAAAGA AGGCACAACT
3251  ATCAATGCAA CCACAGGCAG CGTGGAAGTA ACTGCTCAAA ATGGTACAAT
```

FIG. 9E.

```
3301 TAAAGGCAAC ATTACCTCGC AAAATGTAAC AGTGACAGCA ACAGAAAATC
3351 TTGTTACCAC AGAGAATGCT GTCATTAATG CAACCAGCGG CACAGTAAAC
3401 ATTAGTACAA AAACAGGGGA TATTAAAGGT GGAATTGAAT CAACTTCCGG
3451 TAATGTAAAT ATTACAGCGA GCGGCAATAC ACTTAAGGTA AGTAATATCA
3501 CTGGTCAAGA TGTAACAGTA ACAGCGGATG CAGGAGCCTT GACAACTACA
3551 GCAGGCTCAA CCATTAGTGC GACAACAGGC AATGCAAATA TTACAACCAA
3601 AACAGGTGAT ATCAACGGTA AAGTTGAATC CAGCTCCGGC TCTGTAACAC
3651 TTGTTGCAAC TGGAGCAACT CTTGCTGTAG GTAATATTTC AGGTAACACT
3701 GTTACTATTA CTGCGGATAG CGGTAAATTA ACCTCCACAG TAGGTTCTAC
3751 AATTAATGGG ACTAATAGTG TAACCACCTC AAGCCAATCA GGCGATATTG
3801 AAGGTACAAT TTCTGGTAAT ACAGTAAATG TTACAGCAAG CACTGGTGAT
3851 TTAACTATTG GAAATAGTGC AAAAGTTGAA GCGAAAAATG GAGCTGCAAC
3901 CTTAACTGCT GAATCAGGCA AATTAACCAC CCAAACAGGC TCTAGCATTA
3951 CCTCAAGCAA TGGTCAGACA ACTCTTACAG CCAAGGATAG CAGTATCGCA
4001 GGAAACATTA ATGCTGCTAA TGTGACGTTA AATACCACAG GCACTTTAAC
4051 TACTACAGGG GATTCAAAGA TTAACGCAAC CAGTGGTACC TTAACAATCA
```

FIG.9F.

```
4101  ATGCAAAAGA TGCCAAATTA GATGGTGCTG CATCAGGTGA CCGCACAGTA
4151  GTAAATGCAA CTAACGCAAG TGGCTCTGGT AACGTGACTG CGAAAACCTC
4201  AAGCAGCGTG AATATCACCG GGGATTTAAA CACAATAAAT GGGTTAAATA
4251  TCATTTCGGA AAATGGTAGA AACACTGTGC GCTTAAGAGG CAAGGAAATT
4301  GATGTGAAAT ATATCCAACC AGGTGTAGCA AGCGTAGAAG AGGTAATTGA
4351  AGCGAAACGC GTCCTTGAGA AGGTAAAAGA TTTATCTGAT GAAGAAAGAG
4401  AAACACTAGC CAAACTTGGT GTAAGTGCTG TACGTTTCGT TGAGCCAAAT
4451  AATGCCATTA CGGTTAATAC ACAAAACGAG TTTACAACCA AACCATCAAG
4501  TCAAGTGACA ATTTCTGAAG GTAAGGCGTG TTTCTCAAGT GGTAATGGCG
4551  CACGAGTATG TACCAATGTT GCTGACGATG GACAGCAGTA GTCAGTAATT
4601  GACAAGGTAG ATTTCATCCT GCAATGAAGT CATTTTATTT TCGTATTATT
4651  TACTGTGTGG GTTAAAGTTC AGTACGGGCT TTACCCACCT TGTAAAAAAT
4701  TA
```

FIG.10A. COMPARISON OF DERIVED AMINO ACID SEQUENCE

```
             1                                                      50
Hmw3com      .......... .......... .......... .......... ..........
Hmw4com      .......... .......... .......... .......... ..........
Hmw1com      MNKIYRLKFS KRLNALVAVS ELARGCDHST EKGSEKPARM KVRHLALKPL
Hmw2com      MNKIYRLKFS KRLNALVAVS ELARGCDHST EKGSEKPARM KVRHLALKPL

             51                                                    100
Hmw3com      .......... .......... .......... .......... ..........
Hmw4com      .......... .......... ..GMSVVHGT ATMQVDGNKT TIRNSVNAII
Hmw1com      SAMLLSLGVT SIPQSVLASG LQGMSVVHGT ATMQVDGNKT TIRNSVNAII
Hmw2com      SAMLLSLGVT SIPQSVLASG LQGMSVVHGT ATMQVDGNKT TIRNSVNAII

             101                                                   150
Hmw3com      .......... .......... .......... .......... ..........
Hmw4com      NWKQFNIDQN EMEQFLQESS NSAVFNRVTS DQISQLKGIL DSNGQVFLIN
```

FIG.10B.

```
Hmw1com   NWKQFNIDQN EMVQFLQENN NSAVFNRVTS NQISQLKGIL DSNGQVFLIN
Hmw2com   NWKQFNIDQN EMVQFLQENN NSAVFNRVTS NQISQLKGIL DSNGQVFLIN

          151                                               200
Hmw3com   .......... .......... .......... .......... ..........
Hmw4com   PNGITIGKDA IINTNGFTAS TLDISNENIK ARNFTLEQTK DKALAEIVNH
Hmw1com   PNGITIGKDA IINTNGFTAS TLDISNENIK ARNFTLEQTK DKALAEIVNH
Hmw2com   PNGITIGKDA IINTNGFTAS TLDISNENIK ARNFTLEQTK DKALAEIVNH

          201                                               250
Hmw3com   .......... .......... .......... .......... ..........
Hmw4com   GLITVGKDGS VNLIGGKVKN EGVISVNGGS ISLLAGQKIT ISDIINPTIT
Hmw1com   GLITVGKDGS VNLIGGKVKN EGVISVNGGS ISLLAGQKIT ISDIINPTIT
Hmw2com   GLITVGKDGS VNLIGGKVKN EGVISVNGGS ISLLAGQKIT ISDIINPTIT

          251                                               300
Hmw3com   .......... INLGDIFAKG GNINVRAATI RNKGKLSADS VSKDKSGNIV
```

FIG. 10C.

```
Hmw4com   YSIAAPENEA INLGDIFAKG GNINVRAATI RNKGKLSADS VSKDKSGNIV
Hmw1com   YSIAAPENEA VNLGDIFAKG GNINVRAATI RNKGKLSADS VSKDKSGNIV
Hmw2com   YSIAAPENEA VNLGDIFAKG GNINVRAATI RNKGKLSADS VSKDKSGNIV

          301                                              350
Hmw3com   LSAKEGEAEI GGVISAQNQQ AKGGKLMITG DKVTLKTGAV IDLSGKEGGE
Hmw4com   LSAKEGEAEI GGVISAQNQQ AKGGKLMITG DKVTLKTGAV IDLSGKEGGE
Hmw1com   LSAKEGEAEI GGVISAQNQQ AKGGKLMITG DKVTLKTGAV IDLSGKEGGE
Hmw2com   LSAKEGEAEI GGVISAQNQQ AKGGKLMITG DKVTLKTGAV IDLSGKEGGE

          351                                              400
Hmw3com   TYLGGDERGE GKNGIQLAKK TTLEKGSTIN VSGKEKGGRA IVWGDIALID
Hmw4com   TYLGGDERGE GKNGIQLAKK TTLEKGSTIN VSGKEKGGRA IVWGDIALID
Hmw1com   TYLGGDERGE GKNGIQLAKK TTLEKGSTIN VSGKEKGGRA IVWGDIALID
Hmw2com   TYLGGDERGE GKNGIQLAKK TTLEKGSTIN VSGKEKGGRA IVWGDIALID
```

FIG.10D.

```
             401                                                  450
Hmw3com   GNINAQGK.D IAKTGGFVET SGHYLSIDDN AIVKTKEWLL DPENVTIEAP
Hmw4com   GNINAQGS.D IAKTGGFVET SGHDLSIGDD VIVDAKEWLL DPDDVSIETL
Hmw1com   GNINAQGSGD IAKTGGFVET SGHDLFIKDN AIVDAKEWLL DPDNVTINAE
Hmw2com   GNINAQGSGD IAKTGGFVET SGHYLSIESN AIVKTKEWLL DPDDVTIEAE

             451                                                  500
Hmw3com   SASRVELGAD RNSHSAEVIK VTLKKNNTSL TTLTNTTISN LLKSAHVVNI
Hmw4com   TSGRNNTGEN QGYTTGDGTK ESPKGNSISK PTLTNSTLEQ ILRRGSYVNI
Hmw1com   TAGRSNTSED DEYTGSGNSA STPKRNKE.K TTLTNTTLES ILKKGTFVNI
Hmw2com   DPLRNNTGIN DEFPTGTGEA SDPKKNSELK TTLTNTTISN YLKNAWTMNI

             501                                                  550
Hmw3com   TARRKLTVNS SISIERGSHL ILHSEGQGGQ GVQIDKDITS .E...GGNLT
Hmw4com   TANNRIYVNS SINLSNGS.L TLHTK...RD GVKINGDITS NE...NGNLT
Hmw1com   TANQRIYVNS SINL.SNGSL TLWSEGRSGG GVEINNDITT GDDTRGANLT
Hmw2com   TASRKLTVNS SINGSNGSHL ILHSKGQRGG GVQIDGDIT. ...SKGGNLT
```

FIG. 10E.

```
            551                                                    600
Hmw3com     IYSGGWVDVH KNITLGS.GF LNITTKEGDI AFEDKSGR.. ..NNLTITAQ
Hmw4com     IKAGSWVDVH KNITLGT.GF LNIVAGDS.V AFEREGDKAR NATDAQITAQ
Hmw1com     IYSGGWVDVH KNISLGAQGN INITAKQD.I AFEKGSNQV. ......ITGQ
Hmw2com     IYSGGWVDVH KNITLD.QGF LNITA.AS.V AFEGGNNKAR DANNLTITAQ

            601                                                    650
Hmw3com     GTITSG.NSN GFRFNNVSLN SLGGKLSFTD SREDRGRRTK GNISNKFDGT
Hmw4com     GTITVNKDDK QFRFNNVSIN GTGKGLKFIA NQN....... .NFTHKFDGE
Hmw1com     GTIT.SGNQK GFRFNNVSLN GTGSGLQFTT KRTN.....K YAITNKFEGT
Hmw2com     GTVTITGEGK DFRANNVSLN GTGKGLNIIS SVNN...... ..LTHNLSGT

            651                                                    700
Hmw3com     LNISGTVDIS MKAPKVSWFY RD.KGRTYWN VTTLNVTSGS KFNLSIDSTG
Hmw4com     INISGIVTIN QTTKKDVKYW NA.SKDSYWN VSSLTLNTVQ KFTF.IKFVD
Hmw1com     LNISGKVNIS MVLPKNESGY DKFKGRTYWN LTSLNVSESG EFNLTIDSRG
```

FIG.10F.

```
Hmw2com  INISGNITIN QTTRKNTSYW QTSHD.SHWN VSALNLETGA NFTF.IKYIS

         701                                              750
Hmw3com  SGSTG...PS IRNA..ELNG ITFN....KA TFNIAQGSTA NFSIKASIMP
Hmw4com  SGSNS...QD LRSSRRSFAG VHFNGIGGKT NFNIGANAKA LFKLKPNAAT
Hmw1com  SDSAGTLTQ. ....PYNLNG ISFN...KDT TFNVERNARV NFDIKAPIGI
Hmw2com  SNSKGLTTQY RSSAGVNFNG V..N...GNM SFNLKEGAKV NFKLKPNENM

         751                                              800
Hmw3com  FKSNANYAL. FNEDISVSG. .GGSVNFKLN ASSSNIQTPG VIIKSQNFNV
Hmw4com  DPKKELPIT. FNANITATGN SDSSVMFDIH A...NLTSRA AGINMDSINI
Hmw1com  NKYSSLNYAS FNGNISVSG. .GGSVDFTLL ASSSNVQTPG VVINSKYFNV
Hmw2com  NTSKPLPI.R FLANITATG. .GGSVFFDIY ANHS...GRG AELKMSEINI

         801                                              850
Hmw3com  SGGSTLNLKA EGSTETAFSI ENDLNLNATG GNITIRQVEG T..DSRVNKG
Hmw4com  TGGLDFSITS HNRNSNAFEI KKDLTINATG SNFSLKQTKD SFYNEYSKHA
```

FIG. 10G.

```
Hmw1com   STGSSLRFKT SGSTKTGFSI EKDLTLNATG GNITLLQVEG T..DGMIGKG
Hmw2com   SNGANFTLNS HVRGDDAFKI NKDLTINATN SNFSLRQTKD DFYDGYARNA

           851                                            900
Hmw3com   VAAKKNITFK GGNITFGSQK ATTEIKGNVT INKNTNATLR GANFAEN...
Hmw4com   INSSHNLTIL GGNVTLGGEN SSSSITGNIN ITNKANVTLQ ADTSNSNTGL
Hmw1com   IVAKKNITFE GGNITFGSRK AVTEIEGNVT INNNANVTLI GSDFDNHQ..
Hmw2com   INSTYNISIL GGNVTLGGQN SSSSITGNIT IEKAANVTLE ANNAPNQQNI

           901                                            950
Hmw3com   KSPLNIAGNV INNGNLTTAG SIINIAGNLT VSKGANLQAI TNYTFNVAGS
Hmw4com   KKRTLTLGNI SVEGNLSLTG ANANIVGNLS IAEDSTFKGE ASDNLNITGT
Hmw1com   KPLTIKKDVI INSGNLTAGG NIVNIAGNLT VESNANFKAI TNFTFNVGGL
Hmw2com   RDRVIKLGSL LVNGSLSLTG ENADIKGNLT ISESATFKGK TRDTLNITGN

           951                                           1000
```

FIG. 10H.

```
Hmw3com   FDNNGASNIS IARGGAKFK. DINNTSSLNI TTNSDTTYRT IIKGNISNKS
Hmw4com   FTNNGTANIN IKQGVVKLQG DINNKGGLNI TTNASGTQKT IINGNITNEK
Hmw1com   FDNKGNSNIS IAKGGARFK. DIDNSKNLSI TTNSSSTYRT IISGNITNKN
Hmw2com   FTNNGTAEIN ITQGVVKLG. NVTNDGDLNI TTHAKRNQRS IIGGDIINNK

          1001                                             1050
Hmw3com   GDLNIIDKKS DAEIQIGGNI SQKEGNLTIS SDKVNITNQI TIKAGVEGGR
Hmw4com   GDLNIKNIKA DAEIQIGGNI SQKEGNLTIS SDKVNITNQI TIKAGVEGGR
Hmw1com   GDLNITNEGS DTEMQIGGDI SQKEGNLTIS SDKINITKQI TIKAGVDGEN
Hmw2com   GSLNITDSNN DAEIQIGGNI SQKEGNLTIS SDKINITKQI TIKKGIDGED

          1051                                             1100
Hmw3com   SDSSEAENAN LTIQTKELKL AGDLNISGFN KAEITAKNGS DLTIGNASGG
Hmw4com   SDSSEAENAN LTIQTKELKL AGDLNISGFN KAEITAKNGS DLTIGNASGG
Hmw1com   SDSDATNNAN LTIKTKELKL TQDLNISGFN KAEITAKDGS DLTIGNTNSA
Hmw2com   SSSDATSNAN LTIKTKELKL TEDLSISGFN KAEITAKDGR DLTIGNSNDG
```

FIG.10I.

```
           1101                                                     1150
Hmw3com    N..ADAKKVT FDKVKDSKIS TDGHNVTLNS EVKT..SNGS SNAGDNSTG
Hmw4com    N..ADAKKVT FDKVKDSKIS TDGHNVTLNS EVKT..SNGS SNAGDNSTG
Hmw1com    D.GTNAKKVT FNQVKDSKIS ADGHKVTLHS KVETSGSNNN TEDSSDNNAG
Hmw2com    NSGAEAKKVT FNNVKDSKIS ADGHNVTLNS KVKTSSSNGG RESNSDNDTG

           1151                                                     1200
Hmw3com    LTISAKDVTV NNNVTSHKTI NISAAAGNVT TKEGTTINAT TGSVEVTAQN
Hmw4com    LTISAKDVTV NNNVTSHKTI NISAAAGNVT TKEGTTINAT TGSVEVTAQN
Hmw1com    LTIDAKNVTV NNNITSHKAV SISATSGEIT TKTGTTINAT TGNVEIT...
Hmw2com    LTITAKNVEV NKDVTSLKTV NITA.SEKVT TTAGSTINAT NGKASIT...

           1201                                                     1250
Hmw3com    GTIKGNITSQ NVTVTATENL VTTENAVINA TSGTVNISTK TGDIKGGIES
Hmw4com    GTIKGNITSQ NVTVTATENL VTTENAVINA TSGTVNISTK TGDIKGGIES
Hmw1com    .......... .......... .......... ........AQ TGDIKGGIES
```

FIG. 10J.

```
Hmw2com   .......... .......... .......... ........TK T.........

          1251                                               1300
Hmw3com   TSGNVNITAS GNTLKVSNIT GQDVTVTADA GALTTTAGST ISATTGNANI
Hmw4com   TSGNVNITAS GNTLKVSNIT GQDVTVTADA GALTTTAGST ISATTGNANI
Hmw1com   SSGSVTLTAT EGALAVSNIS GNTVTVTANS GALTTLAGST IKG.TESVTT
Hmw2com   .......... .......... .......... .......... ..........

          1301                                               1350
Hmw3com   TTKTGDINGK VESSSGSVTL VATGATLAVG NISGNTVTIT ADSGKLTSTV
Hmw4com   TTKTGDINGK VESSSGSVTL VATGATLAVG NISGNTVTIT ADSGKLTSTV
Hmw1com   SSQSGDIG.. .......... .........G TISGGTVEVK ATESLTTQSN
Hmw2com   ....GDIS.. .......... .........G TISGNTVSVS ATVDLTTKSG

          1351                                               1400
Hmw3com   GSTINGTNSV TTSSQSGDIE GTISGNTVNV TASTGDLTIG NSAKVEAKNG
Hmw4com   GSTINGTNSV TTSSQSGDIE GTISGNTVNV TASTGDLTIG NSAKVEAKNG
```

FIG.10K.

```
Hmw1com   SKIKATTGEA NVTSATGTIG GTISGNTVNV TANAGDLTVG NGAEINATEG
Hmw2com   SKIEAKSGEA NVTSATGTIG GTISGNTVNV TANAGDLTVG NGAEINATEG

          1401                                             1450
Hmw3com   AATLTAESGK LTTQTGSSIT SSNGQTTLTA KDSSIAGNIN AANVTLNTTG
Hmw4com   AATLTAESGK LTTQTGSSIT SSNGQTTLTA KDSSIAGNIN AANVTLNTTG
Hmw1com   AATLTTSSGK LTTEASSHIT SAKGQVNLSA QDSSVAGSIN AANVTLNTTG
Hmw2com   AATLTATGNT LTTEAGSSIT STKGQVDLLA QNSSIAGNIN AANVTLNTTG

          1451                                             1500
Hmw3com   TLTTTGDSKI NATSGTLTIN AKDAKLDGAA SGDRTVVNAT NASGSGNVTA
Hmw4com   TLTTTGDSKI NATSGTLTIN AKDAKLDGAA SGDRTVVNAT NASGSGNVTA
Hmw1com   TLTTVKGSNI NATSGTLTIN AKDAELNGAA LGNHTVVNAT NANGSGSVIA
Hmw2com   TLTTVAGSDI KATSGTLTIN AKDAKLNGDA SGDSTEVNAV NASGSGSVTA

          1501                                             1550
```

FIG. 10L.

```
Hmw3com   KTSSSVNITG DLNTINGLNI ISENGRNTVR LRGKEIDVKY IQPGVASVEE
Hmw4com   KTSSSVNITG DLNTINGLNI ISENGRNTVR LRGKEIDVKY IQPGVASVEE
Hmw1com   TTSSRVNITG DLITINGLNI ISKNGINTVL LKGVKIDVKY IQPGIASVDE
Hmw2com   ATSSSVNITG DLNTVNGLNI ISKDGRNTVR LRGKEIEVKY IQPGVASVEE

          1551                                              1600
Hmw3com   VIEAKRVLEK VKDLSDEERE TLAKLGVSAV RFVEPNNAIT VNTQNEFTTK
Hmw4com   VIEAKRVLEK VKDLSDEERE TLAKLGVSAV RFVEPNNAIT VNTQNEFTTK
Hmw1com   VIEAKRILEK VKDLSDEERE ALAKLGVSAV RFIEPNNTIT VDTQNEFATR
Hmw2com   VIEAKRVLEK VKDLSDEERE TLAKLGVSAV RFVEPNNTIT VNTQNEFTTR

          1601                          1632
Hmw3com   PSSQVTISEG KACFSSGNGA RVCTNVADDG QQ
Hmw4com   PSSQVTISEG KACFSSGNGA RVCTNVADDG QQ
Hmw1com   PLSRIVISEG RACFSNSDGA TVCVNIADNG R.
Hmw2com   PSSQVIISEG KACFSSGNGA RVCTNVADDG QP
```

HIGH MOLECULAR WEIGHT SURFACE PROTEINS OF NON-TYPEABLE HAEMOPHILUS

This is a division of application Ser. No. 08/302,832 filed Oct. 5, 1994, now U.S. Pat. No. 5,603,938 the national phase of International Application No. PCT/US93/02166, filed Mar. 16, 1993 which claims priority to GB 9205704.1 filed Mar. 16, 1992.

SUMMARY OF INVENTION

The inventors, in an effort to further characterize the high molecular weight (HMW) Haemophilus proteins, have cloned, expressed and sequenced the genes coding for two immunodominant HMW proteins (designated HMW1 and HMW2) from a prototype non-typeable Haemophilus strain and have cloned, expressed and almost completely sequenced the genes coding for two additional immunodominant HMW proteins (designated HMW3 and HMW4) from another non-typeable Haemophilus strain.

In accordance with one aspect of the present invention, therefore, there is provided an isolated and purified gene coding for a high molecular weight protein of a non-typeable Haemophilus strain, particularly a gene coding for protein HMW1, HMW2, HMW3 or HMW4, as well as any variant or fragment of such protein which retains the immunological ability to protect against disease caused by a non-typeable Haemophilus strain. In another aspect, the invention provides a high molecular weight protein of non-typeable *Haemophilus influenzae* which is encoded by these genes.

BRIEF DESCRIPTION OF DRAWINGS

FIGS. 1A to 1G show a DNA sequence of a gene coding for protein HMW1 (SEQ ID NO: 1);

FIGS. 2A and 2B show a derived amino acid sequence of protein HMW1 (SEQ ID NO: 2);

FIGS. 3A to 3G show a DNA sequence of a gene coding for protein HMW2 (SEQ ID NO: 3);

FIGS. 4A and 4B show a derived amino acid sequence of HMW2 (SEQ ID NO: 4);

FIG. 5B shows the restriction map of the T7 expression vector pT7-7, which contains the T7 RNA polymerase promoxer 10, a ribosome binding site (rbs) and the transriptional start site for the T7 gene 10 protein upstream from a multiple cloning site;

FIGS. 6A to 6C contain the DNA sequence of a gene cluster for the hmw1 gene (SEQ ID NO: 5), comprising nucleotides 351 to 4958 (ORF a) (as in FIG. 1), as well as two additional downstream genes in the 3' flanking region, comprising ORFs b, nucleotides 5114–6748 and c nucleotides 7062–9011;

FIGS. 7A to 7C contain the DNA sequence of a gene cluster for the hmw2 gene (SEQ ID NO: 6), comprising nucleotides 792 to 5222 (ORF a) (as in FIG. 3), as well as two additional downstream genes in the 3' flanking region, comprising ORFs b, nucleotides 5375–7009, and c, nucleotides 7249–9196;

FIGS. 8A to 8F contain a partial DNA sequence of a gene coding for protein HMW3 (SEQ ID NO: 7);

FIGS. 9A to 9F contain a partial DNA sequence of a gene coding for protein HMW4 (SEQ ID NO: 8); and FIGS. 10A to 10L contain a comparison table for the derived amino acid sequence for proteins HMW1 (SEQ ID NO:2), HMW2 (SEQ ID NO:4), HMW3 (SEQ ID NO:9) and HMW4 (SEQ ID NO:10).

GENERAL DESCRIPTION OF INVENTION

Figure 5A:
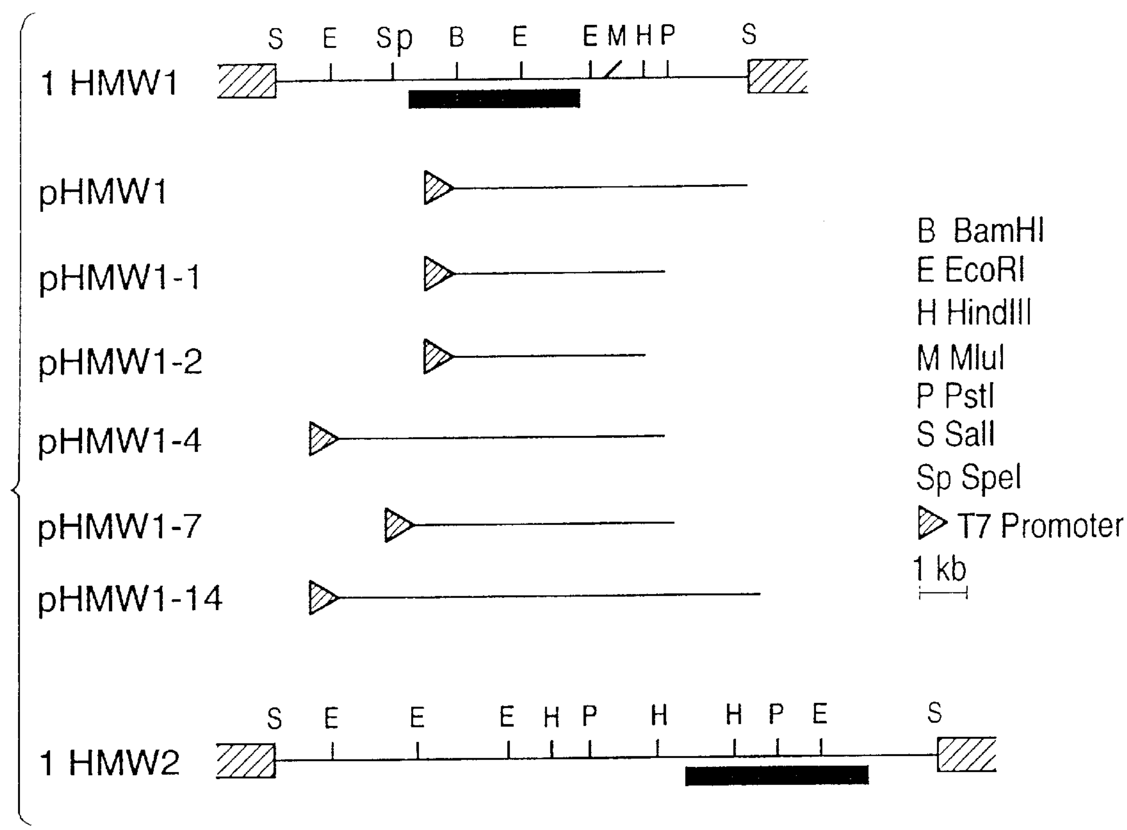
FIG. 5A shows restriction maps of representative recombinant phages which contained the HMW1 or HMW2 structural genes, the locations of the structural genes being indicated by the shaded bars. In the recombinant phage, transcription proceeds from left to right for the HMW1 gene and right to left for the HMW2 gene.

The DNA sequences of the genes coding for HMW1 and HMW2, shown in FIGS. 1 and 3 respectively, were shown to be about 80% identical, with the first 1259 base pairs of the genes being identical. The derived amino acid sequences of the two HMW proteins, shown in FIGS. 2 and 4 respectively, are about 70% identical. Furthermore, the encoded proteins are antigenically related to the filamentous hemagglutinin surface protein of *Bordetella pertussis*. A monoclonal antibody prepared against filamentous hemagglutinin (FHA) of *Bordetella pertussis* was found to recognize both of the high molecular weight proteins. This data suggests that the HMW and FHA proteins may serve similar biological functions. The derived amino acid sequences of the HMW1 and HMW2 proteins show sequence similarity to that for the FHA protein. It has further been shown that these antigenically-related proteins are produced by the majority of the non-typeable strains of Haemophilus. Antisera raised against the protein expressed by the HMW1 gene recognizes both the HMW2 protein and the *B. pertussis* FHA. The present invention includes an isolated and purified high molecular weight protein of non-typeable haemophilus which is antigenically related to the *B. Pertussis* FHA, which may be obtained from natural sources or produced recombinantly.

A phage genomic library of a known strain of non-typeable Haemophilus was prepared by standard methods and the library was screened for clones expressing high molecular weight proteins, using a high titre antiserum against HMW's. A number of strongly reactive DNA clones were plaque-purified and sub-cloned into a T7 expression plasmid. It was found that they all expressed either one or the other of the two high-molecular-weight proteins designated HMW1 and HMW2, with apparent molecular weights of 125 and 120 kDa, respectively, encoded by open reading frames of 4.6 kb and 4.4 kb, respectively.

Representative clones expressing either HMW1 or HMW2 were further characterized and the genes isolated, purified and sequenced. The DNA sequence of HMW1 is shown in FIG. 1 and the corresponding derived amino acid sequence in FIG. 2. Similarly, the DNA sequence of HMW2 is shown in FIG. 3 and the corresponding derived amino acid sequence in FIG. 4. Partial purification of the isolated proteins and N-terminal sequence analysis indicated that the expressed proteins are truncated since their sequence starts at residue number 442 of both full length HMW1 and HMW2 gene products.

Subcloning studies with respect to the hmw1 and hmw2 genes indicated that correct processing of the HMW proteins required the products of additional downstream genes. It has been found that both the hmw1 and hmw2 genes are flanked by two additional downstream open reading frames (ORFs), designated b and c, respectively, (see FIGS. 6 and 7).

The b ORFs are 1635 bp in length, extending from nucleotides 5114 to 6748 in the case of hmw1 and nucleotides 5375 to 7009 in the case of hmw2, with their derived amino acid sequences 99% identical. The derived amino acid sequences demonstrate similarity with the derived amino acid sequences of two genes which encode proteins required for secretion and activation of hemolysins of *P. mirabilis* and *S. marcescens*.

The c ORFs are 1950 bp in length, extending from nucleotides 7062 to 9011 in the case of hmw1 and nucleotides 7249 to 9198 in the case of hmw2, with their derived amino acid sequences 96% identical. The hmw1 c ORF is preceded by a series of 9 bp direct tandem repeats. In plasmid subclones, interruption of the hmw1 b or c ORF results in defective processing and secretion of the hmw1 structural gene product.

The two high molecular weight proteins have been isolated and purified and shown to be partially protective against otitis media in chinchillas and to function as adhesins. These results indicate the potential for use of such high molecular proteins and structurally-related proteins of other non-typeable strains of *Haemophilus influenzae* as components in non-typeable *Haemophilus influenzae* vaccines.

Since the proteins provided herein are good cross-reactive antigens and are present in the majority of non-typeable Haemophilus strains, it is evident that these HMW proteins may become integral constituents of a universal Haemophilus vaccine. Indeed, these proteins may be used not only as protective antigens against otitis, sinusitis and bronchitis caused by the non-typeable Haemophilus strains, but also may be used as carriers for the protective Hib polysaccharides in a conjugate vaccine against meningitis. The proteins also may be used as carriers for other antigens, haptens and polysaccharides from other organisms, so as to induce immunity to such antigens, haptens and polysaccharides.

The nucleotide sequences encoding two high molecular weight proteins of a different non-typeable Haemophilus strain (designated HMW3 and HMW4) have been largely elucidated, and are presented in FIGS. 8 and 9. HMW3 has an apparent molecular weight of 125 kDa while HMW4 has an apparent molecular weight of 123 kDa. These high molecular weight proteins are antigenically related to the HMW1 and HMW2 proteins and to FHA. Sequence analysis of HMW3 is approximately 85% complete and of HMW4 95% complete, with short stretches at the 5'-ends of each gene remaining to be sequenced.

FIG. 10 contains a multiple sequence comparison of the derived amino acid sequences for the four high molecular weight proteins identified herein. As may be seen from this comparison, stretches of identical peptide sequence may be found throughout the length of the comparison, with HMW3 more closely resembling HMW1 and HMW4 more closely resembling HMW2. This information is highly suggestive of a considerable sequence homology between high molecular weight proteins from various non-typeable Haemophilus strains.

In addition, mutants of non-typeable *H. influenzae* strains that are deficient in expression of HMW1 or HMW2 or both have been constructed and examined for their capacity to adhere to cultured human epithelial cells. The hmw1 and hmw2 gene clusters have been expressed in *E. coli* and have been examined for in vitro adherence. The results of such experimentation demonstrate that both HMW1 and HMW2 mediate attachment and hence are adhesins and that this function is present even in the absence of other *H. influenzae* surface-structures.

With the isolation and purification of the high molecular weight proteins, the inventors are able to determine the major protective epitopes by conventional epitope mapping and synthesize peptides corresponding to these determinants to be incorporated in fully synthetic or recombinant vaccines. Accordingly, the invention also comprises a synthetic peptide having an amino acid sequence corresponding to at least one protective epitope of a high molecular weight protein of a non-typeable *Haemophilus influenzae*. Such peptides are of varying length that constitute portions of the high-molecular-weight proteins, that can be used to induce immunity, either directly or as part of a conjugate, against the relative organisms and thus constitute vaccines for protection against the corresponding diseases.

The present invention also provides any variant or fragment of the proteins that retains the potential immunological ability to protect against disease caused by non-typeable Haemophilus strains. The variants may be constructed by partial deletions or mutations of the genes and expression of the resulting modified genes to give the protein variations.

EXAMPLES

Example 1

Non-typeable *H. influenzae* strains 5 and 12 were isolated in pure culture from the middle ear fluid of children with acute otitis media. Chromosomal DNA from strain 12, providing genes encoding proteins HMW1 and HMW2, was prepared by preparing Sau3A partial restriction digests of chromosomal DNA and fractionating on sucrose gradients. Fractions containing DNA fragments in the 9 to 20 kbp range were pooled and a library was prepared by ligation into λEMBL3 arms. Ligation mixtures were packaged in vitro and plate-amplified in a P2 lysogen of *E. coli* LE392.

For plasmid subcloning studies, DNA from a representative recombinant phage was subcloned into the T7 expression plasmid pT7-7, containing the T7 RNA polymerase promoter Φ10, a ribosome-binding site and the translational start site for the T7 gene 10 protein upstream from a multiple cloning site (see FIG. 5B).

DNA sequence analysis was performed by the dideoxy method and both strands of the HMW1 gene and a single strand of the HMW2 gene were sequenced.

Western immunoblot analysis was performed to identify the recombinant proteins being produced by reactive phage clones. Phage lysates grown in LE392 cells or plaques picked directly from a lawn of LE392 cells on YT plates were solubilized in gel electrophoresis sample buffer prior to electrophoresis. Sodium dodecyl sulfate (SDS)-polyacrylamide gel electrophoresis was performed on 7.5% or 11% polyacrylamide modified Lapmmli gels. After transfer of the proteins to nitrocellulose sheets, the sheets were probed sequentially with an *E. coli*-absorbed human serum sample containing high-titer antibody to the high-molecular-weight proteins and then with alkaline phosphatase-conjugated goat anti-human immunoglobulin G (IgG) second antibody. Sera from healthy adults contains high-titer antibody directed against surface-exposed high-molecular-weight proteins of non-typeable *H. influenzae*. One such serum sample was used as the screening antiserum after having been extensively absorbed with LE392 cells.

To identify recombinant proteins being produced by *E. coli* transformed with recombinant plasmids, the plasmids of interest were used to transform *E. coli* BL21 (DE3)/pLysS. The transformed strains were grown to an $A_{600}$ of 0.5 in L broth containing 50 $\mu$g of ampicillin per ml. IPTG was then added to 1 mM. One hour later, cells were harvested, and a sonicate of the cells was prepared. The protein concentrations of the samples were determined by the bicinchoninic acid method. Cell sonicates containing 100 $\mu$g of total protein were solubilized in electrophoresis sample buffer, subjected to SDS-polyacrylamide gel electrophoresis, and transferred to nitrocellulose. The nitrocellulose was then probed sequentially with the *E. coli*-absorbed adult serum sample and then with alkaline phosphatase-conjugated goat anti-human IgG second antibody.

Western immunoblat analysis also was performed to determine whether homologous and heterologous non-typeable *H. influenzae* strains expressed high-molecular-weight proteins antigenically related to the protein encoded by the cloned HMW1 gene (rHMW1). Cell sonicates of bacterial cells were solubilized in electrophoresis sample buffer, subjected to SDS-polyacrylamide gel electrophoresis, and transferred to nitrocellulose. Nitrocellulose was probed sequentially with polyclonal rabbit rHMW1 antiserum and then with alkaline phosphatase-conjugated goat anti-rabbit IgG second antibody.

Finally, Western immunoblot analysis was performed to determine whether non-typeable Haemophilus strains expressed proteins antigenically related to the filamentous hemagglutinin protein of *Bordetella pertussis*. Monoclonal antibody X3C, a murine immunoglobulin G (IgG) antibody which recognizes filamentous hemagglutinin, was used to probe cell sonicates by Western blot. An alkaline phosphatase-conjugated goat anti-mouse IgG second antibody was used for detection.

To generate recombinant protein antiserum, *E. coli* BL21 (DE3)/pLysS was transformed with pHMW1-4, and expression of recombinant protein was induced with IPTG, as described above. A cell sonicate of the bacterial cells was prepared and separated into a supernatant and pellet fraction by centrifugation at 10,000×g for 30 min. The recombinant protein fractionated with the pellet fraction. A rabbit was subcutaneously immunized on biweekly schedule with 1 mg of protein from the pellet fraction, the first dose given with Freund's complete adjuvant and subsequent doses with Freund's incomplete adjuvant. Following the fourth injection, the rabbit was bled. Prior to use in the Western blot assay, the antiserum was absorbed extensively with sonicates of the host *E. coli* strain transformed with cloning vector alone.

To assess the sharing of antigenic determinants between HMW1 and filamentous hemagglutinin, enzyme-linked immunosorbent assay (ELISA) plates (Costar, Cambridge, Mass.) were coated with 60 $\mu$l of a 4-ug/ml solution of filamentous hemagglutinin in Dulbecco's phosphate-buffered saline per well for 2 h at room temperature. Wells were blocked for 1 h with 1% bovine serum albumin in Dulbecco's phosphate-buffered saline prior to addition of serum dilutions. rHMW1 antiserum was serially diluted in 0.1% Brij (Sigma, St. Louis, Mo.) in Dulbecco's phosphate-buffered saline and incubated for 3 h at room temperature. After being washed, the plates were incubated with peroxidase-conjugated goat anti-rabbit lgG antibody (Bio-Rad) for 2 h at room temperature and subsequently developed with 2,2'-azino-bis(3-ethylbenzthiazoline-6-sulfonic acid) (Sigma) at a concentration of 0.54 in mg/ml in 0.1 M sodium citrate buffer, pH 4.2, containing 0.03% $H_2O_2$. Absorbances were read on an automated ELISA reader.

Recombinant phage expressing HMW1 or HMW2 were recovered as follows. The non-typeable *H. influenzae* strain 12 genomic library was screened for clones expressing high-molecular-weight proteins with an *E. coli*-absorbed human serum sample containing a high titer of antibodies directed against the high-molecular-weight proteins.

Numerous strongly reactive clones were identified along with more weakly reactive ones. Twenty strongly reactive clones were plaque-purified and examined by Western blot for expression of recombinant proteins. Each of the strongly reactive clones expressed one of two types of high-molecular-weight proteins, designated HMW1 and HMW2. The major immunoreactive protein bands in the HMW1 and HMW2 lysates migrated with apparent molecular masses of 125 and 120 kDa, respectively. In addition to the major bands, each lysate contained minor protein bands of higher apparent molecular weight. Protein bands seen in the HMW2 lysates at molecular masses of less than 120 kDa were not regularly observed and presumably represent proteolytic degradation products. Lysates of LE392 infected with the λEMBL3 cloning vector alone were non-reactive when immunologically screened with the same serum sample. Thus, the observed activity was not due to cross-reactive *E. coli* proteins or λEBL3-encoded proteins. Furthermore, the recombinant proteins were not simply binding immunoglobulin nonspecifically, since the proteins were not reactive with the goat anti-human IgG conjugate alone, with normal rabbit sera, or with serum from a number of healthy young infants.

Representative clones expressing either the HMW1 or HMW2 recombinant proteins were characterized further. The restriction maps of the two phage types were different from each other, including the regions encoding the HMW1 and HMW2 structural genes. FIG. 5A shows restriction maps of representative recombinant phage which contained the HMW1 or HMW2 structural genes. The locations of the structural genes are indicated by the shaded bars.

HMW1 plasmid subclones were constructed by using the T7 expression plasmid T7-7 (FIGS. 5A and B). HMW2 plasmid subclones also were constructed, and the results with these latter subclones were similar to those observed with the HMW1 constructs.

The approximate location and direction of transcription of the HMW1 structure gene were initially determined by using plasmid pHMW1 (FIG. 5A). This plasmid was constructed by inserting the 8.5-kb BamHI-SalI fragment from λHMW1 into BamHI- and SalI-cut pT7-7. *E. coli* transformed with pHMW1 expressed an immunoreactive recombinant protein with an apparent molecular mass of 115 kDa, which was strongly inducible with IPTG. This protein was significantly smaller than the 125-kDa major protein expressed by the parent phage, indicating that it either was being expressed as a fusion protein or was truncated at the carboxy terminus.

To more precisely localize the 3' end of the structural gene, additional plasmids were constructed with progressive deletions from the 3' end of the pHMW1 construct. Plasmid pHMW1-1 was constructed by digestion of pHMW1 with PstI, isolation of the resulting 8.8-kb fragment, and religation. Plasmid pHMW1-2 was constructed by digestion of pHMW1 with HindIII, isolation of the resulting 7.5-kb fragment, and religation. *E. coli* transformed with either plasmid pHMW1-1 or pHMW1-2 also expressed an immunoreactive recombinant protein with an apparent molecular mass of 115 kDa. These results indicated that the 3' end of the structural gene was 5' of the HindIII site.

To more precisely localize the 5' end of the gene, plasmids pHMW1-4 and pHMW1-7 were constructed. Plasmid pHMW1-4 was constructed by cloning the 5.1-kb BamHI-HindIII fragment from λHMW1 into a pT7-7-derived plasmid containing the upstream 3.8-kb EcoRI-BamHi fragment. *E. coli* transformed with pHMW1-4 expressed an immunoreactive protein with an apparent molecular mass of approximately 160 kDa. Although protein production was inducible with IPTG, the levels of protein production in these transformants were substantially lower than those with the pHMW1-2 transf ormants described above. Plasmid pHMW1-7 was constructed by digesting pHMW1-4 with NdeI and SpeI. The 9.0-kbp fragment generated by this double digestion was isolated, blunt ended, and religated. *E. coli* transformed with pHMW1-7 also expressed an imunoreactive protein with an apparent molecular mass of 160 kDa, a protein identical in size to that expressed by the pHMW1-4 transformants. The result indicated that the initiation codon for the HMW1 structural gene was 3' of the SpeI site. DNA sequence analysis confirmed this conclusion.

As noted above, the λHMW1 phage clones expressed a major immunoreactive band of 125 kDa, whereas the HMW1 plasmid clones pHMW1-4 and pHMW1-7, which contained what was believed to be the full-length gene, expressed an immunoreactive protein of approximately 160 kDa. This size discrepancy was disconcerting. One possible explanation was that an additional gene or genes necessary for correct processing of the HMW1 gene product were deleted in the process of subcloning. To address this possibility, plasmid pHMW1-14 was constructed. This construct was generated by digesting pHMW1 with NdeI and MluI and inserting the 7.6-kbp NdeI-MluI fragment isolated from pHMW1-4. Such a construct would contain the full-length HMW1 gene as well as the DNA 3' of the HMW1 gene which was present in the original HMW1 phage. *E. coli* transformed with this plasmid expressed major immunoreactive proteins with apparent molecular masses of 125 and 160 kDa as well as additional degradation products. The 125- and 160-kDa bands were identical to the major and minor immunoreactive bands detected in the HMW1 phage lysates. Interestingly, the pHMW1-14 construct also expressed significant amounts of protein in the uninduced condition, a situation not observed with the earlier constructs.

The relationship between the 125- and 160-kDa proteins remains somewhat unclear. Sequence analysis, described below, reveals that the HMW1 gene would be predicted to encode a protein of 159 kDa. It is believed that the 160-kDa protein is a precursor form of the mature 125-kDa protein, with the conversion from one protein to the other being dependent on the products of the two downstream genes.

Sequence analysis of the HMW1 gene (FIG. 1) revealed a 4,608-bp open reading frame (ORF), beginning with an ATG codon at nucleotide 351 and ending with a TAG stop codon at nucleotide 4959. A putative ribosome-binding site with the sequence AGGAG begins 10 bp upstream of the putative initiation codon. Five other inframe ATG codons are located within 250 bp of the beginning of the ORF, but none of these is preceded by a typical ribosome-binding site. The 5'-flanking region of the ORF contains a series of direct tandem repeats, with the 7-bp sequence ATCTTTC repeated 16 times. These tandem repeats stop 100 bp 5' of the putative initiation codon. An 8-bp inverted repeat characteristic of a rho-independent transcriptional terminator is present, beginning at nucleotide 4983, 25 bp 3' of the presumed translational stop. Multiple termination codons are present in all three reading frames both upstream and downstream of the ORF. The derived amino acid sequence of the protein encoded by the HMW1 gene (FIG. 2) has a molecular weight of 159,000, in good agreement with the apparent molecular weights of the proteins expressed by the HMW1-4 and HMW1-7 transformants. The derived amino acid sequence of the amino terminus does not demonstrate the characteristics of a typical signal sequence. The BamHI site used in generation of pHMW1 comprises bp 1743 through 1748 of the nucleotide sequence. The ORF downstream of the BamHI site would be predicted to encode a protein of 111 kDa, in good agreement with the 115 kDa estimated for the apparent molecular mass of the pHMW1-encoded fusion protein.

The sequence of the HMW2 gene (FIG. 3) consists of a 4,431-bp ORF, beginning with an ATG codon at nucleotide 352 and ending with a TAG stop codon at nucleotide 4783. The first 1,259 bp of the ORF of the HMW2 gene are identical to those of the HMW1 gene. Thereafter, the sequences begin to diverge but are 80% identical overall. With the exception of a single base addition at nucleotide 93 of the HHW2 sequence, the 5'-flanking regions of the HMW1 and HMW2 genes are identical for 310 bp upstream from the respective initiation codons. Thus, the HMW2 gene is preceded by the same set of tandem repeats and the same putative ribosome-binding site which lies 5' of the HMW1 gene. A putative transcriptional terminator identical to that identified 3' of the HMW1 ORF is noted, beginning at nucleotide 4804. The discrepancy in the lengths of the two genes is principally accounted for by a 186-bp gap in the HMW2 sequence, beginning at nucleotide position 3839. The derived amino acid sequence of the protein encoded by the HMW2 gene (FIG. 4) has a molecular weight of 155,000 and is 71% identical with the derived amino acid sequence of the HMW1 gene.

The derived amino acid sequences of both the HMW1 and HMW2 genes (FIGS. 2 and 4) demonstrated sequence similarity with the derived amino acid sequence of filamentous hemagglutinin of *Bordetella pertussis*, a surface-associated protein of this organism. The initial and optimized TFASTA scores for the HMW1-filamentous hemagglutinin sequence comparison were 87 and 186, respectively, with a word size of 2. The z score for the comparison was 45.8. The initial and optimized TFASTA scores for the HMW2-filamentous hemagglutinin sequence comparison were 68 and 196, respectively. The z score for the latter comparison was 48.7. The magnitudes of the initial and optimized TFASTA scores and the z scores suggested that a biologically significant relationship existed between the HMW1 and HMW2 gene products and filamentous hemagglutinin. When the derived amino acid sequences of HNW1, HMW2, and filamentous hemagglutinin genes were aligned and compared, the similarities were most notable at the amino-terminal ends of the three sequences. Twelve of the first 22 amino acids in the predicted peptide sequences were identical. In additional, the sequences demonstrated a common five-amino-acid stretch, Asn-Pro-Asn-Gly-Ile, and several shorter stretches of sequence identity within the first 200 amino acids.

Example 2

To further explore the HMW1-filamentous hemagglutinin relationship, the ability of antiserum prepared against the HMW1-4 recombinant protein (rHMW1) to recognize purified filamentous hemagglutinin was assessed. The rHMW1 antiserum demonstrated ELISA reactivity with filamentous hemagglutinin in a dose-dependent manner. Preimmune rabbit serum had minimal reactivity in this assay. The rHMW1 antiserum also was examined in a Western blot assay and demonstrated weak but positive reactivity with purified filamentous hemagglutinin in this system also.

To identify the native Haemophilus protein corresponding to the HMW1 gene product and to determine the extent to which proteins antigenically related to the HMW1 cloned gene product were common among other non-typeable *H. influenzae* strains, a panel of Haemophilus strains was screened by Western blot with the rHMW1 antiserum. The antiserum recognized both a 125- and a 120-kDa protein band in the homologous strain 12, the putative mature protein products of the HMW1 and HMW2 genes, respectively.

When used to screen heterologous non-typeable *H. influenzae* strains, rHMW1 antiserum recognized high-molecular-weight proteins in 75% of 125 epidemiologically unrelated strains. In general, the antiserum reacted with one or two protein bands in the 100- to 150-kDa range in each of the heterologous strains in a pattern similar but not identical to that seen in the homologous strain.

Monoclonal antibody X3C is a imurine IgG antibody directed against the filamentous hemagglutinin protein of *B.*

*pertussis*. This antibody can inhibit the binding of *B. pertussis* cells to Chinese hamster ovary cells and HeLa cells in culture and will inhibit hemagglutination of erythrocytes by purified filamentous hemagglutinin. A Western blot assay was performed in which this monoclonal antibody was screened against the same panel of non-typeable *H. influenzae* strains discussed above. Monoclonal antibody X3C recognized both the high-molecular-weight proteins in non-typeable *H. influenzae* strain 12 which were recognized by the recombinant-protein antiserum. In addition, the monoclonal antibody recognized protein bands in a subset of heterologous non-typeable *H. influenzae* strains which were identical to those recognized by the recombinant-protein antiserum. On occasion, the filamentous hemagglutinin monoclonal antibody appeared to recognize only one of the two bands which had been recognized by the recombinant-protein antiserum. Overall, monoclonal antibody X3C recognized high-molecular-weight protein bands identical to those recognized by the rHMWI antiserum in approximately 35% of our collection of non-typeable *H. influenze* strains.

Example 3

Mutants deficient in expression of HMW1, MW2 or both proteins were constructed to examine the role of these proteins in bacterial adherence. The following strategy was employed. pHMW1-14 (see Example 1, FIG. 5A) was digested with BamHI and then ligated to a kanamycin cassette isolated on a 1.3-kb Bamhl fragment from pUC4K. The resultant plasmid (pHMW1-17) was linearized by digestion with XbaI and transformed into non-typeable *H. influenzae* strain 12, followed by selection for kanamycin resistant colonies. Southern analysis of a series of these colonies demonstrated two populations of transformants, one with. an insertion in the HMW1 structural gene and the other with an insertion in the HMW2 structural gene. One mutant from each of these classes was selected for further studies.

Mutants deficient in expression of both proteins were recovered using the following protocol. After deletion of the 2.1-kb fragment of DNA between two EcoRI sites spanning the 3'-portion of the HMW1 structural gene in pHMW-15, the kanamycin cassette from pUC4K was inserted as a 1.3-kb EcoRl fragment. The resulting plasmid (pHMW1-16) was linearized by digestion with XbaI and transformed into strain 12, followed again by selection for kanamycin resistant colonies. Southern analysis of a representative sampling of these colonies demonstrated that in seven of eight cases, insertion into both the HMW1 and MW2 loci had occurred. One such mutant was selected for further studies.

To confirm the intended phenotypes, the mutant strains were examined by Western blot analysis with a polyclonal antiserum against recombinant HMW1 protein. The parental strain expressed both the 125-kD HMW1 and the 120-kD HMW2 protein. In contrast, the HMW2$^-$ mutant failed to express the 120-kD protein, and the HMW1 mutant failed to express the 125-kD protein. The double mutant lacked expression of either protein. On the basis of whole cell lysates, outer membrane profiles, and colony morphology, the wild type strain and the mutants were otherwise identical with one another. Transmission electron microscopy demonstrated that none of the four strains expressed pili.

The capacity of wild type strain 12 to adhere to Chang epithelial cells was examined. In such assays, bacteria were inoculated into broth and allowed to grow to a density of $-2\times10^9$ cfu/ml. Approximately $2\times10^7$ cfu were inoculated onto epithelial cell monolayers, and plates were gently centrifuged at 165×g for 5 minutes to facilitate contact between bacteria and the epithelial surface. After incubation for 30 minutes at 37° C. in 5% $CO_2$, monolayers were rinsed 5 times with PBS to remove nonadherent organisms and were treated with trypsin-EDTA (0.05% trypsin, 0.5% EDTA) in PBS to release them from the plastic support. Well contents were agitated, and dilutions were plated on solid medium to yield the number of adherent bacteria per monolayer. Percent adherence was calculated by dividing the number of adherent cfu per monolayer by the number of inoculated cfu.

As depicted in Table 1 below (the Tables appear at the end of the descriptive text), this strain adhered quite efficiently, with nearly 90% of the inoculum binding to the monolayer. Adherence by the mutant expressing HMW1 but not HMW2 (HMW2$^-$) was also quite efficient and comparable to that by the wild type strain. In contrast, attachment by the strain expressing HMW2 but deficient in expression of HMW1 (HMW1$^-$) was decreased about 15-fold relative to the wild type. Adherence by the double mutant (HMW1$^-$/HMW2$^-$) was decreased even further, approximately 50-fold compared with the wild type and approximately 3-fold compared with the HMW1 mutant. Considered together, these results suggest that both the HMW1 protein and the, HMW2 protein influence attachment to Chang epithelial cells. Interestingly, optimal adherence to this cell line appears to require HMW1 but not HMW2.

Example 4

Using the plasmids pHMW1-16 and pHMW1-17 (see Example 3) and following a scheme similar to that employed with strain 12 as described in Example 3, three non-typeable Haemophilus strain 5 mutants were isolated, including one with the kanamycin gene inserted into the hmw1-like (designated hmw3) locus, a second with an insertion in the hmw2-like (designated hmw4) locus, and a third with insertions in both loci. As predicted, Western immunoblot analysis demonstrated that the mutant with insertion of the kanamycin cassette into the hmw1-like locus had lost expression of the HMW3 125-kD protein, while the mutant with insertion into the hmw2-like locus failed to express the -HMW4 123-kD protein. The mutant with a double insertion was unable to express either of the high molecular weight proteins.

As shown in Table 1 below, wild type strain 5 demonstrated high level adherence, with almost 80% of the inoculum adhering per monolayer. Adherence by the mutant deficient in expression of the HMW2-like protein was also quite high. In contrast, adherence by the mutant unable to express the, HMW1-like protein was reduced about 5-fold relative to the wild type, and attachment by the double mutant was diminished even further (approximately 25-fold). Examination of Giemsa-stained samples confirmed these observations (not shown). Thus, the results with strain 5 corroborate the findings with strain 12 and the HMW1 and HMW2 proteins.

Example 5

To confirm an adherence function for the HMW1 and HMW2 proteins and to examine the effect of HMW1 and HMW2 independently of other *H. influenzae* surface structures, the hmw1 and the hmw2 gene clusters were introduced into *E. coli* DH5α, using plasmids pHMW1-14 and pHMW2-21, respectively. As a control, the cloning vector, pT7-7, was also transformed into *E. coli* DH5α. Western blot analysis demonstrated that *E. coli* DH5α containing the hmw1 genes expressed a 125 kDa protein, while the same strain harboring the hmw2 genes expressed a 120-kDa protein. *E. coli* DH5α containing pT7-7 failed to react with antiserum against recombinant HMW1. Transmission electron microscopy revealed no pili or other surface appendages on any of the *E. coli* strains.

Adherence by the *E. coli* strains was quantitated and compared with adherence by wild type non-typeable *H.*

*influenzae* strain 12. As shown in Table 2 below, adherence by *E. coli* DH5α containing vector alone was less than 1% of that for strain 12. In contrast, *E. coli* DH5α harboring the hmw1 gene cluster demonstrated adherence levels comparable to those for strain 12. Adherence by *E. coli* DH5α containing the hmw2 genes was approximately 6-fold lower than attachment by strain 12 but was increased 20-fold over adherence by *E. coli* DH5α with pT7-7 alone. These results indicate that the HMW1 and HMW2 proteins are capable of independently mediating attachment to Chang conjunctival cells. These results are consistent with the results with the *H. influenzae* mutants reported in Examples 3 and 4, providing further evidence that, with Chang epithelial cells, HMW1 is a more efficient adhesin than is HMW2.

Experiments with *E. coli* HB101 harboring pT7-7, pHMW1-14, or pHMW2-21 confirmed the results obtained with the DH5α derivatives (see Table 2).

Example 6

HMW1 and HMW2 were isolated and purified from non-typeable *H. influenzae* (NTHI) strain 12 in the following manner. Non-typeable Haemophilus bacteria from frozen stock culture were streaked onto a chocolate plate and grown overnight at 37° C. in an incubator with 5% $CO_2$. 50 ml starter culture of brain heart infusion (BHI) broth, supplemented with 10 μg/ml each of hemin and NAD was inoculated with growth on chocolate plate. The starter culture was grown until the optical density (O.D. –600 nm) reached 0.6 to 0.8 and then the bacteria in the starter culture was used to inoculate six 500 ml flasks of supplemented BHI using 8 to 10 ml per flask. The bacteria were grown in 500 ml flasks for an additional 5 to 6 hours at which time the O.D. was 1.5 or greater. Cultures were centrifuged at 10,000 rpm for 10 minutes.

Bacterial pellets were resuspended in a total volume of 250 ml of an extraction solution comprising 0.5 M NaCl, 0.01 M $Na_2EDTA$, 0.01 M Tris 50 μM 1,10-phenanthroline, pH 7.5. The cells were not sonicated or otherwise disrupted. The resuspended cells were allowed to sit on ice at 0° C. for 60 minutes. The resuspended cells were centrifuged at 10,000 rpm for 10 minutes at 4° C. to remove the majority of intact cells and cellular debris. The supernatant was collected and centrifuged at 100,000×g for 60 minutes at 4° C. The supernatant again was collected and dialyzed overnight at 4° C. against 0.01 M sodium phosphate, pH 6.0.

The sample was centrifuged at 10,000 rpm for 10 minutes at 4° C. to remove insoluble debris precipitated from solution during dialysis. The supernatant was applied to a 10 ml CM Sepharose column which has been pre-equilibrated with 0.01 M sodium phosphate, pH 6. Following application to this column, the column was washed with 0.01 M sodium phosphate. Proteins were elevated from the column with a 0–0.5M KCl gradient in 0.01 M Na phosphate, pH 6 and fractions were collected for gel examination. Coomassie gels of column fractions were carried out to identify those fractions containing high molecular weight proteins. The fractions containing high molecular weight proteins were pooled and concentrated to a 1 to 3 ml volume in preparation for application of sample to gel filtration column.

A Sepharose CL-4B gel filtration column was equilibrated with phosphate-buffered saline, pH 7.5. The concentrated high molecular weight protein sample was applied to the gel filtration column and column fractions were collected. Coomassie gels were performed on the column fractions to identify those containing high molecular weight proteins. The column fractions containing high molecular weight proteins were pooled.

The proteins were tested to determine whether they would protect against experimental otitis media caused by the homologous strain.

Chinchillas received three monthly subcutaneous injections with 40 μg of an HMW1–HMW2 protein mixture in Freund's adjuvant. One month after the last injection, the animals were challenged by intrabullar inoculation with 300 cfu of NTHI strain 12.

Infection developed in 5 of 5 control animals versus 5 of 10 immunized animals. Among infected animals, geometric mean bacterial counts in middle ear fluid 7 days post-challenge were $7.4\times10^6$ in control animals verus $1.3\times10^5$ in immunized animals.

Serum antibody titres following immunization were comparable in uninfected and infected animals. However, infection in immunized animals was uniformly associated with the appearance of bacteria down-regulated in expression of the HMW proteins, suggesting bacterial selection in response to immunologic pressure.

Although this data shows that protection following immunization was not complete, this data suggests the HMW adhesin proteins are potentially important protective antigens which may comprise one component of a multi-component NTHI vaccine.

Example 7

A number of synthetic peptides were derived from HMW1. Antisera then was raised to these peptides. The anti-peptide antisera to peptide HMW1-P5 was shown to recognize HMW1. Peptide HMW1-P5 covers amino acids 1453 to 1481 of HMW1, has the sequence VDEVIEAKRILEKVKDLSDEEREALAKLG (SEQ ID NO:9), and represents bases 1498 to 1576 in FIG. 10.

This finding demonstrates that the DNA sequence and the derived protein is being interpreted in the correct reading frame and that peptides derived from the sequence can be produced which will be immunogenic.

SUMMARY OF DISCLOSURE

In summary of this disclosure, the present invention provides high molecular weight proteins of non-typeable Haemophilus, genes coding for the same and vaccines incorporating such proteins. Modifications are possible within the scope of this invention.

TABLE 1

Effect of mutation of high molecular weight proteins on adherence to Chang epithelial cells by nontypable *H. influenzae*.

| Strain | ADHERENCE* % inoculum | ADHERENCE* relative to wild type† |
|---|---|---|
| Strain 12 derivatives | | |
| wild type | 87.7 ± 5.9 | 100.0 ± 6.7 |
| HMW1-mutant | 6.0 ± 0.9 | 6.8 ± 1.0 |
| HMW2-mutant | 89.9 ± 10.8 | 102.5 ± 12.3 |
| HMW1-/HMW2-mutant | 2.0 ± 0.3 | 2.3 ± 0.3 |
| Strain 5 derivatives | | |
| wild type | 78.7 ± 3.2 | 100.0 ± 4.1 |
| HMW1-like mutant | 15.7 ± 2.6 | 19.9 ± 3.3 |

TABLE 1-continued

Effect of mutation of high molecular weight proteins on adherence to Chang epithelial cells by nontypable *H. influenzae*.

| Strain | ADHERENCE* % inoculum | ADHERENCE* relative to wild type† |
|---|---|---|
| HMW2-like mutant | 103.7 ± 14.0 | 131.7 ± 17.8 |
| double mutant | 3.5 ± 0.6 | 4.4 ± 0.8 |

TABLE 2

Adherence by *E. coli* DH5α and HB101 harboring hmw1 or hmw2 gene clusters.

| Strain* | Adherence relative to *H. influenzae* strain 12† |
|---|---|
| DH5α (pT7-7) | 0.7 ± 0.02 |
| DH5α (pHMW1-14) | 114.2 ± 15.9 |
| DH5α (pHMW2-21) | 14.0 ± 3.7 |
| HB101 (pT7-7) | 1.2 ± 0.5 |
| HB101 (pHMW1-14) | 93.6 ± 15.8 |
| HB101 (pHMW2-21) | 3.6 ± 0.9 |

*The plasmid pHMW1-14 contains the hmw1 gene cluster, while pHMW2-21 contains the hmw2 gene cluster: pT7-7 is the cloning vector used in these constructs.

†Numbers represent the mean (± standard error of the mean) of measurements made in triplicate from representative experiments.

What I claim is:

1. A method for the production of an isolated and purified high molecular weight protein of non-typeable Haemophilus which is HMW1, encoded by a DNA sequence having the nucleic acid sequence recited in SEQ ID No: 1 and having an apparent molecular weight of about 125 kDa, which comprises:

assembling an expression vector containing the nucleic acid sequence recited in SEQ ID No: 1 which encodes the high molecular weight protein, HMW1, and a promoter operatively coupled to said nucleic acid sequence of SEQ ID No: 1 transforming a host cell with the expression vector, expressing the HMW1 protein in the host cell, and isolating and purifying the expressed HMW1 protein.

2. The method of claim 1 wherein said HMW1 protein has the amino acid sequence as set forth in SEQ ID NO:2.

* * * * *

SEQUENCE LISTING

```
(1) GENERAL INFORMATION:

   (iii) NUMBER OF SEQUENCES: 10


(2) INFORMATION FOR SEQ ID NO:1:

     (i) SEQUENCE CHARACTERISTICS:
          (A) LENGTH: 5116 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:1:

ACAGCGTTCT CTTAATACTA GTACAAACCC ACAATAAAAT ATGACAAACA ACAATTACAA      60

CACCTTTTTT GCAGTCTATA TGCAAATATT TTAAAAAATA GTATAAATCC GCCATATAAA     120

ATGGTATAAT CTTTCATCTT TCATCTTTCA TCTTTCATCT TTCATCTTTC ATCTTTCATC     180

TTTCATCTTT CATCTTTCAT CTTTCATCTT TCATCTTTCA TCTTTCATCT TTCATCTTTC     240

ACATGCCCTG ATGAACCGAG GGAAGGGAGG GAGGGGCAAG AATGAAGAGG GAGCTGAACG     300

AACGCAAATG ATAAAGTAAT TTAATTGTTC AACTAACCTT AGGAGAAAAT ATGAACAAGC     360

TATATCGTCT CAAATTCAGC AAACGCCTGA ATGCTTTGGT TGCTGTGTCT GAATTGGCAC     420

GGGGTTGTGA CCATTCCACA GAAAAAGGCA GCGAAAAACC TGCTCGCATG AAAGTGCGTC     480

ACTTAGCGTT AAAGCCACTT TCCGCTATGT TACTATCTTT AGGTGTAACA TCTATTCCAC     540

AATCTGTTTT AGCAAGCGGC TTACAAGGAA TGGATGTAGT ACACGGCACA GCCACTATGC     600

AAGTAGATGG TAATAAAACC ATTATCCGCA ACAGTGTTGA CGATATCATT AATTGGAAAC     660

AATTTAACAT CGACCAAAAT GAAATGGTGC AGTTTTTACA AGAAAACAAC AACTCCGCCG     720

TATTCAACCG TGTTACATCT AACCAAATCT CCCAATTAAA AGGGATTTTA GATTCTAACG     780

GACAAGTCTT TTTAATCAAC CCAAATGGTA TCACAATAGG TAAAGACGCA ATTATTAACA     840

CTAATGGCTT TACGGCTTCT ACGCTAGACA TTTCTAACGA AAACATCAAG GCGCGTAATT     900

TCACCTTCGA GCAAACCAAA GATAAAGCGC TCGCTGAAAT TGTGAATCAC GGTTTAATTA     960

CTGTCGGTAA AGACGGCAGT GTAAATCTTA TTGGTGGCAA AGTGAAAAAC GAGGGTGTGA    1020

TTAGCGTAAA TGGTGGCAGC ATTTCTTTAC TCGCAGGGCA AAAAATCACC ATCAGCGATA    1080
```

-continued

```
TAATAAACCC AACCATTACT TACAGCATTG CCGCGCCTGA AAATGAAGCG GTCAATCTGG   1140
GCGATATTTT TGCCAAAGGC GGTAACATTA ATGTCCGTGC TGCCACTATT CGAAACCAAG   1200
GTAAACTTTC TGCTGATTCT GTAAGCAAAG ATAAAAGCGG CAATATTGTT CTTTCCGCCA   1260
AAGAGGGTGA AGCGGAAATT GGCGGTGTAA TTTCCGCTCA AAATCAGCAA GCTAAAGGCG   1320
GCAAGCTGAT GATTACAGGC GATAAAGTCA CATTAAAAAC AGGTGCAGTT ATCGACCTTT   1380
CAGGTAAAGA AGGGGGAGAA ACTTACCTTG GCGGTGACGA GCGCGGCGAA GGTAAAAAGG   1440
GCATTCAATT AGCAAAGAAA ACCTCTTTAG AAAAAGGCTC AACCATCAAT GTATCAGGCA   1500
AAGAAAAAGG CGGACGCGCT ATTGTGTGGG GCGATATTGC GTTAATTGAC GGCAATATTA   1560
ACGCTCAAGG TAGTGGTGAT ATCGCTAAAA CCGGTGGTTT TGTGGAGACG TCGGGGCATG   1620
ATTTATTCAT CAAAGACAAT GCAATTGTTG ACGCCAAAGA GTGGTTGTTA GACCCGGATA   1680
ATGTATCTAT TAATGCAGAA ACAGCAGGAC GCAGCAATAC TTCAGAAGAC GATGAATACA   1740
CGGGATCCGG GAATAGTGCC AGCACCCCAA AACGAAACAA AGAAAAGACA ACATTAACAA   1800
ACACAACTCT TGAGAGTATA CTAAAAAAAG GTACCTTTGT TAACATCACT GCTAATCAAC   1860
GCATCTATGT CAATAGCTCC ATTAATTTAT CCAATGGCAG CTTAACTCTT TGGAGTGAGG   1920
GTCGGAGCGG TGGCGGCGTT GAGATTAACA ACGATATTAC CACCGGTGAT GATACCAGAG   1980
GTGCAAACTT AACAATTTAC TCAGGCGGCT GGGTTGATGT TCATAAAAAT ATCTCACTCG   2040
GGGCGCAAGG TAACATAAAC ATTACAGCTA AACAAGATAT CGCCTTTGAG AAAGGAAGCA   2100
ACCAAGTCAT TACAGGTCAA GGGACTATTA CCTCAGGCAA TCAAAAAGGT TTTAGATTTA   2160
ATAATGTCTC TCTAAACGGC ACTGGCAGCG GACTGCAATT CACCACTAAA AGAACCAATA   2220
AATACGCTAT CACAAATAAA TTTGAAGGGA CTTTAAATAT TTCAGGGAAA GTGAACATCT   2280
CAATGGTTTT ACCTAAAAAT GAAAGTGGAT ATGATAAATT CAAAGGACGC ACTTACTGGA   2340
ATTTAACCTC CTTAAATGTT TCCGAGAGTG GCGAGTTTAA CCTCACTATT GACTCCAGAG   2400
GAAGCGATAG TGCAGGCACA CTTACCCAGC CTTATAATTT AAACGGTATA TCATTCAACA   2460
AAGACACTAC CTTTAATGTT GAACGAAATG CAAGAGTCAA CTTTGACATC AAGGCACCAA   2520
TAGGGATAAA TAAGTATTCT AGTTTGAATT ACGCATCATT TAATGGAAAC ATTTCAGTTT   2580
CGGGAGGGGG GAGTGTTGAT TTCACACTTC TCGCCTCATC CTCTAACGTC CAAACCCCCG   2640
GTGTAGTTAT AAATTCTAAA TACTTTAATG TTTCAACAGG GTCAAGTTTA AGATTTAAAA   2700
CTTCAGGCTC AACAAAAACT GGCTTCTCAA TAGAGAAAGA TTTAACTTTA AATGCCACCG   2760
GAGGCAACAT AACACTTTTG CAAGTTGAAG GCACCGATGG AATGATTGGT AAAGGCATTG   2820
TAGCCAAAAA AAACATAACC TTTGAAGGAG GTAACATCAC CTTTGGCTCC AGGAAAGCCG   2880
TAACAGAAAT CGAAGGCAAT GTTACTATCA ATAACAACGC TAACGTCACT CTTATCGGTT   2940
CGGATTTTGA CAACCATCAA AAACCTTTAA CTATTAAAAA AGATGTCATC ATTAATAGCG   3000
GCAACCTTAC CGCTGGAGGC AATATTGTCA ATATAGCCGG AAATCTTACC GTTGAAAGTA   3060
ACGCTAATTT CAAAGCTATC ACAAATTTCA CTTTTAATGT AGGCGGCTTG TTTGACAACA   3120
AAGGCAATTC AAATATTTCC ATTGCCAAAG GAGGGGCTCG CTTTAAAGAC ATTGATAATT   3180
CCAAGAATTT AAGCATCACC ACCAACTCCA GCTCCACTTA CCGCACTATT ATAAGCGGCA   3240
ATATAACCAA TAAAAACGGT GATTTAAATA TTACGAACGA AGGTAGTGAT ACTGAAATGC   3300
AAATTGGCGG CGATGTCTCG CAAAAAGAAG GTAATCTCAC GATTTCTTCT GACAAAATCA   3360
ATATTACCAA ACAGATAACA ATCAAGGCAG GTGTTGATGG GGAGAATTCC GATTCAGACG   3420
```

-continued

```
CGACAAACAA TGCCAATCTA ACCATTAAAA CCAAAGAATT GAAATTAACG CAAGACCTAA   3480
ATATTTCAGG TTTCAATAAA GCAGAGATTA CAGCTAAAGA TGGTAGTGAT TTAACTATTG   3540
GTAACACCAA TAGTGCTGAT GGTACTAATG CCAAAAAAGT AACCTTTAAC CAGGTTAAAG   3600
ATTCAAAAAT CTCTGCTGAC GGTCACAAGG TGACACTACA CAGCAAAGTG GAAACATCCG   3660
GTAGTAATAA CAACACTGAA GATAGCAGTG ACAATAATGC CGGCTTAACT ATCGATGCAA   3720
AAAATGTAAC AGTAAACAAC AATATTACTT CTCACAAAGC AGTGAGCATC TCTGCGACAA   3780
GTGGAGAAAT TACCACTAAA ACAGGTACAA CCATTAACGC AACCACTGGT AACGTGGAGA   3840
TAACCGCTCA AACAGGTAGT ATCCTAGGTG GAATTGAGTC CAGCTCTGGC TCTGTAACAC   3900
TTACTGCAAC CGAGGGCGCT CTTGCTGTAA GCAATATTTC GGGCAACACC GTTACTGTTA   3960
CTGCAAATAG CGGTGCATTA ACCACTTTGG CAGGCTCTAC AATTAAAGGA ACCGAGAGTG   4020
TAACCACTTC AAGTCAATCA GGCGATATCG GCGGTACGAT TTCTGGTGGC ACAGTAGAGG   4080
TTAAAGCAAC CGAAAGTTTA ACCACTCAAT CCAATTCAAA AATTAAAGCA ACAACAGGCG   4140
AGGCTAACGT AACAAGTGCA ACAGGTACAA TTGGTGGTAC GATTTCCGGT AATACGGTAA   4200
ATGTTACGGC AAACGCTGGC GATTTAACAG TTGGGAATGG CGCAGAAATT AATGCGACAG   4260
AAGGAGCTGC AACCTTAACT ACATCATCGG GCAAATTAAC TACCGAAGCT AGTTCACACA   4320
TTACTTCAGC CAAGGGTCAG GTAAATCTTT CAGCTCAGGA TGGTAGCGTT GCAGGAAGTA   4380
TTAATGCCGC CAATGTGACA CTAAATACTA CAGGCACTTT AACTACCGTG AAGGGTTCAA   4440
ACATTAATGC AACCAGCGGT ACCTTGGTTA TTAACGCAAA AGACGCTGAG CTAAATGGCG   4500
CAGCATTGGG TAACCACACA GTGGTAAATG CAACCAACGC AAATGGCTCC GGCAGCGTAA   4560
TCGCGACAAC CTCAAGCAGA GTGAACATCA CTGGGGATTT AATCACAATA AATGGATTAA   4620
ATATCATTTC AAAAAACGGT ATAAACACCG TACTGTTAAA AGGCGTTAAA ATTGATGTGA   4680
AATACATTCA ACCGGGTATA GCAAGCGTAG ATGAAGTAAT TGAAGCGAAA CGCATCCTTG   4740
AGAAGGTAAA AGATTTATCT GATGAAGAAA GAGAAGCGTT AGCTAAACTT GGAGTAAGTG   4800
CTGTACGTTT TATTGAGCCA AATAATACAA TTACAGTCGA TACACAAAAT GAATTTGCAA   4860
CCAGACCATT AAGTCGAATA GTGATTTCTG AAGGCAGGGC GTGTTTCTCA AACAGTGATG   4920
GCGCGACGGT GTGCGTTAAT ATCGCTGATA ACGGGCGGTA GCGGTCAGTA ATTGACAAGG   4980
TAGATTTCAT CCTGCAATGA AGTCATTTTA TTTTCGTATT ATTTACTGTG TGGGTTAAAG   5040
TTCAGTACGG GCTTTACCCA TCTTGTAAAA AATTACGGAG AATACAATAA AGTATTTTTA   5100
ACAGGTTATT ATTATG                                                   5116
```

(2) INFORMATION FOR SEQ ID NO:2:

(i) SEQUENCE CHARACTERISTICS:
(A) LENGTH: 1536 amino acids
(B) TYPE: amino acid
(C) STRANDEDNESS: single
(D) TOPOLOGY: linear (ii) MOLECULE TYPE:

(xi) SEQUENCE DESCRIPTION: SEQ ID NO:2:

```
Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
            20                  25                  30

Gly Ser Glu Lys Pro Ala Arg Met Lys Val Arg His Leu Ala Leu Lys
        35                  40                  45
```

-continued

```
Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
        355                 360                 365

Lys Lys Thr Ser Leu Glu Lys Gly Ser Thr Ile Asn Val Ser Gly Lys
    370                 375                 380

Glu Lys Gly Gly Arg Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
            420                 425                 430

Val Asp Ala Lys Glu Trp Leu Leu Asp Phe Asp Asn Val Ser Ile Asn
        435                 440                 445

Ala Glu Thr Ala Gly Arg Ser Asn Thr Ser Glu Asp Asp Glu Tyr Thr
    450                 455                 460
```

-continued

```
Gly Ser Gly Asn Ser Ala Ser Thr Pro Lys Arg Asn Lys Glu Lys Thr
465                 470                 475                 480

Thr Leu Thr Asn Thr Thr Leu Glu Ser Ile Leu Lys Lys Gly Thr Phe
                485                 490                 495

Val Asn Ile Thr Ala Asn Gln Arg Ile Tyr Val Asn Ser Ser Ile Asn
            500                 505                 510

Leu Ser Asn Gly Ser Leu Thr Leu Trp Ser Glu Gly Arg Ser Gly Gly
        515                 520                 525

Gly Val Glu Ile Asn Asn Asp Ile Thr Thr Gly Asp Asp Thr Arg Gly
    530                 535                 540

Ala Asn Leu Thr Ile Tyr Ser Gly Gly Trp Val Asp Val His Lys Asn
545                 550                 555                 560

Ile Ser Leu Gly Ala Gln Gly Asn Ile Asn Ile Thr Ala Lys Gln Asp
                565                 570                 575

Ile Ala Phe Glu Lys Gly Ser Asn Gln Val Ile Thr Gly Gln Gly Thr
            580                 585                 590

Ile Thr Ser Gly Asn Gln Lys Gly Phe Arg Phe Asn Asn Val Ser Leu
        595                 600                 605

Asn Gly Thr Gly Ser Gly Leu Gln Phe Thr Thr Lys Arg Thr Asn Lys
    610                 615                 620

Tyr Ala Ile Thr Asn Lys Phe Glu Gly Thr Leu Asn Ile Ser Gly Lys
625                 630                 635                 640

Val Asn Ile Ser Met Val Leu Pro Lys Asn Glu Ser Gly Tyr Asp Lys
                645                 650                 655

Phe Lys Gly Arg Thr Tyr Trp Asn Leu Thr Ser Leu Asn Val Ser Glu
            660                 665                 670

Ser Gly Glu Phe Asn Leu Thr Ile Asp Ser Arg Gly Ser Asp Ser Ala
        675                 680                 685

Gly Thr Leu Thr Gln Pro Tyr Asn Leu Asn Gly Ile Ser Phe Asn Lys
    690                 695                 700

Asp Thr Thr Phe Asn Val Glu Arg Asn Ala Arg Val Asn Phe Asp Ile
705                 710                 715                 720

Lys Ala Pro Ile Gly Ile Asn Lys Tyr Ser Ser Leu Asn Tyr Ala Ser
                725                 730                 735

Phe Asn Gly Asn Ile Ser Val Ser Gly Gly Gly Ser Val Asp Phe Thr
            740                 745                 750

Leu Leu Ala Ser Ser Ser Asn Val Gln Thr Pro Gly Val Val Ile Asn
        755                 760                 765

Ser Lys Tyr Phe Asn Val Ser Thr Gly Ser Ser Leu Arg Phe Lys Thr
    770                 775                 780

Ser Gly Ser Thr Lys Thr Gly Phe Ser Ile Glu Lys Asp Leu Thr Leu
785                 790                 795                 800

Asn Ala Thr Gly Gly Asn Ile Thr Leu Leu Gln Val Glu Gly Thr Asp
                805                 810                 815

Gly Met Ile Gly Lys Gly Ile Val Ala Lys Lys Asn Ile Thr Phe Glu
            820                 825                 830

Gly Gly Asn Ile Thr Phe Gly Ser Arg Lys Ala Val Thr Glu Ile Glu
        835                 840                 845

Gly Asn Val Thr Ile Asn Asn Asn Ala Asn Val Thr Leu Ile Gly Ser
    850                 855                 860

Asp Phe Asp Asn His Gln Lys Pro Leu Thr Ile Lys Lys Asp Val Ile
865                 870                 875                 880

Ile Asn Ser Gly Asn Leu Thr Ala Gly Gly Asn Ile Val Asn Ile Ala
```

-continued

```
                885                 890                 895

Gly Asn Leu Thr Val Glu Ser Asn Ala Asn Phe Lys Ala Ile Thr Asn
            900                 905                 910

Phe Thr Phe Asn Val Gly Gly Leu Phe Asp Asn Lys Gly Asn Ser Asn
        915                 920                 925

Ile Ser Ile Ala Lys Gly Gly Ala Arg Phe Lys Asp Ile Asp Asn Ser
    930                 935                 940

Lys Asn Leu Ser Ile Thr Thr Asn Ser Ser Ser Thr Tyr Arg Thr Ile
945                 950                 955                 960

Ile Ser Gly Asn Ile Thr Asn Lys Asn Gly Asp Leu Asn Ile Thr Asn
                965                 970                 975

Glu Gly Ser Asp Thr Glu Met Gln Ile Gly Gly Asp Val Ser Gln Lys
            980                 985                 990

Glu Gly Asn Leu Thr Ile Ser Ser Asp Lys Ile Asn Ile Thr Lys Gln
        995                 1000                1005

Ile Thr Ile Lys Ala Gly Val Asp Gly Glu Asn Ser Asp Ser Asp Ala
    1010                1015                1020

Thr Asn Asn Ala Asn Leu Thr Ile Lys Thr Lys Glu Leu Lys Leu Thr
1025                1030                1035                1040

Gln Asp Leu Asn Ile Ser Gly Phe Asn Lys Ala Glu Ile Thr Ala Lys
                1045                1050                1055

Asp Gly Ser Asp Leu Thr Ile Gly Asn Thr Asn Ser Ala Asp Gly Thr
            1060                1065                1070

Asn Ala Lys Lys Val Thr Phe Asn Gln Val Lys Asp Ser Lys Ile Ser
        1075                1080                1085

Ala Asp Gly His Lys Val Thr Leu His Ser Lys Val Glu Thr Ser Gly
    1090                1095                1100

Ser Asn Asn Asn Thr Glu Asp Ser Ser Asp Asn Asn Ala Gly Leu Thr
1105                1110                1115                1120

Ile Asp Ala Lys Asn Val Thr Val Asn Asn Asn Ile Thr Ser His Lys
                1125                1130                1135

Ala Val Ser Ile Ser Ala Thr Ser Gly Glu Ile Thr Thr Lys Thr Gly
            1140                1145                1150

Thr Thr Ile Asn Ala Thr Thr Gly Asn Val Glu Ile Thr Ala Gln Thr
        1155                1160                1165

Gly Ser Ile Leu Gly Gly Ile Glu Ser Ser Ser Gly Ser Val Thr Leu
    1170                1175                1180

Thr Ala Thr Glu Gly Ala Leu Ala Val Ser Asn Ile Ser Gly Asn Thr
1185                1190                1195                1200

Val Thr Val Thr Ala Asn Ser Gly Ala Leu Thr Thr Leu Ala Gly Ser
                1205                1210                1215

Thr Ile Lys Gly Thr Glu Ser Val Thr Thr Ser Ser Gln Ser Gly Asp
            1220                1225                1230

Ile Gly Gly Thr Ile Ser Gly Gly Thr Val Glu Val Lys Ala Thr Glu
        1235                1240                1245

Ser Leu Thr Thr Gln Ser Asn Ser Lys Ile Lys Ala Thr Thr Gly Glu
    1250                1255                1260

Ala Asn Val Thr Ser Ala Thr Gly Thr Ile Gly Gly Thr Ile Ser Gly
1265                1270                1275                1280

Asn Thr Val Asn Val Thr Ala Asn Ala Gly Asp Leu Thr Val Gly Asn
                1285                1290                1295

Gly Ala Glu Ile Asn Ala Thr Glu Gly Ala Ala Thr Leu Thr Thr Ser
            1300                1305                1310
```

```
Ser Gly Lys Leu Thr Thr Glu Ala Ser Ser His Ile Thr Ser Ala Lys
        1315                1320                1325

Gly Gln Val Asn Leu Ser Ala Gln Asp Gly Ser Val Ala Gly Ser Ile
    1330                1335                1340

Asn Ala Ala Asn Val Thr Leu Asn Thr Thr Gly Thr Leu Thr Thr Val
1345                1350                1355                1360

Lys Gly Ser Asn Ile Asn Ala Thr Ser Gly Thr Leu Val Ile Asn Ala
                1365                1370                1375

Lys Asp Ala Glu Leu Asn Gly Ala Ala Leu Gly Asn His Thr Val Val
            1380                1385                1390

Asn Ala Thr Asn Ala Asn Gly Ser Gly Ser Val Ile Ala Thr Thr Ser
        1395                1400                1405

Ser Arg Val Asn Ile Thr Gly Asp Leu Ile Thr Ile Asn Gly Leu Asn
    1410                1415                1420

Ile Ile Ser Lys Asn Gly Ile Asn Thr Val Leu Leu Lys Gly Val Lys
1425                1430                1435                1440

Ile Asp Val Lys Tyr Ile Gln Pro Gly Ile Ala Ser Val Asp Glu Val
                1445                1450                1455

Ile Glu Ala Lys Arg Ile Leu Glu Lys Val Lys Asp Leu Ser Asp Glu
            1460                1465                1470

Glu Arg Glu Ala Leu Ala Lys Leu Gly Val Ser Ala Val Arg Phe Ile
        1475                1480                1485

Glu Pro Asn Asn Thr Ile Thr Val Asp Thr Gln Asn Glu Phe Ala Thr
    1490                1495                1500

Arg Pro Leu Ser Arg Ile Val Ile Ser Glu Gly Arg Ala Cys Phe Ser
1505                1510                1515                1520

Asn Ser Asp Gly Ala Thr Val Cys Val Asn Ile Ala Asp Asn Gly Arg
                1525                1530                1535
```

(2) INFORMATION FOR SEQ ID NO:3:

(i) SEQUENCE CHARACTERISTICS:
(A) LENGTH: 4937 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

```
TAAATATACA AGATAATAAA AATAAATCAA GATTTTTGTG ATGACAAACA ACAATTACAA     60

CACCTTTTTT GCAGTCTATA TGCAAATATT TTAAAAAAAT AGTATAAATC CGCCATATAA    120

AATGGTATAA TCTTTCATCT TTCATCTTTA ATCTTTCATC TTTCATCTTT CATCTTTCAT    180

CTTTCATCTT TCATCTTTCA TCTTTCATCT TTCATCTTTC ATCTTTCATC TTTCATCTTT    240

CACATGAAAT GATGAACCGA GGGAAGGGAG GGAGGGGCAA GAATGAAGAG GGAGCTGAAC    300

GAACGCAAAT GATAAAGTAA TTTAATTGTT CAACTAACCT TAGGAGAAAA TATGAACAAG    360

ATATATCGTC TCAAATTCAG CAAACGCCTG AATGCTTTGG TTGCTGTGTC TGAATTGGCA    420

CGGGGTTGTG ACCATTCCAC AGAAAAAGGC TTCCGCTATG TTACTATCTT TAGGTGTAAC    480

CACTTAGCGT TAAAGCCACT TTCCGCTATG TTACTATCTT TAGGTGTAAC ATCTATTCCA    540

CAATCTGTTT TAGCAAGCGG CTTACAAGGA ATGGATGTAG TACACGGCAC AGCCACTATG    600

CAAGTAGATG GTAATAAAAC CATTATCCGC AACAGTGTTG ACGCTATCAT TAATTGGAAA    660

CAATTTAACA TCGACCAAAA TGAAATGGTG CAGTTTTTAC AAGAAAACAA CAACTCCGCC    720
```

-continued

```
GTATTCAACC GTGTTACATC TAACCAAATC TCCCAATTAA AAGGGATTTT AGATTCTAAC    780
GGACAAGTCT TTTTAATCAA CCCAAATGGT ATCACAATAG GTAAAGACGC AATTATTAAC    840
ACTAATGGCT TTACGGCTTC TACGCTAGAC ATTTCTAACG AAAACATCAA GGCGCGTAAT    900
TTCACCTTCG AGCAAACCAA AGATAAAGCG CTCGCTGAAA TTGTGAATCA CGGTTTAATT    960
ACTGTCGGTA AAGACGGCAG TGTAAATCTT ATTGGTGGCA AAGTGAAAAA CGAGGGTGTG   1020
ATTAGCGTAA ATGGTGGCAG CATTTCTTTA CTCGCAGGGC AAAAAATCAC CATCAGCGAT   1080
ATAATAAACC CAACCATTAC TTACAGCATT GCCGCGCCTG AAAATGAAGC GGTCAATCTG   1140
GGCGATATTT TTGCCAAAGG CGGTAACATT AATGTCCGTG CTGCCACTAT TCGAAACCAA   1200
GGTAAACTTT CTGCTGATTC TGTAAGCAAA GATAAAAGCG GCAATATTGT TCTTTCCGCC   1260
AAAGAGGGTG AAGCGGAAAT TGGCGGTGTA ATTTCCGCTC AAAATCAGCA AGCTAAAGGC   1320
GGCAAGCTGA TGATTACAGG CGATAAAGTC ACATTAAAAA CAGGTGCAGT TATCGACCTT   1380
TCAGGTAAAG AAGGGGGAGA AACTTACCTT GGCGGTGACG AGCGCGGCGA AGGTAAAAAC   1440
GGCATTCAAT TAGCAAAGAA AACCTCTTTA GAAAAAGGCT CAACCATCAA TGTATCAGGC   1500
AAAGAAAAAG GCGGACGCGC TATTGTGTGG GGCGATATTG CGTTAATTGA CGGCAATATT   1560
AACGCTCAAG GTAGTGGTGA TATCGCTAAA ACCGGTGGTT TTGTGGAGAC ATCGGGGCAT   1620
TATTTATCCA TTGACAGCAA TGCAATTGTT AAAACAAAAG AGTGGTTGCT AGACCCTGAT   1680
GATGTAACAA TTGAAGCCGA AGACCCCCTT CGCAATAATA CCGGTATAAA TGATGAATTC   1740
CCAACAGGCA CCGGTGAAGC AAGCGACCCT AAAAAAAATA GCGAACTCAA AACAACGCTA   1800
ACCAATACAA CTATTTCAAA TTATCTGAAA AACGCCTGGA CAATGAATAT AACGGCATCA   1860
AGAAAACTTA CCGTTAATAG CTCAATCAAC ATCGGAAGCA ACTCCCACTT AATTCTCCAT   1920
AGTAAAGGTC AGCGTGGCGG AGGCGTTCAG ATTGATGGAG ATATTACTTC TAAAGGCGGA   1980
AATTTAACCA TTTATTCTGG CGGATGGGTT GATGTTCATA AAAATATTAC GCTTGATCAG   2040
GGTTTTTTAA ATATTACCGC CGCTTCCGTA GCTTTTGAAG GTGGAAATAA CAAAGCACGC   2100
GACGCGGCAA ATGCTAAAAT TGTCGCCCAG GGCACTGTAA CCATTACAGG AGAGGGAAAA   2160
GATTTCAGGG CTAACAACGT ATCTTTAAAC GGAACGGGTA AAGGTCTGAA TATCATTTCA   2220
TCAGTGAATA ATTTAACCCA CAATCTTAGT GGCACAATTA ACATATCTGG GAATATAACA   2280
ATTAACCAAA CTACGAGAAA GAACACCTCG TATTGGCAAA CCAGCCATGA TTCGCACTGG   2340
AACGTCAGTG CTCTTAATCT AGAGACAGGC GCAAATTTTA CCTTTATTAA ATACATTTCA   2400
AGCAATAGCA AAGGCTTAAC AACACAGTAT AGAAGCTCTG CAGGGGTGAA TTTTAACGGC   2460
GTAAATGGCA ACATGTCATT CAATCTCAAA GAAGGAGCGA AAGTTAATTT CAAATTAAAA   2520
CCAAACGAGA ACATGAACAC AAGCAAACCT TTACCAATTC GGTTTTTAGC CAATATCACA   2580
GCCACTGGTG GGGGCTCTGT TTTTTTTGAT ATATATGCCA ACCATTCTGG CAGAGGGGCT   2640
GAGTTAAAAA TGAGTGAAAT TAATATCTCT AACGGCGCTA ATTTTACCTT AAATTCCCAT   2700
GTTCGCGGCG ATGACGCTTT TAAAATCAAC AAAGACTTAA CCATAAATGC AACCAATTCA   2760
AATTTCAGCC TCAGACAGAC GAAAGATGAT TTTTATGACG GGTACGCACG CAATGCCATC   2820
AATTCAACCT ACAACATATC CATTCTGGGC GGTAATGTCA CCCTTGGTGG ACAAAACTCA   2880
AGCAGCAGCA TTACGGGGAA TATTACTATC GAGAAAGCAG CAAATGTTAC GCTAGAAGCC   2940
AATAACGCCC CTAATCAGCA AAACATAAGG GATAGAGTTA TAAAACTTGG CAGCTTGCTC   3000
GTTAATGGGA GTTTAAGTTT AACTGGCGAA AATGCAGATA TTAAAGGCAA TCTCACTATT   3060
```

-continued

```
TCAGAAAGCG CCACTTTTAA AGGAAAGACT AGAGATACCC TAAATATCAC CGGCAATTTT   3120

ACCAATAATG GCACTGCCGA AATTAATATA ACACAAGGAG TGGTAAAACT TGGCAATGTT   3180

ACCAATGATG GTGATTTAAA CATTACCACT CACGCTAAAC GCAACCAAAG AAGCATCATC   3240

GGCGGAGATA TAATCAACAA AAAAGGAAGC TTAAATATTA CAGACAGTAA TAATGATGCT   3300

GAAATCCAAA TTGGCGGCAA TATCTCGCAA AAAGAAGGCA ACCTCACGAT TTCTTCCGAT   3360

AAAATTAATA TCACCAAACA GATAACAATC AAAAAGGGTA TTGATGGAGA GGACTCTAGT   3420

TCAGATGCGA CAAGTAATGC CAACCTAACT ATTAAAACCA AAGAATTGAA ATTGACAGAA   3480

GACCTAAGTA TTTCAGGTTT CAATAAAGCA GAGATTACAG CCAAAGATGG TAGAGATTTA   3540

ACTATTGGCA ACAGTAATGA CGGTAACAGC GGTGCCGAAG CCAAAACAGT AACTTTTAAC   3600

AATGTTAAAG ATTCAAAAAT CTCTGCTGAC GGTCACAATG TGACACTAAA TAGCAAAGTG   3660

AAAACATCTA GCAGCAATGG CGGACGTGAA AGCAATAGCG ACAACGATAC CGGCTTAACT   3720

ATTACTGCAA AAAATGTAGA AGTAAACAAA GATATTACTT CTCTCAAAAC AGTAAATATC   3780

ACCGCGTCGG AAAAGGTTAC CACCACAGCA GGCTCGACCA TTAACGCAAC AAATGGCAAA   3840

GCAAGTATTA CAACCAAAAC AGGTGATATC AGCGGTACGA TTTCCGGTAA CACGGTAAGT   3900

GTTAGCGCGA CTGGTGATTT AACCACTAAA TCCGGCTCAA AAATTGAAGC GAAATCGGGT   3960

GAGGCTAATG TAACAAGTGC AACAGGTACA ATTGGCGGTA CAATTTCCGG TAATACGGTA   4020

AATGTTACGG CAAACGCTGG CGATTTAACA GTTGGGAATG GCGCAGAAAT TAATGCGACA   4080

GAAGGAGCTG CAACCTTAAC CGCAACAGGG AATACCTTGA CTACTGAAGC CGGTTCTAGC   4140

ATCACTTCAA CTAAGGGTCA GGTAGACCTC TTGGCTCAGA ATGGTAGCAT CGCAGGAAGC   4200

ATTAATGCTG CTAATGTGAC ATTAAATACT ACAGGCACCT TAACCACCGT GGCAGGCTCG   4260

GATATTAAAG CAACCAGCGG CACCTTGGTT ATTAACGCAA AAGATGCTAA GCTAAATGGT   4320

GATGCATCAG GTGATAGTAC AGAAGTGAAT GCAGTCAACG CAAGCGGCTC TGGTAGTGTG   4380

ACTGCGGCAA CCTCAAGCAG TGTGAATATC ACTGGGGATT TAAACACAGT AAATGGGTTA   4440

AATATCATTT CGAAAGATGG TAGAAACACT GTGCGCTTAA GAGGCAAGGA AATTGAGGTG   4500

AAATATATCC AGCCAGGTGT AGCAAGTGTA GAAGAAGTAA TTGAAGCGAA ACGCGTCCTT   4560

GAAAAAGTAA AAGATTTATC TGATGAAGAA AGAGAAACAT TAGCTAAACT TGGTGTAAGT   4620

GCTGTACGTT TTGTTGAGCC AAATAATACA ATTACAGTCA ATACACAAAA TGAATTTACA   4680

ACCAGACCGT CAAGTCAAGT GATAATTTCT GAAGGTAAGG CGTGTTTCTC AAGTGGTAAT   4740

GGCGCACGAG TATGTACCAA TGTTGCTGAC GATGGACAGC CGTAGTCAGT AATTGACAAG   4800

GTAGATTTCA TCCTGCAATG AAGTCATTTT ATTTTCGTAT TATTTACTGT GTGGGTTAAA   4860

GTTCAGTACG GGCTTTACCC ATCTTGTAAA AAATTACGGA GAATACAATA AAGTATTTTT   4920

AACAGGTTAT TATTATG                                                  4937
```

(2) INFORMATION FOR SEQ ID NO:4:

(i) SEQUENCE CHARACTERISTICS:
- (A) LENGTH: 1477 amino acids
- (B) TYPE: amino acid
- (C) STRANDEDNESS: single
- (D) TOPOLOGY: linear (xi) SEQUENCE DESCRIPTION: SEQ ID NO:4:

```
Met Asn Lys Ile Tyr Arg Leu Lys Phe Ser Lys Arg Leu Asn Ala Leu
1               5                   10                  15

Val Ala Val Ser Glu Leu Ala Arg Gly Cys Asp His Ser Thr Glu Lys
```

-continued

```
            20                  25                  30

Gly Ser Glu Lys Pro Ala Arg Met Lys Val Arg His Leu Ala Leu Lys
        35                  40                  45

Pro Leu Ser Ala Met Leu Leu Ser Leu Gly Val Thr Ser Ile Pro Gln
    50                  55                  60

Ser Val Leu Ala Ser Gly Leu Gln Gly Met Asp Val Val His Gly Thr
65                  70                  75                  80

Ala Thr Met Gln Val Asp Gly Asn Lys Thr Ile Ile Arg Asn Ser Val
                85                  90                  95

Asp Ala Ile Ile Asn Trp Lys Gln Phe Asn Ile Asp Gln Asn Glu Met
            100                 105                 110

Val Gln Phe Leu Gln Glu Asn Asn Asn Ser Ala Val Phe Asn Arg Val
        115                 120                 125

Thr Ser Asn Gln Ile Ser Gln Leu Lys Gly Ile Leu Asp Ser Asn Gly
    130                 135                 140

Gln Val Phe Leu Ile Asn Pro Asn Gly Ile Thr Ile Gly Lys Asp Ala
145                 150                 155                 160

Ile Ile Asn Thr Asn Gly Phe Thr Ala Ser Thr Leu Asp Ile Ser Asn
                165                 170                 175

Glu Asn Ile Lys Ala Arg Asn Phe Thr Phe Glu Gln Thr Lys Asp Lys
            180                 185                 190

Ala Leu Ala Glu Ile Val Asn His Gly Leu Ile Thr Val Gly Lys Asp
        195                 200                 205

Gly Ser Val Asn Leu Ile Gly Gly Lys Val Lys Asn Glu Gly Val Ile
    210                 215                 220

Ser Val Asn Gly Gly Ser Ile Ser Leu Leu Ala Gly Gln Lys Ile Thr
225                 230                 235                 240

Ile Ser Asp Ile Ile Asn Pro Thr Ile Thr Tyr Ser Ile Ala Ala Pro
                245                 250                 255

Glu Asn Glu Ala Val Asn Leu Gly Asp Ile Phe Ala Lys Gly Gly Asn
            260                 265                 270

Ile Asn Val Arg Ala Ala Thr Ile Arg Asn Gln Gly Lys Leu Ser Ala
        275                 280                 285

Asp Ser Val Ser Lys Asp Lys Ser Gly Asn Ile Val Leu Ser Ala Lys
    290                 295                 300

Glu Gly Glu Ala Glu Ile Gly Gly Val Ile Ser Ala Gln Asn Gln Gln
305                 310                 315                 320

Ala Lys Gly Gly Lys Leu Met Ile Thr Gly Asp Lys Val Thr Leu Lys
                325                 330                 335

Thr Gly Ala Val Ile Asp Leu Ser Gly Lys Glu Gly Gly Glu Thr Tyr
            340                 345                 350

Leu Gly Gly Asp Glu Arg Gly Glu Gly Lys Asn Gly Ile Gln Leu Ala
        355                 360                 365

Lys Lys Thr Ser Leu Glu Lys Gly Ser Thr Ile Asn Val Ser Gly Lys
    370                 375                 380

Glu Lys Gly Gly Phe Ala Ile Val Trp Gly Asp Ile Ala Leu Ile Asp
385                 390                 395                 400

Gly Asn Ile Asn Ala Gln Gly Ser Gly Asp Ile Ala Lys Thr Gly Gly
                405                 410                 415

Phe Val Glu Thr Ser Gly His Asp Leu Phe Ile Lys Asp Asn Ala Ile
            420                 425                 430

Val Asp Ala Lys Glu Trp Leu Leu Asp Phe Asp Asn Val Ser Ile Asn
        435                 440                 445
```

-continued

```
Ala Glu Asp Pro Leu Phe Asn Asn Thr Gly Ile Asn Asp Glu Phe Pro
    450                 455                 460

Thr Gly Thr Gly Glu Ala Ser Asp Pro Lys Lys Asn Ser Glu Leu Lys
465                 470                 475                 480

Thr Thr Leu Thr Asn Thr Thr Ile Ser Asn Tyr Leu Lys Asn Ala Trp
                485                 490                 495

Thr Met Asn Ile Thr Ala Ser Arg Lys Leu Thr Val Asn Ser Ser Ile
            500                 505                 510

Asn Ile Gly Ser Asn Ser His Leu Ile Leu His Ser Lys Gly Gln Arg
        515                 520                 525

Gly Gly Gly Val Gln Ile Asp Gly Asp Ile Thr Ser Lys Gly Gly Asn
    530                 535                 540

Leu Thr Ile Tyr Ser Gly Gly Trp Val Asp Val His Lys Asn Ile Thr
545                 550                 555                 560

Leu Asp Gln Gly Phe Leu Asn Ile Thr Ala Ala Ser Val Ala Phe Glu
                565                 570                 575

Gly Gly Asn Asn Lys Ala Arg Asp Ala Ala Asn Ala Lys Ile Val Ala
            580                 585                 590

Gln Gly Thr Val Thr Ile Thr Gly Glu Gly Lys Asp Phe Arg Ala Asn
        595                 600                 605

Asn Val Ser Leu Asn Gly Thr Gly Lys Gly Leu Asn Ile Ile Ser Ser
    610                 615                 620

Val Asn Asn Leu Thr His Asn Leu Ser Gly Thr Ile Asn Ile Ser Gly
625                 630                 635                 640

Asn Ile Thr Ile Asn Gln Thr Thr Arg Lys Asn Thr Ser Tyr Trp Gln
                645                 650                 655

Thr Ser His Asp Ser His Trp Asn Val Ser Ala Leu Asn Leu Glu Thr
            660                 665                 670

Gly Ala Asn Phe Thr Phe Ile Lys Tyr Ile Ser Ser Asn Ser Lys Gly
        675                 680                 685

Leu Thr Thr Gln Tyr Arg Ser Ser Ala Gly Val Asn Phe Asn Gly Val
    690                 695                 700

Asn Gly Asn Met Ser Phe Asn Leu Lys Glu Gly Ala Lys Val Asn Phe
705                 710                 715                 720

Lys Leu Lys Pro Asn Glu Asn Met Asn Thr Ser Lys Pro Leu Pro Ile
                725                 730                 735

Arg Phe Leu Ala Asn Ile Thr Ala Thr Gly Gly Gly Ser Val Phe Phe
            740                 745                 750

Asp Ile Tyr Ala Asn His Ser Gly Arg Gly Ala Glu Leu Lys Met Ser
        755                 760                 765

Glu Ile Asn Ile Ser Asn Gly Ala Asn Phe Thr Leu Asn Ser His Val
    770                 775                 780

Arg Gly Asp Asp Ala Phe Lys Ile Asn Lys Asp Leu Thr Ile Asn Ala
785                 790                 795                 800

Thr Asn Ser Asn Phe Ser Leu Arg Gln Thr Lys Asp Asp Phe Tyr Asp
                805                 810                 815

Gly Tyr Ala Arg Asn Ala Ile Asn Ser Thr Tyr Asn Ile Ser Ile Leu
            820                 825                 830

Gly Gly Asn Val Thr Leu Gly Gly Gln Asn Ser Ser Ser Ser Ile Thr
        835                 840                 845

Gly Asn Ile Thr Ile Glu Lys Ala Ala Asn Val Thr Leu Glu Ala Asn
    850                 855                 860
```

-continued

```
Asn Ala Pro Asn Gln Gln Asn Ile Arg Asp Arg Val Ile Lys Leu Gly
865                 870                 875                 880

Ser Leu Leu Val Asn Gly Ser Leu Ser Leu Thr Gly Glu Asn Ala Asp
                885                 890                 895

Ile Lys Gly Asn Leu Thr Ile Ser Glu Ser Ala Thr Phe Lys Gly Lys
            900                 905                 910

Thr Arg Asp Thr Leu Asn Ile Thr Gly Asn Phe Thr Asn Asn Gly Thr
        915                 920                 925

Ala Glu Ile Asn Ile Thr Gln Gly Val Val Lys Leu Gly Asn Val Thr
    930                 935                 940

Asn Asp Gly Asp Leu Asn Ile Thr Thr His Ala Lys Arg Asn Gln Arg
945                 950                 955                 960

Ser Ile Ile Gly Gly Asp Ile Ile Asn Lys Lys Gly Ser Leu Asn Ile
                965                 970                 975

Thr Asp Ser Asn Asn Asp Ala Glu Ile Gln Ile Gly Gly Asn Ile Ser
            980                 985                 990

Gln Lys Glu Gly Asn Leu Thr Ile Ser Ser Asp Lys Ile Asn Ile Thr
        995                 1000                1005

Lys Gln Ile Thr Ile Lys Lys Gly Ile Asp Gly Glu Asp Ser Ser Ser
    1010                1015                1020

Asp Ala Thr Ser Asn Ala Asn Leu Thr Ile Lys Thr Lys Glu Leu Lys
1025                1030                1035                1040

Leu Thr Glu Asp Leu Ser Ile Ser Gly Phe Asn Lys Ala Glu Ile Thr
                1045                1050                1055

Ala Lys Asp Gly Arg Asp Leu Thr Ile Gly Asn Ser Asn Asp Gly Asn
            1060                1065                1070

Ser Gly Ala Glu Ala Lys Thr Val Thr Phe Asn Asn Val Lys Asp Ser
        1075                1080                1085

Lys Ile Ser Ala Asp Gly His Asn Val Thr Leu Asn Ser Lys Val Lys
    1090                1095                1100

Thr Ser Ser Ser Asn Gly Gly Arg Glu Ser Asn Ser Asp Asn Asp Thr
1105                1110                1115                1120

Gly Leu Thr Ile Thr Ala Lys Asn Val Glu Val Asn Lys Asp Ile Thr
                1125                1130                1135

Ser Leu Lys Thr Val Asn Ile Thr Ala Ser Glu Lys Val Thr Thr Thr
            1140                1145                1150

Ala Gly Ser Thr Ile Asn Ala Thr Asn Gly Lys Ala Ser Ile Thr Thr
        1155                1160                1165

Lys Thr Gly Asp Ile Ser Gly Thr Ile Ser Gly Asn Thr Val Ser Val
    1170                1175                1180

Ser Ala Thr Val Asp Leu Thr Thr Lys Ser Gly Ser Lys Ile Glu Ala
1185                1190                1195                1200

Lys Ser Gly Glu Ala Asn Val Thr Ser Ala Thr Gly Thr Ile Gly Gly
                1205                1210                1215

Thr Ile Ser Gly Asn Thr Val Asn Val Thr Ala Asn Ala Gly Asp Leu
            1220                1225                1230

Thr Val Gly Asn Gly Ala Glu Ile Asn Ala Thr Glu Gly Ala Ala Thr
        1235                1240                1245

Leu Thr Ala Thr Gly Asn Thr Leu Thr Thr Glu Ala Gly Ser Ser Ile
    1250                1255                1260

Thr Ser Thr Lys Gly Gln Val Asp Leu Leu Ala Gln Asn Gly Ser Ile
1265                1270                1275                1280

Ala Gly Ser Ile Asn Ala Ala Asn Val Thr Leu Asn Thr Thr Gly Thr
```

-continued

```
            1285                1290                1295

Leu Thr Thr Val Ala Gly Ser Asp Ile Lys Ala Thr Ser Gly Thr Leu
        1300                1305                1310

Val Ile Asn Ala Lys Asp Ala Lys Leu Asn Gly Asp Ala Ser Gly Asp
    1315                1320                1325

Ser Thr Glu Val Asn Ala Val Asn Ala Ser Gly Ser Gly Ser Val Thr
    1330                1335                1340

Ala Ala Thr Ser Ser Ser Val Asn Ile Thr Gly Asp Leu Asn Thr Val
1345                1350                1355                1360

Asn Gly Leu Asn Ile Ile Ser Lys Asp Gly Arg Asn Thr Val Arg Leu
            1365                1370                1375

Arg Gly Lys Glu Ile Glu Val Lys Tyr Ile Gln Pro Gly Val Ala Ser
        1380                1385                1390

Val Glu Glu Val Ile Glu Ala Lys Arg Val Leu Glu Lys Val Lys Asp
    1395                1400                1405

Leu Ser Asp Glu Glu Arg Glu Thr Leu Ala Lys Leu Gly Val Ser Ala
    1410                1415                1420

Val Arg Phe Val Glu Pro Asn Asn Thr Ile Thr Val Asn Thr Gln Asn
1425                1430                1435                1440

Glu Phe Thr Thr Arg Pro Ser Ser Gln Val Ile Ile Ser Glu Gly Lys
            1445                1450                1455

Ala Cys Phe Ser Ser Gly Asn Gly Ala Arg Val Cys Thr Asn Val Ala
        1460                1465                1470

Asp Asp Gly Gln Pro
    1475
```

(2) INFORMATION FOR SEQ ID NO:5:

(i) SEQUENCE CHARACTERISTICS:
(A) LENGTH: 9171 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

```
ACAGCGTTCT CTTAATACTA GTACAAACCC ACAATAAAAT ATGACAAACA ACAATTACAA     60

CACCTTTTTT GCAGTCTATA TGCAAATATT TTAAAAAATA GTATAAATCC GCCATATAAA    120

ATGGTATAAT CTTTCATCTT TCATCTTTCA TCTTTCATCT TTCATCTTTC ATCTTTCATC    180

TTTCATCTTT CATCTTTCAT CTTTCATCTT TCATCTTTCA TCTTTCATCT TTCATCTTTC    240

ACATGAAATG ATGAACCGAG GGAAGGGAGG GAGGGGCAAG AATGAAGAGG GAGCTGAACG    300

AACGCAAATG ATAAAGTAAT TTAATTGTTC AACTAACCTT AGGAGAAAAT ATGAACAAGA    360

TATATCGTCT CAAATTCAGC AAACGCCTGA ATGCTTTGGT TGCTGTGTCT GAATTGGCAC    420

GGGGTTGTGA CCATTCCACA GAAAAAGGCA GCGAAAAACC TGCTCGCATG AAAGTGCGTC    480

ACTTAGCGTT AAAGCCACTT TCCGCTATGT TACTATCTTT AGGTGTAACA TCTATTCCAC    540

AATCTGTTTT AGCAAGCGGC TTACAAGGAA TGGATGTAGT ACACGGCACA GCCACTATGC    600

AAGTAGATGG TAATAAAACC ATTATCCGCA ACAGTGTTGA CGCTATCATT AATTGGAAAC    660

AATTTAACAT CGACCAAAAT GAAATGGTGC AGTTTTTACA AGAAAACAAC AACTCCGCCG    720

TATTCAACCG TGTTACATCT AACCAAATCT CCCAATTAAA AGGGATTTTA GATTCTAACG    780

GACAAGTCTT TTTAATCAAC CCAAATGGTA TCACAATAGG TAAAGACGCA ATTATTAACA    840
```

-continued

```
CTAATGGCTT TACGGCTTCT ACGCTAGACA TTTCTAACGA AAACATCAAG GCGCGTAATT    900
TCACCTTCGA GCAAACCAAA GATAAAGCGC TCGCTGAAAT TGTGAATCAC GGTTTAATTA    960
CTGTCGGTAA AGACGGCAGT GTAAATCTTA TTGGTGGCAA AGTGAAAAAC GAGGGTGTGA   1020
TTAGCGTAAA TGGTGGCAGC ATTTCTTTAC TCGCAGGGCA AAAAATCACC ATCAGCGATA   1080
TAATAAACCC AACCATTACT TACAGCATTG CCGCGCCTGA AAATGAAGCG GTCAATCTGG   1140
GCGATATTTT TGCCAAAGGC GGTAACATTA ATGTCCGTGC TGCCACTATT CGAAACCAAG   1200
CTTTCCGCCA AAGAGGGTGA AGCGGAAATT GGCGGTGTAA TTTCCGCTCA AAATCAGCAA   1260
GCTAAAGGCG GCAAGCTGAT GATTACAGGC GATAAAGTCA CATTAAAAAC AGGTGCAGTT   1320
ATCGACCTTT CAGGTAAAGA AGGGGGAGAA ACTTACCTTG GCGGTGACGA GCGCGGCGAA   1380
GGTAAAAACG GCATTCAATT AGCAAAGAAA ACCTCTTTAG AAAAAGGCTC AACCATCAAT   1440
GTATCAGGCA AAGAAAAAGG CGGACGCGCT ATTGTGTGGG GCGATATTGC GTTAATTGAC   1500
GGCAATATTA ACGCTCAAGG TAGTGGTGAT ATCGCTAAAA CCGGTGGTTT TGTGGAGACG   1560
TCGGGGCATG ATTTATTCAT CAAAGACAAT GCAATTGTTG ACGCCAAAGA GTGGTTGTTA   1620
GACCCGGATA ATGTATCTAT TAATGCAGAA ACAGCAGGAC GCAGCAATAC TTCAGAAGAC   1680
GATGAATACA CGGGATCCGG GAATAGTGCC AGCACCCCAA AACGAAACAA AGAAAAGACA   1740
ACATTAACAA ACACAACTCT TGAGAGTATA CTAAAAAAAG GTACCTTTGT TAACATCACT   1800
GCTAATCAAC GCATCTATGT CAATAGCTCC ATTAATTTAT CCAATGGCAG CTTAACTCTT   1860
TGGAGTGAGG GTCGGAGCGG TGGCGGCGTT GAGATTAACA ACGATATTAC CACCGGTGAT   1920
GATACCAGAG GTGCAAACTT AACAATTTAC TCAGGCGGCT GGGTTGATGT TCATAAAAAT   1980
ATCTCACTCG GGGCGCAAGG TAACATAAAC ATTACAGCTA AACAAGATAT CGCCTTTGAG   2040
AAAGGAAGCA ACCAAGTCAT TACAGGTCAA GGGACTATTA CCTCAGGCAA TCAAAAAGGT   2100
TTTAGATTTA ATAATGTCTC TCTAAACGGC ACTGGCAGCG GACTGCAATT CACCACTAAA   2160
AGAACCAATA AATACGCTAT CACAAATAAA TTTGAAGGGA CTTTAAATAT TTCAGGGAAA   2220
GTGAACATCT CAATGGTTTT ACCTAAAAAT GAAAGTGGAT ATGATAAATT CAAAGGACGC   2280
ACTTACTGGA ATTTAACCTC GAAAGTGGAT ATGATAAATT CAAAGGACGC CCTCACTATT   2340
GACTCCAGAG GAAGCGATAG TGCAGGCACA CTTACCCAGC CTTATAATTT AAACGGTATA   2400
TCATTCAACA AAGACACTAC CTTTAATGTT GAACGAAATG CAAGAGTCAA CTTTGACATC   2460
AAGGCACCAA TAGGGATAAA TAAGTATTCT AGTTTGAATT ACGCATCATT TAATGGAAAC   2520
ATTTCAGTTT CGGGAGGGGG GAGTGTTGAT TTCACACTTC TCGCCTCATC CTCTAACGTC   2580
CAAACCCCCG GTGTAGTTAT AAATTCTAAA TACTTTAATG TTTCAACAGG GTCAAGTTTA   2640
AGATTTAAAA CTTCAGGCTC AACAAAAACT GGCTTCTCAA TAGAGAAAGA TTTAACTTTA   2700
AATGCCACCG GAGGCAACAT AACACTTTTG CAAGTTGAAG GCACCGATGG AATGATTGGT   2760
AAAGGCATTG TAGCCAAAAA AAACATAACC TTTGAAGGAG GTAAGATGAG GTTTGGCTCC   2820
AGGAAAGCCG TAACAGAAAT CGAAGGCAAT GTTACTATCA ATAACAACGC TAACGTCACT   2880
CTTATCGGTT CGGATTTTGA CAACCATCAA AAACCTTTAA CTATTAAAAA AGATGTCATC   2940
ATTAATAGCG GCAACCTTAC CGCTGGAGGC AATATTGTCA ATATAGCCGG AAATCTTACC   3000
GTTGAAAGTA ACGCTAATTT CAAAGCTATC ACAAATTTCA CTTTTAATGT AGGCGGCTTG   3060
TTTGACAACA AAGGCAATTC AAATATTTCC ATTGCCAAAG GAGGGGCTCG CTTTAAAGAC   3120
ATTGATAATT CCAAGAATTT AAGCATCACC ACCAACTCCA GCTCCACTTA CCGCACTATT   3180
ATAAGCGGCA ATATAACCAA TAAAAACGGT GATTTAAATA TTACGAACGA AGGTAGTGAT   3240
```

-continued

ACTGAAATGC AAATTGGCGG CGATGTCTCG CAAAAAGAAG GTAATCTCAC GATTTCTTCT 3300

GACAAAATCA ATATTACCAA ACAGATAACA ATCAAGGCAG GTGTTGATGG GGAGAATTCC 3360

GATTCAGACG CGACAAACAA TGCCAATCTA ACCATTAAAA CCAAAGAATT GAAATTAACG 3420

CAAGACCTAA ATATTTCAGG TTTCAATAAA GCAGAGATTA CAGCTAAAGA TGGTAGTGAT 3480

TTAACTATTG GTAACACCAA TAGTGCTGAT GGTACTAATG CCAAAAAAGT AACCTTTAAC 3540

CAGGTTAAAG ATTCAAAAAT CTCTGCTGAC GGTCACAAGG TGACACTACA CAGCAAAGTG 3600

GAAACATCCG GTAGTAATAA CAACACTGAA GATAGCAGTG ACAATAATGC CGGCTTAACT 3660

ATCGATGCAA AAAATGTAAC AGTAAACAAC AATATTACTT CTCACAAAGC AGTGAGCATC 3720

TCTGCGACAA GTGGAGAAAT TACCACTAAA ACAGGTACAA CCATTAACGC AACCACTGGT 3780

AACGTGGAGA TAACCGCTCA AACAGGTAGT ATCCTAGGTG GAATTGAGTC CAGCTCTGGC 3840

TCTGTAACAC TTACTGCAAC CGAGGGCGCT CTTGCTGTAA GCAATATTTC GGGCAACACC 3900

GTTACTGTTA CTGCAAATAG CGGTGCATTA ACCACTTTGG CAGGCTCTAC AATTAAAGGA 3960

ACCGAGAGTG TAACCACTTC AAGTCAATCA GGCGATATCG GCGGTACGAT TTCTGGTGGC 4020

ACAGTAGAGG TTAAAGCAAC CGAAAGTTTA ACCACTCAAT CCAATTCAAA AATTAAAGCA 4080

ACAACAGGCG AGGCTAACGT AACAAGTGCA ACAGGTACAA TTGGTGGTAC GATTTCCGGT 4140

AATACGGTAA ATGTTACGGC AAACGCTGGC GATTTAACAG TTGGGAATGG CGCAGAAATT 4200

AATGCGACAG AAGGAGCTGC AACCTTAACT ACATCATCGG GCAAATTAAC TACCGAAGCT 4260

AGTTCACACA TTACTTCAGC CAAGGGTCAG GTAAATCTTT CAGCTCAGGA TGGTAGCGTT 4320

GCAGGAAGTA TTAATGCCGC CAATGTGACA CTAAATACTA CAGGCACTTT AACTACCGTG 4380

AAGGGTTCAA ACATTAATGC AACCAGCGGT ACCTTGGTTA TTAACGCAAA AGACGCTGAG 4440

CTAAATGGCG CAGCATTGGG TAACCACACA GTGGTAAATG CAACCAACGC AAATGGCTCC 4500

GGCAGCGTAA TCGCGACAAC CTCAAGCAGA GTGAACATCA CTGGGGATTT AATCACAATA 4560

AATGGATTAA ATATCATTTC AAAAAACGGT ATAAACACCG TACTGTTAAA AGGCGTTAAA 4620

ATTGATGTGA AATACATTCA ACCGGGTATA GCAAGCGTAG ATGAAGTAAT TGAAGCGAAA 4680

CGCATCCTTG AGAAGGTAAA AGATTTATCT GATGAAGAAA GAGAAGCGTT AGCTAAACTT 4740

GGCGTAAGTG CTGTACGTTT TATTGAGCCA AATAATACAA TTACAGTCGA TACACAAAAT 4800

GAATTTGCAA CCAGACCATT AAGTCGAATA GTGATTTCTG AAGGCAGGGC GTGTTTCTCA 4860

AACAGTGATG GCGCGACGGT GTGCGTTAAT ATCGCTGATA ACGGGCGGTA GCGGTCAGTA 4920

ATTGACAAGG TAGATTTCAT CCTGCAATGA AGTCATTTTA TTTTCGTATT ATTTACTGTG 4980

TGGGTTAAAG TTCAGTACGG GCTTTACCCA TCTTGTAAAA AATTACGGAG AATACAATAA 5040

AGTATTTTTA ACAGGTTATT ATTATGAAAA ATATAAAAAG CAGATTAAAA CTCAGTGCAA 5100

TATCAGTATT GCTTGGCCTG GCTTCTTCAT CATTGTATGC AGAAGAAGCG TTTTTAGTAA 5160

AAGGCTTTCA GTTATCTGGT GCACTTGAAA CTTTAAGTGA AGACGCCCAA CTGTCTGTAG 5220

CAAAATCTTT ATCTAAATAC CAAGGCTCGC AAACTTTAAC AAACCTAAAA ACAGCACAGC 5280

TTGAATTACA GGCTGTGCTA GATAAGATTG AGCCAAATAA GTTTGATGTG ATATTGCCAC 5340

AACAAACCAT TACGGATGGC AATATTATGT TTGAGCTAGT CTCGAAATCA GCCGCAGAAA 5400

GCCAAGTTTT TTATAAGGCG AGCCAGGGTT ATAGTGAAGA AAATATCGCT CGTAGCCTGC 5460

CATCTTTGAA ACAAGGAAAA GTGTATGAAG ATGGTCGTCA GTGGTTCGAT TTGCGTGAAT 5520

TCAATATGGC AAAAGAAAAT CCACTTAAAG TCACTCGCGT GCATTACGAG TTAAACCCTA 5580

-continued

```
AAAACAAAAC CTCTGATTTG GTAGTTGCAG GTTTTTCGCC TTTTGGCAAA ACGCGTAGCT   5640
TTGTTTCCTA TGATAATTTC GGCGCAAGGG AGTTTAACTA TCAACGTGTA AGTCTAGGTT   5700
TTGTAAATGC CAATTTGACC GGACATGATG ATGTATTAAA TCTAAACGCA TTGACCAATG   5760
TAAAAGCACC ATCAAAATCT TATGCGGTAG GCATAGGATA TACTTATCCG TTTTATGATA   5820
AACACCAATC CTTAAGTCTT TATACCAGCA TGAGTTATGC TGATTCTAAT GATATCGACG   5880
GCTTACCAAG TGCGATTAAT CGTAAATTAT CAAAAGGTCA ATCTATCTCT GCGAATCTGA   5940
AATGGAGTTA TTATCTCCCG ACATTTAACC TTGGAATGGA AGACCAGTTT AAAATTAATT   6000
TAGGCTACAA CTACCGCCAT ATTAATCAAA CATCCGAGTT AAACACCCTG GGTGCAACGA   6060
AGAAAAAATT TGCAGTATCA GGCGTAAGTG CAGGCATTGA TGGACATATC CAATTTACCC   6120
CTAAAACAAT CTTTAATATT GATTTAACTC ATCATTATTA CGCGAGTAAA TTACCAGGCT   6180
CTTTTGGAAT GGAGCGCATT GGCGAAACAT TTAATCGCAG CTATCACATT AGCACAGCCA   6240
GTTTAGGGTT GAGTCAAGAG TTTGCTCAAG GTTGGCATTT TAGCAGTCAA TTATCGGGTC   6300
AGTTTACTCT ACAAGATATA AGTAGCATAG ATTTATTCTC TGTAACAGGT ACTTATGGCG   6360
TCAGAGGCTT TAAATACGGC GGTGCAAGTG GTGAGCGCGG TCTTGTATGG CGTAATGAAT   6420
TAAGTATGCC AAAATACACC CGCTTTCAAA TCAGCCCTTA TGCGTTTTAT GATGCAGGTC   6480
AGTTCCGTTA TAATAGCGAA AATGCTAAAA CTTACGGCGA AGATATGCAC ACGGTATCCT   6540
CTGCGGGTTT AGGCATTAAA ACCTCTCCTA CACAAAACTT AAGCTTAGAT GCTTTTGTTG   6600
CTCGTCGCTT TGCAAATGCC AATAGTGACA ATTTGAATGG CAACAAAAAA CGCACAAGCT   6660
CACCTACAAC CTTCTGGGGT AGATTAACAT TCAGTTTCTA ACCCTGAAAT TTAATCAACT   6720
GGTAAGCGTT CCGCCTACCA GTTTATAACT ATATGCTTTA CCCGCCAATT TACAGTCTAT   6780
ACGCAACCCT GTTTTCATCC TTATATATCA AACAAACTAA GCAAACCAAG CAAACCAAGC   6840
AAACCAAGCA AACCAAGCAA ACCAAGCAAA CCAAGCAAAC CAAGCAAACC AAGCAAACCA   6900
AGCAAACCAA GCAAACCAAG CAAACCAAGC AAACCAAGCA ATGCTAAAAA ACAATTTATA   6960
TGATAAACTA AAACATACTC CATACCATGG CAATACAAGG GATTTAATAA TATGACAAAA   7020
GAAAATTTAC AAAGTGTTCC ACAAAATACG ACCGCTTCAC TTGTAGAATC AAACAACGAC   7080
CAAACTTCCC TGCAAATACT TAAACAACCA CCCAAACCCA ACCTATTACG CCTGGAACAA   7140
CATGTCGCCA AAAAAGATTA TGAGCTTGCT TGCCGCGAAT TAATGGCGAT TTTGGAAAAA   7200
ATGGACGCTA ATTTTGGAGG CGTTCACGAT ATTGAATTTG ACGCACCTGC TCAGCTGGCA   7260
TATCTACCCG AAAAACTACT AATTCATTTT GCCACTCGTC TCGCTAATGC AATTACAACA   7320
CTCTTTTCCG ACCCCGAATT GGCAATTTCC GAAGAAGGGG CATTAAAGAT GATTAGCCTG   7380
CAACGCTGGT TGACGCTGAT TTTTGCCTCT TCCCCCTACG TTAACGCAGA CCATATTCTC   7440
AATAAATATA ATATCAACCC AGATTCCGAA GGTGGCTTTC ATTTAGCAAC AGACAACTCT   7500
TCTATTGCTA AATTCTGTAT TTTTTACTTA CCCGAATCCA ATGTCAATAT GAGTTTAGAT   7560
GCGTTATGGG CAGGGAATCA ACAACTTTGT GCTTCATTGT GTTTTGCGTT GCAGTCTTCA   7620
CGTTTTATTG GTACTGCATC TGCGTTTCAT AAAAGAGCGG TGGTTTTACA GTGGTTTCCT   7680
AAAAAACTCG CCGAAATTGC TAATTTAGAT GAATTGCCTG CAAATATCCT TCATGATGTA   7740
TATATGCACT GCAGTTATGA TTTAGCAAAA AACAAGCACG ATGTTAAGCG TCCATTAAAC   7800
GAACTTGTCC GCAAGCATAT CCTCACGCAA GGATGGCAAG ACCGCTACCT TTACACCTTA   7860
GGTAAAAAGG ACGGCAAACC TGTGATGATG GTACTGCTTG AACATTTTAA TTCGGGACAT   7920
TCGATTTATC GCACGCATTC AACTTCAATG ATTGCTGCTC GAGAAAAATT CTATTTAGTC   7980
```

```
GGCTTAGGCC ATGAGGGCGT TGATAACATA GGTCGAGAAG TGTTTGACGA GTTCTTTGAA   8040

ATCAGTAGCA ATAATATAAT GGAGAGACTG TTTTTTATCC GTAAACAGTG CGAAACTTTC   8100

CAACCCGCAG TGTTCTATAT GCCAAGCATT GGCATGGATA TTACCACGAT TTTTGTGAGC   8160

AACACTCGGC TTGCCCCTAT TCAAGCTGTA GCCTTGGGTC ATCCTGCCAC TACGCATTCT   8220

GAATTTATTG ATTATGTCAT CGTAGAAGAT GATTATGTGG GCAGTGAAGA TTGTTTTAGC   8280

GAAACCCTTT TACGCTTACC CAAAGATGCC CTACCTTATG TACCATCTGC ACTCGCCCCA   8340

CAAAAAGTGG ATTATGTACT CAGGGAAAAC CCTGAAGTAG TCAATATCGG TATTGCCGCT   8400

ACCACAATGA AATTAAACCC TGAATTTTTG CTAACATTGC AAGAAATCAG AGATAAAGCT   8460

AAAGTCAAAA TACATTTTCA TTTCGCACTT GGACAATCAA CAGGCTTGAC ACACCCTTAT   8520

GTCAAATGGT TTATCGAAAG CTATTTAGGT GACGATGCCA CTGCACATCC CCACGCACCT   8580

TATCACGATT ATCTGGCAAT ATTGCGTGAT TGCGATATGC TACTAAATCC GTTTCCTTTC   8640

GGTAATACTA ACGGCATAAT TGATATGGTT ACATTAGGTT TAGTTGGTGT ATGCAAAACG   8700

GGGGATGAAG TACATGAACA TATTGATGAA GGTCTGTTTA AACGCTTAGG ACTACCAGAA   8760

TGGCTGATAG CCGACACACG AGAAACATAT ATTGAATGTG CTTTGCGTCT AGCAGAAAAC   8820

CATCAAGAAC GCCTTGAACT CCGTCGTTAC ATCATAGAAA ACAACGGCTT ACAAAAGCTT   8880

TTTACAGGCG ACCCTCGTCC ATTGGGCAAA ATACTGCTTA AGAAAACAAA TGAATGGAAG   8940

CGGAAGCACT TGAGTAAAAA ATAACGGTTT TTTAAAGTAA AAGTGCGGTT AATTTTCAAA   9000

GCGTTTTAAA AACCTCTCAA AAATCAACCG CACTTTTATC TTTATAACGC TCCCGCGCGC   9060

TGACAGTTTA TCTCTTTCTT AAAATACCCA TAAAATTGTG GCAATAGTTG GGTAATCAAA   9120

TTCAATTGTT GATACGGCAA ACTAAAGACG GCGCGTTCTT CGGCAGTCAT C            9171
```

(2) INFORMATION FOR SEQ ID NO:6:

(i) SEQUENCE CHARACTERISTICS:
(A) LENGTH: 9323 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
CGCCACTTCA ATTTTGGATT GTTGAAATTC AACTAACCAA AAAGTGCGGT TAAAATCTGT     60

GGAGAAAATA GGTTGTAGTG AAGAACGAGG TAATTGTTCA AAAGGATAAA GCTCTCTTAA    120

TTGGGCATTG GTTGGCGTTT CTTTTTCGGT TAATAGTAAA TTATATTCTG GACGACTATG    180

CAATCCACCA ACAACTTTAC CGTTGGTTTT AAGCGTTAAT GTAAGTTCTT GCTCTTCTTG    240

GCGAATACGT AATCCCATTT TTTGTTTAGC AAGAAAATGA TCGGGATAAT CATAATAGGT    300

GTTGCCCAAA AATAAATTTT GATGTTCTAA AATCATAAAT TTTGCAAGAT ATTGTGGCAA    360

TTCAATACCT ATTTGTGGCG AAATCGCCAA TTTTAATTCA ATTTCTTGTA GCATAATATT    420

TCCCACTCAA ATCAACTGGT TAAATATACA AGATAATAAA AATAAATCAA GATTTTTGTG    480

ATGACAAACA ACAATTACAA CACCTTTTTT GCAGTCTATA TGCAAATATT TTAAAAAAAT    540

AGTATAAATC CGCCATATAA AATGGTATAA TCTTTCATCT TTCATCTTTC ATCTTTCATC    600

TTTCATCTTT CATCTTTCAT CTTTCATCTT TCATCTTTCA TCTTTCATCT TTCATCTTTC    660

ATCTTTCATC TTTCATCTTT CACATGAAAT GATGAACCGA GGGAAGGGAG GGAGGGGCAA    720

GAATGAAGAG GGAGCTGAAC GAACGCAAAT GATAAAGTAA TTTAATTGTT CAACTAACCT    780
```

-continued

```
TAGGAGAAAA TATGAACAAG ATATATCGTC TCAAATTCAG CAAACGCCTG AATGCTTTGG    840
TTGCTGTGTC TGAATTGGCA CGGGGTTGTG ACCATTCCAC AGAAAAAGGC AGCGAAAAAC    900
CTGCTCGCAT GAAAGTGCGT CACTTAGCGT TAAAGCCACT TTCCGCTATG TTACTATCTT    960
TAGGTGTAAC ATCTATTCCA CAATCTGTTT TAGCAAGCGG CAATTTAACA TCGACCAAAA   1020
TGAAATGGTG CAGTTTTTAC AAGAAAACAA GTAATAAAAC CATTATCCGC AACAGTGTTG   1080
ACGCTATCAT TAATTGGAAA CAATTTAACA TCGACCAAAA TGAAATGGTG CAGTTTTTAC   1140
AAGAAAACAA CAACTCCGCC GTATTCAACC GTGTTACATC TAACCAAATC TCCCAATTAA   1200
AAGGGATTTT AGATTCTAAC GGACAAGTCT TTTTAATCAA CCCAAATGGT ATCACAATAG   1260
GTAAAGACGC AATTATTAAC ACTAATGGCT TTACGGCTTC TACGCTAGAC ATTTCTAACG   1320
AAAACATCAA GGCGCGTAAT TTCACCTTCG AGCAAACCAA AGATAAAGCG CTCGCTGAAA   1380
TTGTGAATCA CGGTTTAATT ACTGTCGGTA AAGACGGCAG TGTAAATCTT ATTGGTGGCA   1440
AAGTGAAAAA CGAGGGTGTG ATTAGCGTAA ATGGTGGCAG CATTTCTTTA CTCGCAGGGC   1500
AAAAAATCAC CATCAGCGAT ATAATAAACC CAACCATTAC TTACAGCATT GCCGCGCCTG   1560
AAAATGAAGC GGTCAATCTG GGCGATATTT TTGCCAAAGG CGGTAACATT AATGTCCGTG   1620
CTGCCACTAT TCGAAACCAA GGTAAACTTT CTGCTGATTC TGTAAGCAAA GATAAAAGCG   1680
GCAATATTGT TCTTTCCGCC AAAGAGGGTG AAGCGGAAAT TGGCGGTGTA ATTTCCGCTC   1740
AAAATCAGCA AGCTAAAGGC GGCAAGCTGA TGATAAAGTC CGATAAAGTC ACATTAAAAA   1800
CAGGTGCAGT TATCGACCTT TCAGGTAAAG AAGGGGGAGA AACTTACCTT GGCGGTGACG   1860
AGCGCGGCGA AGGTAAAAAC GGCATTCAAT TAGCAAAGAA AACCTCTTTA GAAAAAGGCT   1920
CAACCATCAA TGTATCAGGC AAAGAAAAAG GCGGACGCGC TATTGTGTGG GGCGATATTG   1980
CGTTAATTGA CGGCAATATT AACGCTCAAG GTAGTGGTGA TATCGCTAAA ACCGGTGGTT   2040
TTGTGGAGAC ATCGGGGCAT TATTTATCCA TTGACAGCAA TGCAATTGTT AAAACAAAAG   2100
AGTGGTTGCT AGACCCTGAT GATGTAACAA TTGAAGCCGA AGACCCCCTT CGCAATAATA   2160
CCGGTATAAA TGATGAATTC CCAACAGGCA CCGGTGAAGC AAGCGACCCT AAAAAAAATA   2220
GCGAACTCAA AACAACGCTA ACCAATACAA CTATTTCAAA TTATCTGAAA AACGCCTGGA   2280
CAATGAATAT AACGGCATCA AGAAAACTTA CCGTTAATAG CTCAATCAAC ATCGGAAGCA   2340
ACTCCCACTT AATTCTCCAT AGTAAAGGTC AGCGTGGCGG AGGCGTTCAG ATTGATGGAG   2400
ATATTACTTC TAAAGGCGGA AATTTAACCA TTTATTCTGG CGGATGGGTT GATGTTCATA   2460
AAAATATTAC GCTTGATCAG GGTTTTTTAA ATATTACCGC CGCTTCCGTA GCTTTTGAAG   2520
GTGGAAATAA CAAAGCACGC GACGCGGCAA ATGCTAAAAT TGTCGCCCAG GGCACTGTAA   2580
CCATTACAGG AGAGGGAAAA GATTTCAGGG CTAACAACGT ATCTTTAAAC GGAACGGGTA   2640
AAGGTCTGAA TATCATTTCA TCAGTGAATA ATTTAACCCA CAATCTTAGT GGCACAATTA   2700
ACATATCTGG GAATATAACA ATTAACCAAA CTACGAGAAA GAACACCTCG TATTGGCAAA   2760
CCAGCCATGA TTCGCACTGG AACGTCAGTG CTCTTAATCT AGAGACAGGC GCAAATTTTA   2820
CCTTTATTAA ATACATTTCA AGCAATAGCA AAGGCTTAAC AACACAGTAT AGAAGCTCTG   2880
CAGGGGTGAA TTTTAACGGC GTAAATGGCA ACATGTCATT CAATCTCAAA GAAGGAGCGA   2940
AAGTTAATTT CAAATTAAAA CCAAACGAGA ACATGAACAC AAGCAAACCT TTACCAATTC   3000
GGTTTTTAGC CAATATCACA GCCACTGGTG GGGGCTCTGT TTTTTTTGAT ATATATGCCA   3060
ACCATTCTGG CAGAGGGGCT GAGTTAAAAA TGAGTGAAAT TAATATCTCT AACGGCGCTA   3120
```

-continued

```
ATTTTACCTT AAATTCCCAT GTTCGCGGCG ATGACGCTTT TAAAATCAAC AAAGACTTAA   3180
CCATAAATGC AACCAATTCA AATTTCAGCC TCAGACAGAC GAAAGATGAT TTTTATGACG   3240
GGTACGCACG CAATGCCATC AATTCAACCT ACAACATATC CATTCTGGGC GGTAATGTCA   3300
CCCTTGGTGG ACAAAACTCA AGCAGCAGCA TTACGGGGAA TATTACTATC GAGAAAGCAG   3360
CAAATGTTAC GCTAGAAGCC AATAACGCCC CTAATCAGCA AAACATAAGG GATAGAGTTA   3420
TAAAACTTGG CAGCTTGCTC GTTAATGGGA GTTTAAGTTT AACTGGCGAA AATGCAGATA   3480
TTAAAGGCAA TCTCACTATT TCAGAAAGCG CCACTTTTAA AGGAAAGACT AGAGATACCC   3540
TAAATATCAC CGGCAATTTT ACCAATAATG GCACTGCCGA AATTAATATA ACACAAGGAG   3600
TGGTAAAACT TGGCAATGTT ACCAATGATG GTGATTTAAA CATTACCACT CACGCTAAAC   3660
GCAACCAAAG AAGCATCATC GGCGGAGATA TAATCAACAA AAAAGGAAGC TTAAATATTA   3720
CAGACAGTAA TAATGATGCT GAAATCCAAA TTGGCGGCAA TATCTCGCAA AAAGAAGGCA   3780
ACCTCACGAT TTCTTCCGAT AAAATTAATA TCACCAAACA GATAACAATC AAAAAGGGTA   3840
TTGATGGAGA GGACTCTAGT TCAGATGCGA CAAGTAATGC CAACCTAACT ATTAAAACCA   3900
AAGAATTGAA ATTGACAGAA GACCTAAGTA TTTCAGGTTT CAATAAAGCA GAGATTACAG   3960
CCAAAGATGG TAGAGATTTA ACTATTGGCA ACAGTAATGA CGGTAACAGC GGTGCCGAAG   4020
CCAAAACAGT AACTTTTAAC AATGTTAAAG ATTCAAAAAT CTCTGCTGAC GGTCACAATG   4080
TGACACTAAA TAGCAAAGTG AAAACATCTA GCAGCAATGG CGGACGTGAA AGCAATAGCG   4140
ACAACGATAC CGGCTTAACT ATTACTGCAA AAAATGTAGA AGTAAACAAA GATATTACTT   4200
CTCTCAAAAC AGTAAATATC ACCGCGTCGG AAAAGGTTAC CACCACAGCA GGCTCGACCA   4260
TTAACGCAAC AAATGGCAAA GCAAGTATTA CAACCAAAAC AGGTGATATC AGCGGTACGA   4320
TTTCCGGTAA CACGGTAAGT GTTAGCGCGA CTGGTGATTT AACCACTAAA TCCGGCTCAA   4380
AAATTGAAGC GAAATCGGGT GAGGCTAATG TAACAAGTGC AACAGGTACA ATTGGCGGTA   4440
CAATTTCCGG TAATACGGTA AATGTTACGG CAAACGCTGG CGATTTAACA GTTGGGAATG   4500
GCGCAGAAAT TAATGCGACA GAAGGAGCTG CAACCTTAAC CGCAACAGGG AATACCTTGA   4560
CTACTGAAGC CGGTTCTAGC ATCACTTCAA CTAAGGGTCA GGTAGACCTC TTGGCTCAGA   4620
ATGGTAGCAT CGCAGGAAGC ATTAATGCTG CTAATGTGAC ATTAAATACT ACAGGCACCT   4680
TAACCACCGT GGCAGGCTCG GATATTAAAG CAACCAGCGG CACCTTGGTT ATTAACGCAA   4740
AAGATGCTAA GCTAAATGGT GATGCATCAG GTGATAGTAC AGAAGTGAAT GCAGTCAACG   4800
ACTGGGGATT TGGTAGTGTG ACTGCGGCAA CCTCAAGCAG TGTGAATATC ACTGGGGATT   4860
TAAACACAGT AAATGGGTTA AATATCATTT CGAAAGATGG TAGAAACACT GTGCGCTTAA   4920
GAGGCAAGGA AATTGAGGTG AAATATATCC AGCCAGGTGT AGCAAGTGTA GAAGAAGTAA   4980
TTGAAGCGAA ACGCGTCCTT GAAAAAGTAA AAGATTTATC TGATGAAGAA AGAGAAACAT   5040
TAGCTAAACT TGGTGTAAGT GCTGTACGTT TTGTTGAGCC AAATAATACA ATTACAGTCA   5100
ATACACAAAA TGAATTTACA ACCAGACCGT CAAGTCAAGT GATAATTTCT GAAGGTAAGG   5160
CGTGTTTCTC AAGTGGTAAT GGCGCACGAG TATGTACCAA TGTTGCTGAC GATGGACAGC   5220
CGTAGTCAGT AATTGACAAG GTAGATTTCA TCCTGCAATG AAGTCATTTT ATTTTCGTAT   5280
TATTTACTGT GTGGGTTAAA GTTCAGTACG GGCTTTACCC ATCTTGTAAA AAATTACGGA   5340
GAATACAATA AAGTATTTTT AACAGGTTAT TATTATGAAA AATATAAAAA GCAGATTAAA   5400
ACTCAGTGCA ATATCAGTAT TGCTTGGCCT GGCTTCTTCA TCATTGTATG CAGAAGAAGC   5460
GTTTTTAGTA AAAGGCTTTC AGTTATCTGG TGCACTTGAA ACTTTAAGTG AAGACGCCCA   5520
```

-continued

```
ACTGTCTGTA GCAAAATCTT TATCTAAATA CCAAGGCTCG CAAACTTTAA CAAACCTAAA   5580
AACAGCACAG CTTGAATTAC AGGCTGTGCT AGATAAGATT GAGCCAAATA AATTTGATGT   5640
GATATTGCCG CAACAAACCA TTACGGATGG CAATATCATG TTTGAGCTAG TCTCGAAATC   5700
AGCCGCAGAA AGCCAAGTTT TTTATAAGGC GAGCCAGGGT TATAGTGAAG AAAATATCGC   5760
TCGTAGCCTG CCATCTTTGA AACAAGGAAA AGTGTATGAA GATGGTCGTC AGTGGTTCGA   5820
TTTGCGTGAA TTTAATATGG CAAAAGAAAA CCCGCTTAAG GTTACCCGTG TACATTACGA   5880
ACTAAACCCT AAAAACAAAA CCTCTAATTT GATAATTGCG GGCTTCTCGC CTTTTGGTAA   5940
AACGCGTAGC TTTATTTCTT ATGATAATTT CGGCGCGAGA GAGTTTAACT ACCAACGTGT   6000
AAGCTTGGGT TTTGTTAATG CCAATTTAAC TGGTCATGAT GATGTGTTAA TTATACCAGT   6060
ATGAGTTATG CTGATTCTAA TGATATCGAC GGCTTACCAA GTGCGATTAA TCGTAAATTA   6120
TCAAAAGGTC AATCTATCTC TGCGAATCTG AAATGGAGTT ATTATCTCCC AACATTTAAC   6180
CTTGGCATGG AAGACCAATT TAAAATTAAT TTAGGCTACA ACTACCGCCA TATTAATCAA   6240
ACCTCCGCGT TAAATCGCTT GGGTGAAACG AAGAAAAAAT TTGCAGTATC AGGCGTAAGT   6300
GCAGGCATTG ATGGACATAT CCAATTTACC CCTAAAACAA TCTTTAATAT TGATTTAACT   6360
CATCATTATT ACGCGAGTAA ATTACCAGGC TCTTTTGGAA TGGAGCGCAT TGGCGAAACA   6420
TTTAATCGCA GCTATCACAT TAGCACAGCC AGTTTAGGGT TGAGTCAAGA GTTTGCTCAA   6480
GGTTGGCATT TTAGCAGTCA ATTATCAGGT CAATTTACTC TACAAGATAT TAGCAGTATA   6540
GATTTATTCT CTGTAACAGG TACTTATGGC GTCAGAGGCT TTAAATACGG CGGTGCAAGT   6600
GGTGAGCGCG GTCTTGTATG GCGTAATGAA TTAAGTATGC CAAAATACAC CCGCTTCCAA   6660
ATCAGCCCTT ATGCGTTTTA TGATGCAGGT CAGTTCCGTT ATAATAGCGA AAATGCTAAA   6720
ACTTACGGCG AAGATATGCA CACGGTATCC TCTGCGGGTT TAGGCATTAA AACCTCTCCT   6780
ACACAAAACT TAAGCCTAGA TGCTTTTGTT GCTCGTCGCT TTGCAAATGC CAATAGTGAC   6840
AATTTGAATG GCAACAAAAA ACGCACAAGC TCACCTACAA CCTTCTGGGG GAGATTAACA   6900
TTCAGTTTCT AACCCTGAAA TTTAATCAAC TGGTAAGCGT TCCGCCTACC AGTTTATAAC   6960
TATATGCTTT ACCCGCCAAT TTACAGTCTA TAGGCAACCC TGTTTTTACC CTTATATATC   7020
AAATAAACAA GCTAAGCTGA GCTAAGCAAA CCAAGCAAAC TCAAGCAAGC CAAGTAATAC   7080
TAAAAAAACA ATTTATATGA TAAACTAAAG TATACTCCAT GCCATGGCGA TACAAGGGAT   7140
TTAATAATAT GACAAAAGAA AATTTGCAAA ACGCTCCTCA AGATGCGACC GCTTTACTTG   7200
CGGAATTAAG CAACAATCAA ACTCCCCTGC GAATATTTAA ACAACCACGC AAGCCCAGCC   7260
TATTACGCTT GGAACAACAT ATCGCAAAAA AAGATTATGA GTTTGCTTGT CGTGAATTAA   7320
TGGTGATTCT GGAAAAAATG GACGCTAATT TTGGAGGCGT TCACGATATT GAATTTGACG   7380
CACCCGCTCA GCTGGCATAT CTACCCGAAA AATTACTAAT TTATTTTGCC ACTCGTCTCG   7440
CTAATGCAAT TACAACACTC TTTTCCGACC CCGAATTGGC AATTTCTGAA GAAGGGGCGT   7500
TAAAGATGAT TAGCCTGCAA CGCTGGTTGA CGCTGATTTT TGCCTCTTCC CCCTACGTTA   7560
ACGCAGACCA TATTCTCAAT AAATATAATA TCAACCCAGA TTCCGAAGGT GGCTTTCATT   7620
TAGCAACAGA CAACTCTTCT ATTGCTAAAT TCTGTATTTT TTACTTACCC GAATCCAATG   7680
TCAATATGAG TTTAGATGCG TTATGGGCAG GGAATCAACA ACTTTGTGCT TCATTGTGTT   7740
TTGCGTTGCA GTCTTCACGT TTTATTGGTA CCGCATCTGC GTTTCATAAA AGAGCGGTGG   7800
TTTTACAGTG GTTTCCTAAA AACTCGCCG AAATTGCTAA TTTAGATGAA TTGCCTGCAA   7860
```

-continued

```
ATATCCTTCA TGATGTATAT ATGCACTGCA GTTATGATTT AGCAAAAAAC AAGCACGATG   7920

TTAAGCGTCC ATTAAACGAA CTTGTCCGCA AGCATATCCT CACGCAAGGA TGGCAAGACC   7980

GCTACCTTTA CACCTTAGGT AAAAAGGACG GCAAACCTGT GATGATGGTA CTGCTTGAAC   8040

ATTTTAATTC GGGACATTCG ATTTATCGTA CACATTCAAC TTCAATGATT GCTGCTCGAG   8100

AAAAATTCTA TTTAGTCGGC TTAGGCCATG AGGGCGTTGA TAAAATAGGT CGAGAAGTGT   8160

TTGACGAGTT CTTTGAAATC AGTAGCAATA ATATAATGGA GAGACTGTTT TTTATCCGTA   8220

AACAGTGCGA AACTTTCCAA CCCGCAGTGT TCTATATGCC AAGCATTGGC ATGGATATTA   8280

CCACGATTTT TGTGAGCAAC ACTCGGCTTG CCCCTATTCA AGCTGTAGCC CTGGGTCATC   8340

CTGCCACTAC GCATTCTGAA TTTATTGATT ATGTCATCGT AGAAGATGAT TATGTGGGCA   8400

GTGAAGATTG TTTCAGCGAA ACCCTTTTAC GCTTACCCAA AGATGCCCTA CCTTATGTAC   8460

CTTCTGCACT CGCCCCACAA AAAGTGGATT ATGTACTCAG GGAAAACCCT GAAGTAGTCA   8520

ATATCGGTAT TGCCGCTACC ACAATGAAAT TAAACCCTGA ATTTTTGCTA ACATTGCAAG   8580

AAATCAGAGA TAAAGCTAAA GTCAAAATAC ATTTTCATTT CGCACTTGGA CAATCAACAG   8640

GCTTGACACA CCCTTATGTC AAATGGTTTA TCGAAAGCTA TTTAGGTGAC GATGCCACTG   8700

CACATCCCCA CGCACCTTAT CACGATTATC TGGCAATATT GCGTGATTGC GATATGCTAC   8760

TAAATCCGTT TCCTTTCGGT AATACTAACG GCATAATTGA TATGGTTACA TTAGGTTTAG   8820

TTGGTGTATG CAAAACGGGG GATGAAGTAC ATGAACATAT TGATGAAGGT CTGTTTAAAC   8880

GCTTAGGACT ACCAGAATGG CTGATAGCCG ACACACGAGA AACATATATT GAATGTGCTT   8940

TGCGTCTAGC AGAAAACCAT CAAGAACGCC TTGAACTCCG TCGTTACATC ATAGAAAACA   9000

ACGGCTTACA AAAGCTTTTT ACAGGCGACC CTCGTCCATT GGGCAAAATA CTGCTTAAGA   9060

AAACAAATGA ATGGAAGCGG AAGCACTTGA GTAAAAAATA ACGGTTTTTT AAAGTAAAAG   9120

TGCGGTTAAT TTTCAAAGCG TTTTAAAAAC CTCTCAAAAA TCAACCGCAC TTTTATCTTT   9180

ATAACGATCC CGCACGCTGA CAGTTTATCA GCCTCCCGCC ATAAAACTCC GCCTTTCATG   9240

GCGGAGATTT TAGCCAAAAC TGGCAGAAAT TAAAGGCTAA AATCACCAAA TTGCACCACA   9300

AAATCACCAA TACCCACAAA AAA                                           9323
```

(2) INFORMATION FOR SEQ ID NO:7:

(i) SEQUENCE CHARACTERISTICS:
- (A) LENGTH: 4287 base pairs
- (B) TYPE: nucleic acid
- (C) STRANDEDNESS: single
- (D) TOPOLOGY: linear (ii) MOLECULE TYPE: DNA (genomic)

(xi) SEQUENCE DESCRIPTION: SEQ ID NO:7:

```
GATCAATCTG GGCGATATTT TTGCCAAAGG TGGTAACATT AATGTCCGCG CTGCCACTAT     60

TCGCAATAAA GGTAAACTTT CTGCCGACTC TGTAAGCAAA GATAAAAGTG GTAACATTGT    120

TCTCTCTGCC AAAGAAGGTG AAGCGGAAAT TGGCGGTGTA ATTTCCGCTC AAAATCAGCA    180

AGCCAAAGGT GGTAAGTTGA TGATTACAGG CGATAAAGTT ACATTGAAAA CGGGTGCACT    240

TATCGACCTT TCGGGTAAAG AAGGGGGAGA AACTTATCTT GGCGGTGACG AGCGTGGCGA    300

AGGTAAAAAC GGCATTCAAT TAGCAAAGAA AACCACTTTA GAAAAAGGCT CAACAATTAA    360

TGTGTCAGGT AAAGAAAAAG CTGGGCGCGC TATTGTATGG GGCGATATTG CGTTAATTGA    420

CGGCAATATT AATGCCCAAG GTAAAGATAT CGCTAAAACT GGTGGTTTTG TGGAGACGTC    480
```

-continued

```
GGGGCATTAC TTATCCATTG ATGATAACGC AATTGTTAAA ACAAAAGAAT GGCTACTAGA    540
CCCAGAGAAT GTGACTATTG AAGCTCCTTC CGCTTCTCGC GTCGAGCTGG GTGCCGATAG    600
GAATTCCCAC TCGGCAGAGG TGATAAAAGT GACCCTAAAA AAAAATAACA CCTCCTTGAC    660
AACACTAACC AATACAACCA TTTCAAATCT TCTGAAAAGT GCCCACGTGG TGAACATAAC    720
GGCAAGGAGA AAACTTACCG TTAATAGCTC TATCAGTATA GAAAGAGGCT CCCACTTAAT    780
TCTCCACAGT GAAGGTCAGG GCGGTCAAGG TGTTCAGATT GATAAAGATA TTACTTCTGA    840
AGGCGGAAAT TTAACCATTT ATTCTGGCGG ATGGGTTGAT GTTCATAAAA ATATTACGCT    900
TGGTAGCGGC TTTTTAAACA TCACAACTAA AGAAGGAGAT ATCGCCTTCG AAGACAAGTC    960
TGGACGGAAC AACCTAACCA TTACAGCCCA AGGGACCATC ACCTCAGGTA ATAGTAACGG   1020
CTTTAGATTT AACAACGTCT CTCTAAACAG CCTTGGCGGA AAGCTGAGCT TTACTGACAG   1080
CAGAGAGGAC AGAGGTAGAA GAACTAAGGG TAATATCTCA AACAAATTTG ACGGAACGTT   1140
AAACATTTCC GGAACTGTAG ATATCTCAAT GAAAGCACCC AAAGTCAGCT GGTTTTACAG   1200
AGACAAAGGA CGCACCTACT GGAACGTAAC CACTTTAAAT GTTACCTCGG GTAGTAAATT   1260
TAACCTCTCC ATTGACAGCA CAGGAAGTGG CTCAACAGGT CCAAGCATAC GCAATGCAGA   1320
ATTAAATGGC ATAACATTTA ATAAAGCCAC TTTTAATATC GCACAAGGCT CAACAGCTAA   1380
CTTTAGCATC AAGGCATCAA TAATGCCCTT TAAGAGTAAC GCTAACTACG CATTATTTAA   1440
TGAAGATATT TCAGTCTCAG GGGGGGGTAG CGTTAATTTC AAACTTAACG CCTCATCTAG   1500
CAACATACAA ACCCCTGGCG TAATTATAAA ATCTCAAAAC TTTAATGTCT CAGGAGGGTC   1560
AACTTTAAAT CTCAAGGCTG AAGGTTCAAC AGAAACCGCT TTTTCAATAG AAAATGATTT   1620
AAACTTAAAC GCCACCGGTG GCAATATAAC AATCAGACAA GTCGAGGGTA CCGATTCACG   1680
CGTCAACAAA GGTGTCGCAG CCAAAAAAAA CATAACTTTT AAAGGGGGTA ATATCACCTT   1740
CGGCTCTCAA AAAGCCACAA CAGAAATCAA AGGCAATGTT ACCATCAATA AAAACACTAA   1800
CGCTACTCTT CGTGGTGCGA ATTTTGCCGA AAACAAATCG CCTTTAAATA TAGCAGGAAA   1860
TGTTATTAAT AATGGCAACC TTACCACTGC CGGCTCCATT ATCAATATAG CCGGAAATCT   1920
TACTGTTTCA AAAGGCGCTA ACCTTCAAGC TATAACAAAT TACACTTTTA ATGTAGCCGG   1980
CTCATTTGAC AACAATGGCG CTTCAAACAT TTCCATTGCC AGAGGAGGGG CTAAATTTAA   2040
AGATATCAAT AACACCAGTA GCTTAAATAT TACCACCAAC TCTGATACCA CTTACCGCAC   2100
CATTATAAAA GGCAATATAT CCAACAAATC AGGTGATTTG AATATTATTG ATAAAAAAAG   2160
CGACGCTGAA ATCCAAATTG GCGGCAATAT CTCACAAAAA GAAGGCAATC TCACAATTTC   2220
TTCTGATAAA GTAAATATTA CCAATCAGAT AACAATCAAA GCAGGCGTTG AAGGGGGGCG   2280
TTCTGATTCA AGTGAGGCAG AAAATGCTAA CCTAACTATT CAAACCAAAG AGTTAAAATT   2340
GGCAGGAGAC CTAAATATTT CAGGCTTTAA TAAAGCAGAA ATTACAGCTA AAAATGGCAG   2400
TGATTTAACT ATTGGCAATG CTAGCGGTGG TAATGCTGAT GCTAAAAAAG TGACTTTTGA   2460
CAAGGTTAAA GATTCAAAAA TCTCGACTGA CGGTCACAAT GTAACACTAA ATAGCGAAGT   2520
GAAAACGTCT AATGGTAGTA GCAATGCTGG TAATGATAAC AGCACCGGTT TAACCATTTC   2580
CGCAAAAGAT GTAACGGTAA ACAATAACGT TACCTCCCAC AAGACAATAA ATATCTCTGC   2640
CGCAGCAGGA AATGTAACAA CCAAAGAAGG CACAACTATC AATGCAACCA CAGGCAGCGT   2700
GGAAGTAACT GCTCAAAATG GTACAATTAA AGGCAACATT ACCTCGCAAA ATGTAACAGT   2760
GACAGCAACA GAAAATCTTG TTACCACAGA GAATGCTGTC ATTAATGCAA CCAGCGGCAC   2820
AGTAAACATT AGTACAAAAA CAGGGGATAT TAAAGGTGGA ATTGAATCAA CTTCCGGTAA   2880
```

-continued

```
TGTAAATATT ACAGCGAGCG GCAATACACT TAAGGTAAGT AATATCACTG GTCAAGATGT   2940

AACAGTAACA GCGGATGCAG GAGCCTTGAC AACTACAGCA GGCTCAACCA TTAGTGCGAC   3000

AACAGGCAAT GCAAATATTA CAACCAAAAC AGGTGATATC AACGGTAAAG TTGAATCCAG   3060

CTCCGGCTCT GTAACACTTG TTGCAACTGG AGCAACTCTT GCTGTAGGTA ATATTTCAGG   3120

TAACACTGTT ACTATTACTG CGGATAGCGG TAAATTAACC TCCACAGTAG GTTCTACAAT   3180

TAATGGGACT AATAGTGTAA CCACCTCAAG CCAATCAGGC GATATTGAAG GTACAATTTC   3240

TGGTAATACA GTAAATGTTA CAGCAAGCAC TGGTGATTTA ACTATTGGAA ATAGTGCAAA   3300

AGTTGAAGCG AAAAATGGAG CTGCAACCTT AACTGCTGAA TCAGGCAAAT TAACCACCCA   3360

AACAGGCTCT AGCATTACCT CAAGCAATGG TCAGACAACT CTTACAGCCA AGGATAGCAG   3420

TATCGCAGGA AACATTAATG CTGCTAATGT GACGTTAAAT ACCACAGGCA CTTTAACTAC   3480

TACAGGGGAT TCAAAGATTA ACGCAACCAG TGGTACCTTA ACAATCAATG CAAAAGATGC   3540

CAAATTAGAT GGTGCTGCAT CAGGTGACCG CACAGTAGTA AATGCAACTA ACGCAAGTGG   3600

CTCTGGTAAC GTGACTGCGA AAACCTCAAG CAGCGTGAAT ATCACCGGGG ATTTAAACAC   3660

AATAAATGGG TTAAATATCA TTTCGGAAAA TGGTAGAAAC ACTGTGCGCT TAAGAGGCAA   3720

GGAAATTGAT GTGAAATATA TCCAACCAGG TGTAGCAAGC GTAGAAGAGG TAATTGAAGC   3780

GAAACGCGTC CTTGAGAAGG TAAAAGATTT ATCTGATGAA GAAAGAGAAA CACTAGCCAA   3840

ACTTGGTGTA AGTGCTGTAC GTTTCGTTGA GCCAAATAAT GCCATTACGG TTAATACACA   3900

AAACGAGTTT ACAACCAAAC CATCAAGTCA AGTGACAATT TCTGAAGGTA AGGCGTGTTT   3960

CTCAAGTGGT AATGGCGCAC GAGTATGTAC CAATGTTGCT GACGATGGAC AGCAGTAGTC   4020

AGTAATTGAC AAGGTAGATT TCATCCTGCA ATGAAGTCAT TTTATTTTCG TATTATTTAC   4080

TGTGTGGGTT AAAGTTCAGT ACGGGCTTTA CCCACCTTGT AAAAAATTAC GAAAAATACA   4140

ATAAAGTATT TTTAACAGGT TATTATTATG AAAAACATAA AAAGCAGATT AAAACTCAGT   4200

GCAATATCAA TATTGCTTGG CTTGGCTTCT TCATCGACGT ATGCAGAAGA AGCGTTTTTA   4260

GTAAAAGGCT TTCAGTTATC TGGCGCG                                      4287
```

(2) INFORMATION FOR SEQ ID NO:8:

(i) SEQUENCE CHARACTERISTICS:
(A) LENGTH: 4702 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
GGGAATGAGC GTCGTACACG GTACAGCAAC CATGCAAGTA GACGGCAATA AAACCACTAT     60

CCGTAATAGC ATCAATGCTA TCATCAATTG GAAACAATTT AACATTGACC AAAATGAAAT    120

GGAGCAGTTT TTACAAGAAA GCAGCAACTC TGCCGTTTTC AACCGTGTTA CATCTGACCA    180

AATCTCCCAA TTAAAAGGGA TTTTAGATTC TAACGGACAA GTCTTTTTAA TCAACCCAAA    240

TGGTATCACA ATAGGTAAAG ACGCAATTAT TAACACTAAT GGCTTTACTG CTTCTACGCT    300

AGACATTTCT AACGAAAACA TCAAGGCGCG TAATTTCACC CTTGAGCAAA CCAAGGATAA    360

AGCACTCGCT GAAATCGTGA ATCACGGTTT AATTACCGTT GGTAAAGACG GTAGCGTAAA    420

CCTTATTGGT GGCAAAGTGA AAAACGAGGG CGTGATTAGC GTAAATGGCG GTAGTATTTC    480

TTTACTTGCA GGGCAAAAAA TCACCATCAG CGATATAATA AATCCAACCA TCACTTACAG    540
```

-continued

```
CATTGCTGCA CCTGAAAACG AAGCGATCAA TCTGGGCGAT ATTTTTGCCA AAGGTGGTAA    600
CATTAATGTC CGCGCTGCCA CTATTCGCAA TAAAGGTAAA CTTTCTGCCG ACTCTGTAAG    660
CAAAGATAAA AGTGGTAACA TTGTTCTCTC TGCCAAAGAA GGTGAAGCGG AAATTGGCGG    720
TGTAATTTCC GCTCAAAATC AGCAAGCCAA AGGTGGTAAG TTGATGATTA CAGGTGATAA    780
AGTCACATTA AAAACAGGTG CAGTTATCGA CCTTTCAGGT AAAGAAGGGG GAGAGACTTA    840
TCTTGGCGGT GATGAGCGTG GCGAAGGTAA AAATGGTATT CAATTAGCGA AGAAAACCTC    900
TTTAGAAAAA GGCTCGACAA TTAATGTATC AGGCAAAGAA AAAGGCGGGC GCGCTATTGT    960
ATGGGGCGAT ATTGCATTAA TTAATGGTAA CATTAATGCT CAAGGTAGCG ATATTGCTAA   1020
AACTGGCGGC TTTGTGGAAA CATCAGGACA TGACTTATCC ATTGGTGATG ATGTGATTGT   1080
TGACGCTAAA GAGTGGTTAT TAGACCCAGA TGATGTGTCC ATTGAAACTC TTACATCTGG   1140
ACGCAATAAT ACCGGCGAAA ACCAAGGATA TACAACAGGA GATGGGACTA AAGAGTCACC   1200
TAAAGGTAAT AGTATTTCTA AACCTACATT AACAAACTCA ACTCTTGAGC AAATCCTAAG   1260
AAGAGGTTCT TATGTTAATA TCACTGCTAA TAATAGAATT TATGTTAATA GCTCCATCAA   1320
CTTATCTAAT GGCAGTTTAA CACTTCACAC TAAACGAGAT GGAGTTAAAA TTAACGGTGA   1380
TATTACCTCA AACGAAAATG GTAATTTAAC CATTAAAGCA GGCTCTTGGG TTGATGTTCA   1440
TAAAAACATC ACGCTTGGTA CGGGTTTTTT CAATATTGTC GCTGGGGATT CTGTAGCTTT   1500
TGAGAGAGAG GGCGATAAAG CACGTAACGC AACAGATGCT CAAATTACCG CACAAGGGAC   1560
GATAACCGTC AATAAAGATG ATAAACAATT TAGATTCAAT AATGTATCTA TTAACGGGAC   1620
GGGCAAGGGT TTAAAGTTTA TTGCAAATCA AAATAATTTC ACTCATAAAT TTGATGGCGA   1680
AATTAACATA TCTGGAATAG TAACAATTAA CCAAACCACG AAAAAAGATG TTAAATACTG   1740
GAATGCATCA AAAGACTCTT ACTGGAATGT TTCTTCTCTT ACTTTGAATA CGGTGCAAAA   1800
ATTTACCTTT ATAAAATTCG TTGATAGCGG CTCAAATTCC CAAGATTTGA GGTCATCACG   1860
TAGAAGTTTT GCAGGCGTAC ATTTTAACGG CATCGGAGGC AAAACAAACT TCAACATCGG   1920
AGCTAACGCA AAAGCCTTAT TTAAATTAAA ACCAAACGCC GCTACAGACC CAAAAAAAGA   1980
ATTACCTATT ACTTTTAACG CCAACATTAC AGCTACCGGT AACAGTGATA GCTCTGTGAT   2040
GTTTGACATA CACGCCAATC TTACCTCTAG AGCTGCCGGC ATAAACATGG ATTCAATTAA   2100
CATTACCGGC GGGCTTGACT TTTCCATAAC ATCCCATAAT CGCAATAGTA ATGCTTTTGA   2160
AATCAAAAAA GACTTAACTA TAAATGCAAC TGGCTCGAAT TTTAGTCTTA AGCAAACGAA   2220
AGATTCTTTT TATAATGAAT ACAGCAAACA CGCCATTAAC TCAAGTCATA ATCTAACCAT   2280
TCTTGGCGGC AATGTCACTC TAGGTGGGGA AAATTCAAGC AGTAGCATTA CGGGCAATAT   2340
CAATATCACC AATAAAGCAA ATGTTACATT ACAAGCTGAC ACCAGCAACA GCAACACAGG   2400
CTTGAAGAAA AGAACTCTAA CTCTTGGCAA TATATCTGTT GAGGGGAATT TAAGCCTAAC   2460
TGGTGCAAAT GCAAACATTG TCGGCAATCT TTCTATTGCA GAAGATTCCA CATTTAAAGG   2520
AGAAGCCAGT GACAACCTAA ACATCACCGG CACCTTTACC AACAACGGTA CCGCCAACAT   2580
TAATATAAAA CAAGGAGTGG TAAAACTCCA AGGCGATATT ATCAATAAAG GTGGTTTAAA   2640
TATCACTACT AACGCCTCAG GCACTCAAAA AACCATTATT AACGGAAATA TAACTAACGA   2700
AAAAGGCGAC TTAAACATCA AGAATATTAA AGCCGACGCC GAAATCCAAA TTGGCGGCAA   2760
TATCTCACAA AAAGAAGGCA ATCTCACAAT TTCTTCTGAT AAAGTAAATA TTACCAATCA   2820
GATAACAATC AAAGCAGGCG TTGAAGGGGG GCGTTCTGAT TCAAGTGAGG CAGAAAATGC   2880
```

-continued

```
TAACCTAACT ATTCAAACCA AAGAGTTAAA ATTGGCAGGA GACCTAAATA TTTCAGGCTT   2940

TAATAAAGCA GAAATTACAG CTAAAAATGG CAGTGATTTA ACTATTGGCA ATGCTAGCGG   3000

TGGTAATGCT GATGCTAAAA AAGTGACTTT TGACAAGGTT AAAGATTCAA AAATCTCGAC   3060

TGACGGTCAC AATGTAACAC TAAATAGCGA AGTGAAAACG TCTAATGGTA GTAGCAATGC   3120

TGGTAATGAT AACAGCACCG GTTTAACCAT TTCCGCAAAA GATGTAACGG TAAACAATAA   3180

CGTTACCTCC CACAAGACAA TAAATATCTC TGCCGCAGCA GGAAATGTAA CAACCAAAGA   3240

AGGCACAACT ATCAATGCAA CCACAGGCAG CGTGGAAGTA ACTGCTCAAA ATGGTACAAT   3300

TAAAGGCAAC ATTACCTCGC AAAATGTAAC AGTGACAGCA ACAGAAAATC TTGTTACCAC   3360

AGAGAATGCT GTCATTAATG CAACCAGCGG CACAGTAAAC ATTAGTACAA AAACAGGGGA   3420

TATTAAAGGT GGAATTGAAT CAACTTCCGG TAATGTAAAT ATTACAGCGA GCGGCAATAC   3480

ACTTAAGGTA AGTAATATCA CTGGTCAAGA TGTAACAGTA ACAGCGGATG CAGGAGCCTT   3540

GACAACTACA GCAGGCTCAA CCATTAGTGC GACAACAGGC AATGCAAATA TTACAACCAA   3600

AACAGGTGAT ATCAACGGTA AAGTTGAATC CAGCTCCGGC TCTGTAACAC TTGTTGCAAC   3660

TGGAGCAACT CTTGCTGTAG GTAATATTTC AGGTAACACT GTTACTATTA CTGCGGATAG   3720

CGGTAAATTA ACCTCCACAG TAGGTTCTAC AATTAATGGG ACTAATAGTG TAACCACCTC   3780

AAGCCAATCA GGCGATATTG AAGGTACAAT TTCTGGTAAT ACAGTAAATG TTACAGCAAG   3840

CACTGGTGAT TTAACTATTG GAAATAGTGC AAAAGTTGAA GCGAAAAATG GAGCTGCAAC   3900

CTTAACTGCT GAATCAGGCA AATTAACCAC CCAAACAGGC TCTAGCATTA CCTCAAGCAA   3960

TGGTCAGACA ACTCTTACAG CCAAGGATAG CAGTATCGCA GGAAACATTA ATGCTGCTAA   4020

TGTGACGTTA AATACCACAG GCACTTTAAC TACTACAGGG GATTCAAAGA TTAACGCAAC   4080

CAGTGGTACC TTAACAATCA ATGCAAAAGA TGCCAAATTA GATGGTGCTG CATCAGGTGA   4140

CCGCACAGTA GTAAATGCAA CTAACGCAAG TGGCTCTGGT AACGTGACTG CGAAAACCTC   4200

AAGCAGCGTG AATATCACCG GGGATTTAAA CACAATAAAT GGGTTAAATA TCATTTCGGA   4260

AAATGGTAGA AACACTGTGC GCTTAAGAGG CAAGGAAATT GATGTGAAAT ATATCCAACC   4320

AGGTGTAGCA AGCGTAGAAG AGGTAATTGA AGCGAAACGC GTCCTTGAGA AGGTAAAAGA   4380

TTTATCTGAT GAAGAAAGAG AAACACTAGC CAAACTTGGT GTAAGTGCTG TACGTTTCGT   4440

TGAGCCAAAT AATGCCATTA CGGTTAATAC ACAAAACGAG TTTACAACCA AACCATCAAG   4500

TCAAGTGACA ATTTCTGAAG GTAAGGCGTG TTTCTCAAGT GGTAATGGCG CACGAGTATG   4560

TACCAATGTT GCTGACGATG GACAGCAGTA GTCAGTAATT GACAAGGTAG ATTTCATCCT   4620

GCAATGAAGT CATTTTATTT TCGTATTATT TACTGTGTGG GTTAAAGTTC AGTACGGGCT   4680

TTACCCACCT TGTAAAAAAT TA                                            4702
```

(2) INFORMATION FOR SEQ ID NO:9:

(i) SEQUENCE CHARACTERISTICS:
(A) LENGTH: 1338 amino acids
(B) TYPE: amino acid
(C) STRANDEDNESS: single
(D) TOPOLOGY: linear (xi) SEQUENCE DESCRIPTION: SEQ ID NO:9:

```
Ile Asn Leu Gly Asp Ile Phe Ala Lys Gly Gly Asn Ile Asn Val Arg
1               5                   10                  15

Ala Ala Thr Ile Arg Asn Lys Gly Lys Leu Ser Ala Asp Ser Val Ser
            20                  25                  30
```

-continued

```
Lys Asp Lys Ser Gly Asn Ile Val Leu Ser Ala Lys Glu Gly Glu Ala
        35                  40                  45

Glu Ile Gly Gly Val Ile Ser Ala Gln Asn Gln Gln Ala Lys Gly Gly
    50                  55                  60

Lys Leu Met Ile Thr Gly Asp Lys Val Thr Leu Lys Thr Gly Ala Val
65                  70                  75                  80

Ile Asp Leu Ser Gly Lys Glu Gly Gly Glu Thr Tyr Leu Gly Gly Asp
                85                  90                  95

Glu Arg Gly Glu Gly Lys Asn Gly Ile Gln Leu Ala Lys Lys Thr Thr
            100                 105                 110

Leu Glu Lys Gly Ser Thr Ile Asn Val Ser Gly Lys Glu Lys Gly Gly
        115                 120                 125

Arg Ala Ile Val Trp Gly Asp Ile Ala Leu Ile Asp Gly Asn Ile Asn
    130                 135                 140

Ala Gln Gly Lys Asp Ile Ala Lys Thr Gly Gly Phe Val Glu Thr Ser
145                 150                 155                 160

Gly His Tyr Leu Ser Ile Asp Asp Asn Ala Ile Val Lys Thr Lys Glu
                165                 170                 175

Trp Leu Leu Asp Pro Glu Asn Val Thr Ile Glu Ala Pro Ser Ala Ser
            180                 185                 190

Arg Val Glu Leu Gly Ala Asp Arg Asn Ser His Ser Ala Glu Val Ile
        195                 200                 205

Lys Val Thr Leu Lys Lys Asn Asn Thr Ser Leu Thr Thr Leu Thr Asn
    210                 215                 220

Thr Thr Ile Ser Asn Leu Leu Lys Ser Ala His Val Val Asn Ile Thr
225                 230                 235                 240

Ala Arg Arg Lys Leu Thr Val Asn Ser Ser Ile Ser Ile Glu Arg Gly
                245                 250                 255

Ser His Leu Ile Leu His Ser Glu Gly Gln Gly Gly Gln Gly Val Gln
            260                 265                 270

Ile Asp Lys Asp Ile Thr Ser Glu Gly Gly Asn Leu Thr Ile Tyr Ser
        275                 280                 285

Gly Gly Trp Val Asp Val His Lys Asn Ile Thr Leu Gly Ser Gly Phe
    290                 295                 300

Leu Asn Ile Thr Thr Lys Glu Gly Asp Ile Ala Phe Glu Asp Lys Ser
305                 310                 315                 320

Gly Arg Asn Asn Leu Thr Ile Thr Ala Gln Gly Thr Ile Thr Ser Gly
                325                 330                 335

Asn Ser Asn Gly Phe Arg Phe Asn Asn Val Ser Leu Asn Ser Leu Gly
            340                 345                 350

Gly Lys Leu Ser Phe Thr Asp Ser Arg Glu Asp Arg Gly Arg Arg Thr
        355                 360                 365

Lys Gly Asn Ile Ser Asn Lys Phe Asp Gly Thr Leu Asn Ile Ser Gly
    370                 375                 380

Thr Val Asp Ile Ser Met Lys Ala Pro Lys Val Ser Trp Phe Tyr Arg
385                 390                 395                 400

Asp Lys Gly Arg Thr Tyr Trp Asn Val Thr Thr Leu Asn Val Thr Ser
                405                 410                 415

Gly Ser Lys Phe Asn Leu Ser Ile Asp Ser Thr Gly Ser Gly Ser Thr
            420                 425                 430

Gly Pro Ser Ile Arg Asn Ala Glu Leu Asn Gly Ile Thr Phe Asn Lys
        435                 440                 445

Ala Thr Phe Asn Ile Ala Gln Gly Ser Thr Ala Asn Phe Ser Ile Lys
```

-continued

```
    450                 455                 460

Ala Ser Ile Met Pro Phe Lys Ser Asn Ala Asn Tyr Ala Leu Phe Asn
465                 470                 475                 480

Glu Asp Ile Ser Val Ser Gly Gly Gly Ser Val Asn Phe Lys Leu Asn
                485                 490                 495

Ala Ser Ser Ser Asn Ile Gln Thr Pro Gly Val Ile Ile Lys Ser Gln
            500                 505                 510

Asn Phe Asn Val Ser Gly Gly Ser Thr Leu Asn Leu Lys Ala Glu Gly
        515                 520                 525

Ser Thr Glu Thr Ala Phe Ser Ile Glu Asn Asp Leu Asn Leu Asn Ala
    530                 535                 540

Thr Gly Gly Asn Ile Thr Ile Arg Gln Val Glu Gly Thr Asp Ser Arg
545                 550                 555                 560

Val Asn Lys Gly Val Ala Ala Lys Lys Asn Ile Thr Phe Lys Gly Gly
                565                 570                 575

Asn Ile Thr Phe Gly Ser Gln Lys Ala Thr Thr Glu Ile Lys Gly Asn
            580                 585                 590

Val Thr Ile Asn Lys Asn Thr Asn Ala Thr Leu Arg Gly Ala Asn Phe
        595                 600                 605

Ala Glu Asn Lys Ser Pro Leu Asn Ile Ala Gly Asn Val Ile Asn Asn
    610                 615                 620

Gly Asn Leu Thr Thr Ala Gly Ser Ile Ile Asn Ile Ala Gly Asn Leu
625                 630                 635                 640

Thr Val Ser Lys Gly Ala Asn Leu Gln Ala Ile Thr Asn Tyr Thr Phe
                645                 650                 655

Asn Val Ala Gly Ser Phe Asp Asn Asn Gly Ala Ser Asn Ile Ser Ile
            660                 665                 670

Ala Arg Gly Gly Ala Lys Phe Lys Asp Ile Asn Asn Thr Ser Ser Leu
        675                 680                 685

Asn Ile Thr Thr Asn Ser Asp Thr Thr Tyr Arg Thr Ile Ile Lys Gly
    690                 695                 700

Asn Ile Ser Asn Lys Ser Gly Asp Leu Asn Ile Ile Asp Lys Lys Ser
705                 710                 715                 720

Asp Ala Glu Ile Gln Ile Gly Gly Asn Ile Ser Gln Lys Glu Gly Asn
                725                 730                 735

Leu Thr Ile Ser Ser Asp Lys Val Asn Ile Thr Asn Gln Ile Thr Ile
            740                 745                 750

Lys Ala Gly Val Glu Gly Gly Arg Ser Asp Ser Ser Glu Ala Glu Asn
        755                 760                 765

Ala Asn Leu Thr Ile Gln Thr Lys Glu Leu Lys Leu Ala Gly Asp Leu
    770                 775                 780

Asn Ile Ser Gly Phe Asn Lys Ala Glu Ile Thr Ala Lys Asn Gly Ser
785                 790                 795                 800

Asp Leu Thr Ile Gly Asn Ala Ser Gly Gly Asn Ala Asp Ala Lys Lys
                805                 810                 815

Val Thr Phe Asp Lys Val Lys Asp Ser Lys Ile Ser Thr Asp Gly His
            820                 825                 830

Asn Val Thr Leu Asn Ser Glu Val Lys Thr Ser Asn Gly Ser Ser Asn
        835                 840                 845

Ala Gly Asn Asp Asn Ser Thr Gly Leu Thr Ile Ser Ala Lys Asp Val
    850                 855                 860

Thr Val Asn Asn Asn Val Thr Ser His Lys Thr Ile Asn Ile Ser Ala
865                 870                 875                 880
```

-continued

```
Ala Ala Gly Asn Val Thr Thr Lys Glu Gly Thr Thr Ile Asn Ala Thr
                885                 890                 895

Thr Gly Ser Val Glu Val Thr Ala Gln Asn Gly Thr Ile Lys Gly Asn
            900                 905                 910

Ile Thr Ser Gln Asn Val Thr Val Thr Ala Thr Glu Asn Leu Val Thr
        915                 920                 925

Thr Glu Asn Ala Val Ile Asn Ala Thr Ser Gly Thr Val Asn Ile Ser
    930                 935                 940

Thr Lys Thr Gly Asp Ile Lys Gly Gly Ile Glu Ser Thr Ser Gly Asn
945                 950                 955                 960

Val Asn Ile Thr Ala Ser Gly Asn Thr Leu Lys Val Ser Asn Ile Thr
                965                 970                 975

Gly Gln Asp Val Thr Val Thr Ala Asp Ala Gly Ala Leu Thr Thr Thr
            980                 985                 990

Ala Gly Ser Thr Ile Ser Ala Thr Thr Gly Asn Ala Asn Ile Thr Thr
        995                 1000                1005

Lys Thr Gly Asp Ile Asn Gly Lys Val Glu Ser Ser Ser Gly Ser Val
    1010                1015                1020

Thr Leu Val Ala Thr Gly Ala Thr Leu Ala Val Gly Asn Ile Ser Gly
1025                1030                1035                1040

Asn Thr Val Thr Ile Thr Ala Asp Ser Gly Lys Leu Thr Ser Thr Val
                1045                1050                1055

Gly Ser Thr Ile Asn Gly Thr Asn Ser Val Thr Thr Ser Ser Gln Ser
            1060                1065                1070

Gly Asp Ile Glu Gly Thr Ile Ser Gly Asn Thr Val Asn Val Thr Ala
        1075                1080                1085

Ser Thr Gly Asp Leu Thr Ile Gly Asn Ser Ala Lys Val Glu Ala Lys
    1090                1095                1100

Asn Gly Ala Ala Thr Leu Thr Ala Glu Ser Gly Lys Leu Thr Thr Gln
1105                1110                1115                1120

Thr Gly Ser Ser Ile Thr Ser Ser Asn Gly Gln Thr Thr Leu Thr Ala
                1125                1130                1135

Lys Asp Ser Ser Ile Ala Gly Asn Ile Asn Ala Ala Asn Val Thr Leu
            1140                1145                1150

Asn Thr Thr Gly Thr Leu Thr Thr Thr Gly Asp Ser Lys Ile Asn Ala
        1155                1160                1165

Thr Ser Gly Thr Leu Thr Ile Asn Ala Lys Asp Ala Lys Leu Asp Gly
    1170                1175                1180

Ala Ala Ser Gly Asp Arg Thr Val Val Asn Ala Thr Asn Ala Ser Gly
1185                1190                1195                1200

Ser Gly Asn Val Thr Ala Lys Thr Ser Ser Ser Val Asn Ile Thr Gly
                1205                1210                1215

Asp Leu Asn Thr Ile Asn Gly Leu Asn Ile Ile Ser Glu Asn Gly Arg
            1220                1225                1230

Asn Thr Val Arg Leu Arg Gly Lys Glu Ile Asp Val Lys Tyr Ile Gln
        1235                1240                1245

Pro Gly Val Ala Ser Val Glu Glu Val Ile Glu Ala Lys Arg Val Leu
    1250                1255                1260

Glu Lys Val Lys Asp Leu Ser Asp Glu Glu Arg Glu Thr Leu Ala Lys
1265                1270                1275                1280

Leu Gly Val Ser Ala Val Arg Phe Val Glu Pro Asn Asn Ala Ile Thr
                1285                1290                1295
```

-continued

```
Val Asn Thr Gln Asn Glu Phe Thr Thr Lys Pro Ser Ser Gln Val Thr
            1300                1305                1310

Ile Ser Glu Gly Lys Ala Cys Phe Ser Ser Gly Asn Gly Ala Arg Val
        1315                1320                1325

Cys Thr Asn Val Ala Asp Asp Gly Gln Gln
    1330                1335
```

(2) INFORMATION FOR SEQ ID NO:10:

(i) SEQUENCE CHARACTERISTICS:
(A) LENGTH: 1529 amino acids
(B) TYPE: amino acid
(C) STRANDEDNESS: single
(D) TOPOLOGY: linear (xi) SEQUENCE DESCRIPTION: SEQ ID NO:10:

```
Gly Met Ser Val Val His Gly Thr Ala Thr Met Gln Val Asp Gly Asn
1               5                   10                  15

Lys Thr Thr Ile Arg Asn Ser Val Asn Ala Ile Ile Asn Trp Lys Gln
            20                  25                  30

Phe Asn Ile Asp Gln Asn Glu Met Glu Gln Phe Leu Gln Glu Ser Ser
        35                  40                  45

Asn Ser Ala Val Phe Asn Arg Val Thr Ser Asp Gln Ile Ser Gln Leu
    50                  55                  60

Lys Gly Ile Leu Asp Ser Asn Gly Gln Val Phe Leu Ile Asn Pro Asn
65                  70                  75                  80

Gly Ile Thr Ile Gly Lys Asp Ala Ile Ile Asn Thr Asn Gly Phe Thr
                85                  90                  95

Ala Ser Thr Leu Asp Ile Ser Asn Glu Asn Ile Lys Ala Arg Asn Phe
            100                 105                 110

Thr Leu Glu Gln Thr Lys Asp Lys Ala Leu Ala Glu Ile Val Asn His
        115                 120                 125

Gly Leu Ile Thr Val Gly Lys Asp Gly Ser Val Asn Leu Ile Gly Gly
    130                 135                 140

Lys Val Lys Asn Glu Gly Val Ile Ser Val Asn Gly Gly Ser Ile Ser
145                 150                 155                 160

Leu Leu Ala Gly Gln Lys Ile Thr Ile Ser Asp Ile Ile Asn Pro Thr
                165                 170                 175

Ile Thr Tyr Ser Ile Ala Ala Pro Glu Asn Glu Ala Ile Asn Leu Gly
            180                 185                 190

Asp Ile Phe Ala Lys Gly Gly Asn Ile Asn Val Arg Ala Ala Thr Ile
        195                 200                 205

Arg Asn Lys Gly Lys Leu Ser Ala Asp Ser Val Ser Lys Asp Lys Ser
    210                 215                 220

Gly Asn Ile Val Leu Ser Ala Lys Glu Gly Glu Ala Glu Ile Gly Gly
225                 230                 235                 240

Val Ile Ser Ala Gln Asn Gln Gln Ala Lys Gly Gly Lys Leu Met Ile
                245                 250                 255

Thr Gly Asp Lys Val Thr Leu Lys Thr Gly Ala Val Ile Asp Leu Ser
            260                 265                 270

Gly Lys Glu Gly Gly Glu Thr Tyr Leu Gly Gly Asp Glu Arg Gly Glu
        275                 280                 285

Gly Lys Asn Gly Ile Gln Leu Ala Lys Lys Thr Thr Leu Glu Lys Gly
    290                 295                 300

Ser Thr Ile Asn Val Ser Gly Lys Glu Lys Gly Gly Arg Ala Ile Val
305                 310                 315                 320
```

-continued

```
Trp Gly Asp Ile Ala Leu Ile Asp Gly Asn Ile Asn Ala Gln Gly Ser
                325                 330                 335

Asp Ile Ala Lys Thr Gly Gly Phe Val Glu Thr Ser Gly His Asp Leu
            340                 345                 350

Ser Ile Gly Asp Asp Val Ile Val Asp Ala Lys Glu Trp Leu Leu Asp
        355                 360                 365

Pro Asp Asp Val Ser Ile Glu Thr Leu Thr Ser Gly Arg Asn Asn Thr
    370                 375                 380

Gly Glu Asn Gln Gly Tyr Thr Thr Gly Asp Gly Thr Lys Glu Ser Pro
385                 390                 395                 400

Lys Gly Asn Ser Ile Ser Lys Pro Thr Leu Thr Asn Ser Thr Leu Glu
                405                 410                 415

Gln Ile Leu Arg Arg Gly Ser Tyr Val Asn Ile Thr Ala Asn Asn Arg
            420                 425                 430

Ile Tyr Val Asn Ser Ser Ile Asn Leu Ser Asn Gly Ser Leu Thr Leu
        435                 440                 445

His Thr Lys Arg Asp Gly Val Lys Ile Asn Gly Asp Ile Thr Ser Asn
    450                 455                 460

Glu Asn Gly Asn Leu Thr Ile Lys Ala Gly Ser Trp Val Asp Val His
465                 470                 475                 480

Lys Asn Ile Thr Leu Gly Thr Gly Phe Leu Asn Ile Val Ala Gly Asp
                485                 490                 495

Ser Val Ala Phe Glu Arg Glu Gly Asp Lys Ala Arg Asn Ala Thr Asp
            500                 505                 510

Ala Gln Ile Thr Ala Gln Gly Thr Ile Thr Val Asn Lys Asp Asp Lys
        515                 520                 525

Gln Phe Arg Phe Asn Asn Val Ser Ile Asn Gly Thr Gly Lys Gly Leu
    530                 535                 540

Lys Phe Ile Ala Asn Gln Asn Asn Phe Thr His Lys Phe Asp Gly Glu
545                 550                 555                 560

Leu Asn Ile Ser Gly Ile Val Thr Ile Asn Gln Thr Thr Lys Lys Asp
                565                 570                 575

Val Lys Tyr Trp Asn Ala Ser Lys Asp Ser Tyr Trp Asn Val Ser Ser
            580                 585                 590

Leu Thr Leu Asn Thr Val Gln Lys Phe Thr Phe Ile Lys Phe Val Asp
        595                 600                 605

Ser Gly Ser Asn Ser Gln Asp Leu Arg Ser Ser Arg Arg Ser Phe Ala
    610                 615                 620

Gly Val His Phe Asn Gly Ile Gly Gly Lys Thr Asn Phe Asn Ile Gly
625                 630                 635                 640

Ala Asn Ala Lys Ala Leu Phe Lys Leu Lys Pro Asn Ala Ala Thr Asp
                645                 650                 655

Pro Lys Lys Glu Leu Pro Ile Thr Phe Asn Ala Asn Ile Thr Ala Thr
            660                 665                 670

Gly Asn Ser Asp Ser Ser Val Met Phe Asp Ile His Ala Asn Leu Thr
        675                 680                 685

Ser Arg Ala Ala Gly Ile Asn Met Asp Ser Ile Asn Ile Thr Gly Gly
    690                 695                 700

Leu Asp Phe Ser Ile Thr Ser His Asn Arg Asn Ser Asn Ala Phe Glu
705                 710                 715                 720

Ile Lys Lys Asp Leu Thr Ile Asn Ala Thr Gly Ser Asn Phe Ser Leu
                725                 730                 735
```

-continued

```
Lys Gln Thr Lys Asp Ser Phe Tyr Asn Glu Tyr Ser Lys His Ala Ile
            740                 745                 750

Asn Ser Ser His Asn Leu Thr Ile Leu Gly Gly Asn Val Thr Leu Gly
        755                 760                 765

Gly Glu Asn Ser Ser Ser Ser Ile Thr Gly Asn Ile Asn Ile Thr Asn
    770                 775                 780

Lys Ala Asn Val Thr Leu Gln Ala Asp Thr Ser Asn Ser Asn Thr Gly
785                 790                 795                 800

Leu Lys Lys Arg Thr Leu Thr Leu Gly Asn Ile Ser Val Glu Gly Asn
                805                 810                 815

Leu Ser Leu Thr Gly Ala Asn Ala Asn Ile Val Gly Asn Leu Ser Ile
            820                 825                 830

Ala Glu Asp Ser Thr Phe Lys Gly Glu Ala Ser Asp Asn Leu Asn Ile
        835                 840                 845

Thr Gly Thr Phe Thr Asn Asn Gly Thr Ala Asn Ile Asn Ile Lys Gln
    850                 855                 860

Gly Val Val Lys Leu Gln Gly Asp Ile Asn Asn Lys Gly Gly Leu Asn
865                 870                 875                 880

Ile Thr Thr Asn Ala Ser Gly Thr Gln Lys Thr Ile Ile Asn Gly Asn
                885                 890                 895

Ile Thr Asn Glu Lys Gly Asp Leu Asn Ile Lys Asn Ile Lys Ala Asp
            900                 905                 910

Ala Glu Ile Gln Ile Gly Gly Asn Ile Ser Gln Lys Glu Gly Asn Leu
        915                 920                 925

Thr Ile Ser Ser Asp Lys Val Asn Ile Thr Asn Gln Ile Thr Ile Lys
    930                 935                 940

Ala Gly Val Glu Gly Gly Arg Ser Asp Ser Ser Glu Ala Glu Asn Ala
945                 950                 955                 960

Asn Leu Thr Ile Gln Thr Lys Glu Leu Lys Leu Ala Gly Asp Leu Asn
                965                 970                 975

Ile Ser Gly Phe Asn Lys Ala Glu Ile Thr Ala Lys Asn Gly Ser Asp
            980                 985                 990

Leu Thr Ile Gly Asn Ala Ser Gly Gly Asn Ala Asp Ala Lys Lys Val
        995                 1000                1005

Thr Phe Asp Lys Val Lys Asp Ser Lys Ile Ser Thr Asp Gly His Asn
    1010                1015                1020

Val Thr Leu Asn Ser Glu Val Lys Thr Ser Asn Gly Ser Ser Asn Ala
1025                1030                1035                1040

Gly Asn Asp Asn Ser Thr Gly Leu Thr Ile Ser Ala Lys Asp Val Thr
                1045                1050                1055

Val Asn Asn Asn Val Thr Ser His Lys Thr Ile Asn Ile Ser Ala Ala
            1060                1065                1070

Ala Gly Asn Val Thr Thr Lys Glu Gly Thr Thr Ile Asn Ala Thr Thr
        1075                1080                1085

Gly Ser Val Glu Val Thr Ala Gln Asn Gly Thr Ile Lys Gly Asn Ile
    1090                1095                1100

Thr Ser Gln Asn Val Thr Val Thr Ala Thr Glu Asn Leu Val Thr Thr
1105                1110                1115                1120

Glu Asn Ala Val Ile Asn Ala Thr Ser Gly Thr Val Asn Ile Ser Thr
                1125                1130                1135

Lys Thr Gly Asp Ile Lys Gly Gly Ile Glu Ser Thr Ser Gly Asn Val
            1140                1145                1150

Asn Ile Thr Ala Ser Gly Asn Thr Leu Lys Val Ser Asn Ile Thr Gly
```

-continued

```
        1155                1160                1165

Gln Asp Val Thr Val Thr Ala Asp Ala Gly Ala Leu Thr Thr Thr Ala
    1170                1175                1180

Gly Ser Thr Ile Ser Ala Thr Thr Gly Asn Ala Asn Ile Thr Thr Lys
1185                1190                1195                1200

Thr Gly Asp Ile Asn Gly Lys Val Glu Ser Ser Ser Gly Ser Val Thr
                1205                1210                1215

Leu Val Ala Thr Gly Ala Thr Leu Ala Val Gly Asn Ile Ser Gly Asn
            1220                1225                1230

Thr Val Thr Ile Thr Ala Asp Ser Gly Lys Leu Thr Ser Thr Val Gly
        1235                1240                1245

Ser Thr Ile Asn Gly Thr Asn Ser Val Thr Thr Ser Ser Gln Ser Gly
    1250                1255                1260

Asp Ile Glu Gly Thr Ile Ser Gly Asn Thr Val Asn Val Thr Ala Ser
1265                1270                1275                1280

Thr Gly Asp Leu Thr Ile Gly Asn Ser Ala Lys Val Glu Ala Lys Asn
                1285                1290                1295

Gly Ala Ala Thr Leu Thr Ala Glu Ser Gly Lys Leu Thr Thr Gln Thr
            1300                1305                1310

Gly Ser Ser Ile Thr Ser Ser Asn Gly Gln Thr Thr Leu Thr Ala Lys
        1315                1320                1325

Asp Ser Ser Ile Ala Gly Asn Ile Asn Ala Ala Asn Val Thr Leu Asn
    1330                1335                1340

Thr Thr Gly Thr Leu Thr Thr Thr Gly Asp Ser Lys Ile Asn Ala Thr
1345                1350                1355                1360

Ser Gly Thr Leu Thr Ile Asn Ala Lys Asp Ala Lys Leu Asp Gly Ala
                1365                1370                1375

Ala Ser Gly Asp Arg Thr Val Val Asn Ala Thr Asn Ala Ser Gly Ser
            1380                1385                1390

Gly Asn Val Thr Ala Lys Thr Ser Ser Ser Val Asn Ile Thr Gly Asp
        1395                1400                1405

Leu Asn Thr Ile Asn Gly Leu Asn Ile Ile Ser Glu Asn Gly Arg Asn
    1410                1415                1420

Thr Val Arg Leu Arg Gly Lys Glu Ile Asp Val Lys Tyr Ile Gln Pro
1425                1430                1435                1440

Gly Val Ala Ser Val Glu Glu Val Ile Glu Ala Lys Arg Val Leu Glu
                1445                1450                1455

Lys Val Lys Asp Leu Ser Asp Glu Glu Arg Glu Thr Leu Ala Lys Leu
            1460                1465                1470

Gly Val Ser Ala Val Arg Phe Val Glu Pro Asn Asn Ala Ile Thr Val
        1475                1480                1485

Asn Thr Gln Asn Glu Phe Thr Thr Lys Pro Ser Ser Gln Val Thr Ile
    1490                1495                1500

Ser Glu Gly Lys Ala Cys Phe Ser Ser Gly Asn Gly Ala Arg Val Cys
1505                1510                1515                1520

Thr Asn Val Ala Asp Asp Gly Gln Gln
                1525
```